United States Patent
Hahn et al.

(10) Patent No.: US 6,521,739 B1
(45) Date of Patent: Feb. 18, 2003

(54) COMPLETE GENOME SEQUENCE OF A SIMIAN IMMUNODEFICIENCY VIRUS FROM A RED-CAPPED MANGABEY

(75) Inventors: Beatrice H. Hahn, Birmingham, AL (US); Feng Gao, Hoover, AL (US); George M. Shaw, Birmingham, AL (US); Preston A. Marx, Covington, LA (US); Stephen M. Smith, Essex Fells, NJ (US); Marie Claude Georges-Courbot, Paris (FR); Chang Yong Lu, Forest Hills, NY (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/206,551

(22) Filed: Dec. 7, 1998

(51) Int. Cl.[7] .......................... A61K 38/00; C07H 21/04
(52) U.S. Cl. .......................... 530/324; 530/324; 514/12; 536/23.72
(58) Field of Search .......................... 435/5, 69.1, 69.3; 530/350, 324, 327; 514/2; 536/23.72

(56) References Cited

PUBLICATIONS

Smith, S.M., et al. Journal of Medical Primatology, vol. 27, issues 2/3, Apr./Jun. 1998, pp. 94–98.*
Georges–Courbot, M.C., et al., Journal of Virology, vol. 72, No. 1, Jan. 1998, pp. 600–608.*
Smith et al. "SIVrcm infection in macaques," J Med Primatology, vol. 28, 1998, pp. 94–98.*
Georges–Courbot, M.C., Lu, C.Y., Makuwa, M., Telfer, P., Onanga, R., Dubreuil, G., Chen, Z., Smith, S.M., Georges, A., Gao, F., Hahn, B.H., and Marx, P.A. "Natural infection of a household pet red capped mangabey (*Cercocebus torquatus torquatus*) with a new simian immunodeficiency virus." *J. Virol.*, 72:600–608 (1998).

B. H. Hahn, Feng Gao, D. L. Robertson, P. A. Marx and P. Sharp. "HIV and Its Primate Cousins: An Evolving Story", Absract 005, *HIV Pathog. Treat. Conf.*, Park City, Utah (Mar. 13–19, 1998).

Feng Gao, Yingying Li, J. Decker, D. L. Robertson, S. Smith, P. A. Marx and B. H. Hahn. "Molecular Characterization of a New Primate Lentivirus (SIVrcm) Isolated from a Pet Red–Capped Mangabey in Gabon", Abstract 4031, *HIV Pathog. Treat. Conf.*, Park City, Utah (Mar. 13–19, 1998).

P. A. Marx, Z. Chen, D. Kwon, S. M. Smith, Feng Gao and B. H. Hahn, "Natural infection of a household pet mangabey (*Cercocebus torquatus torquatus*) with a new simian immunodeficiency virus related to HIV–1 and HIV–2 has implications for the ancient ancestry of HIV", Abstract 012, *HIV Pathog. Treat. Conf.*, Park City, Utah (Mar. 13–19, 1998).

Marx PA; Lu CY; Makuwa M; Georges–Courbot MC; Telfer P; Dubreuil G; Chen Z; Smith SM; Gao F; Hahn, "Natural infection of a household pet mangabey (*Cercocebus torquatus torquatus*) wth a new simian immunodeficiency virus related to HIV–1", Abstract 557, *5th Conf. Retrovir. Oppor. Infect.*, Chicago, Illinois (Feb. 1–5, 1998).

Smith, S.M. Makuwa, M., Lee, F., Gettie, A., Russo, C., Marx, P.A., "SIVrcm infection of macaques" *J. Med. Primatol.* 27:94–98 (Apr./Jun. 1998).

Printout of GenBank accession Nos. AF028607 and AF028608 (Feb. 24, 1998).

* cited by examiner

*Primary Examiner*—B. L. Sisson
(74) *Attorney, Agent, or Firm*—Benjamin Aaron Adler

(57) ABSTRACT

The nucleotide sequence and deduced amino acid sequences of the complete genome of a simian immunodeficiency virus isolate from a red-capped mangabey are disclosed. The invention relates to the nucleic acids and peptides encoded by and/or derived from these sequences and their use in diagnostic methods and as immunogens.

2 Claims, 22 Drawing Sheets

```
SIVRCM       MD............KKLVIV....................LIVVIGIILVQGSQKPQYITVFYGVPV    35
A_U455       -R.V....MGIQRNYPC-WRW...............GT....M-LGLI--.CN.A.QQLWV--Y-----    42
B_HXB2R      -R.V....KE...KYQH-WRW...............GWRWGTMLLGMLM-.CS.ATEKLWV--Y-----    44
D_ELI        -R.A....RGIERNCQNWWKW...............GI....MLLG-LMT.CS.AADNLWV--Y-----    43
C_MVP5180    -T.VT...MKVMKKNNR-SW................SL....Y-AMALL-PCLSYS-CL-A--YS----    45
O_ANT70      -I..VTMKAME.KRN.---W................TL....YLAMAL-TPCL.-LRCL-A--YA----    44
SIVcpzGAB1   -K.V....MEKKKR......DWNS........LSIIT...I-TI-LLTPCL.TSE.LWV--Y-----    43
SIVcpzANT    -R.K..........PIHI-W............GL....ALLIQF-E.KG.TNE.D-V--------    35
A_ROD        -M.N..........QL-I..............AI....-LASACLV.Y..C.T.---V-------T    31
B_EHO        -AHV........NNYL--..............TLLLIS-.YG.YMGKNFV------I-A          34
SIVAGMVER3   -K.L..........TL-I..............GI....-LIG--VV.LN.T.RQ-WV--------    33
SIVSYK173    -A.A..............FRTYIVCLFSLISLGF..............ME-Q--V-----I-H      34

SIVRCM       WRNSTVPMFCVTDNTQ.......SWGTLNCIP.EG.GISP.EVSI.NVS.ERFDAW..NNS..LYEQAKD    69
A_U455       -KDAVTTL--AS-AKAYDAEVHNV-A-HA-V-...TDPNPQ.-IDLV--T.-E-NM-..K-N.MV.D-MHE   104
B_HXB2R      -KEA-TTL--AS-AKAYDTEVHNV-A-HA-V-...TDPNPQ.--VLV--T.-N-NM-..K-D.MV.--MHE   106
D_ELI        -KEA-TTL--AS-AKSYETEAHNI-A-HA-V-...TDPNPQ.-IALE--T.-N-NM-..K-N.MV.--MHE   105
O_MVP5180    -EEAAPVL--AS-ANLTSTEQHNI-ASQA-V-...TDPNPH.-FPLG--T.DN--I-..K-Y.MV.D-MHE   107
O_ANT70      -EDA-PVL--AS-ANLTSTEKHNI-ASQA-V-...TDPTPY.-YPLH--T.DD-NI-..K-Y.MV.--MQE   106
SIVcpzGAB1   -HDADPVL--AS-AKAHSTEAHNI-A-QA-V-...TDPSPQ.--FLP--I.-S-NM-..K-N.MV.D-MHE   105
SIVcpzANT    ---A-PTL--A-NASMTSTEVHNV-A-TS-V-...IDPDPI.V-RL.-T-..VW-N-Y.-K-Y.MV.-SMTE   96
A_ROD        -K-A-I-L--A-R.NR.....D.T---IQ-.L..PDNDDYQ-ITL.--T.-A----........TVT---IE    85
B_EHO        -K-ASI-L--A-R.NR.....D.T---VQ-.L..PDNDDYT-IQL.-IT.-A----..D-..TWTD--TK    88
SIVAGMVER3   -K--S-QA--M-PT-R.....L-A-T-S.I..PDDHDYT--PL.-IT.-P-E--ADR-P.LV.A--GS    89
SIVSYK173    -EDAYA-L--T-SHKG.......G-A-K--V-SA....DQI--RV.-ITG-Y-P--...-S-HMIRQ-ILE   90

SIVRCM       NVWNLYDSTLKPCVRLSPLCITMNCSAINGS.......WDGIPTSAPPTTTKTTT.......QRTIGVEKE   146
A_U455       DIIS-W-QS-----K-T---V-LD-HN-T.........INNT.NNNTNI-DGV..................   147
B_HXB2R      DIIS-W-QS-----K-T---VSLK-TDLK.........NDT.N.TNSSSGRM.I.................   148
D_ELI        DIIS-W-QS-----K-T---V-L---DELR........NN-T.M.GNNV--....................   146
O_MVP5180    DIIS-WEQS----EKMTF--VQ---VDLQ.........TNKT.GLLNE-IN....................   148
O_ANT70      DIIS-W-QS-----QMTF--VQ-E-TN-A.........GT.T.N...........................   139
SIVcpzGAB1   DIIS-W-QS-----K-T---V-LQ--KA-F-.....QAKNLT.NQTSSPPL....................   150
SIVcpzANT    DM.Q-FQQSH----K-T-M--K---TGY..........N-.T.PT.TT-S--TS-VTPK.TTTP.......   144
A_ROD        D--H-FETSI----K-T---VA-K--STES-TG.NNTTSKST.S.TTT--PTDQEQEI..SED-PCARAD   150
B_EHO        D--S-FETSI----K-T---V--K-NKTWS-......ASKET.-.TSSASLRSS-QTLL.NEDSKCIQND   149
SIVAGMVER3   -IHL-FEQ------K------K-S-VEL-S-EPTTTPKST.T.A-TTNI-AS---LPCVQNKTSTVL-SC   157
SIVSYK173    DMSA-FLQANR---K-A-M--R-L-TLD..........NSP.A.TSTP--SPP-TPP..NETW......   139

SIVRCM       CTAGNETCEEVQDADVMSCEFAVAGLKRDEKHKYNDTWYSRDLWCEKETNSTNSTKKK..CFVRHCNTTS   214
A_U455       ......EEMK...N-S-NMTTEL--K-Q-VYSLF-RL-IVQI.D....NNS....YRLIN---ST         198
B_HXB2R      ....M-K....GEIK..N-S-NISTSI-GKVQ-EYAFF-KL-IIPI.D.-D....TTS..YKLTS---SV    200
D_ELI        .....-E....KGMK..N-S-N-TTVLK-K-QQVYALF-RL-IVPI.D.-DSS.-NSTN.YRLIN---SA    201
O_MVP5180    .............EMR..N-S-N-TTVLT-K-EQKQALF-VS--SKVND.SNA..VNGTT.YMLTN--S-I   200
O_ANT70      ......E....NLMK..K---N-TTVIK-K-E-KQALF-VS--MEL.NET-STNKTNSKMYTLTN--S-T   196
SIVcpzGAB1   .............EMK..N-S-N-TTEL--K-KQVYSLF-VE-VVNL.G.-E....NNT.YRIIN----A    198
SIVcpzANT    .....IV....DGMKLQE-N-NQSTGFK-K-Q-MKAIF-KG--MKCQD.-N.....ETNC.YYLW-----T    199
A_ROD        NCS-LGE....EETI..N-Q-NMT--E--K-KQ--E----K-VV--TN.....NQTQ.-YMN----SV    209
B_EHO        SC--IGL....EEMI..D-Q-KMT------SKQ-K-----KQ--V---G-R-....NESK.-YIKT---SI    208
SIVAGMVER3   NETII-KELNEEP-S...N-T--M---YV--Q-K---SVV-NDAEIM-K-G..-N....SNRE.-YMI---DSV   219
SIVSYK173    .WGD-S-....EPRF..N-S-NLT-GFK-K-QQ-RAFF-KD--MK-EG.......NSSY.YYLL----SV    194

SIVRCM       IQQFCEPKYWEPFRLRYCAPPGFALLVCKDKNYTGF.DTCVNVTATSCTHMINTTVASGFGL.NGSINVN   282
A_U455       -T-A-PKVSF--IPIH----A---I-K---PEFN-K.GP-R--STVQ---G-KPV-STQLL-.---LAER    266
B_HXB2R      -T-A-PKVSF--IPIH----A----I-K--NN-TFN-T.GP-T--STVQ---G-T-STQLL-.---LAEE    268
D_ELI        -T-A-PKVSF--IPIH----A----I-K-R--KFN-T.GP-T--STVQ---G-RPV-STQLL-.---LAEE    269
O_MVP5180    -K-A-PKVSF--IPIH----T-Y--IFK-N-TDFN-T.GL-H--ISVVT---G-KP--STQLI-.---TLSRE    268
O_ANT70      -T-A-PKVSF--IPIH----A----I-K-F-NSTEFN-T.G--R-I-VVT---G-RP--STQLI-.---TLSKG    264
SIVcpzGAB1   -T-A-PKTSF--IPIH----A----I-K-N--DFS-K.GK-T--STVH---G-KPV-TTQLLI.---LAEG    266
SIVcpzANT    -T-S--KSTF--IPIH----A-Y-I-R-E-EDF-V.GM-K--SVVH---G-SPM--TWLL-.--T.YQT    266
A_ROD        -TES-DKH--DAI-F-------Y---R-N-T--S--APN-SK-V-ST--R.MME-QT-TWFGF--TRAE-    278
B_EHO        --ES-DKH--DSL-F-------R-N-TK--S--MPN-SK-VVS.LYR.MME-QT-TWFGF--TRAE-    276
SIVAGMVER3   -KEA-DKT--DEL------A-----K-N-YD-A--KTN-S--SVVH--NL-----TT-LL-.---YSE-    288
SIVSYK173    -SAA--KQTFQ--PIQ------YS--K-N-T-FE-D.-V-T----V---QEF--LASTW-Q-.--TYKAK    262
```

Figure 2A

```
SIVRCM         ETWIYQRRQSNR..TVIG.LNSFY.NLSVTCRRPSN...RTVKGISL..ATGVF.I.S...LR......        331
A_U455         -IR-RSENFT-NAK-I-VQ-VNP...VKIN-S--Y-TRKNIR.RY-I..GS-QAFYVT...GK.I....        321
B_HXB2R        -VV-RSVNFTDNAK-I-VQ--TS...VEIN-T--N-...N-R-R-RIQRGP-RAF.VT...IG.K.....        322
D_ELI          -VI-RSENLT-NAKNI-AH--ES...VKI--A--YQ...N-RQRTPI..GL-QSLYTTR..S-SI.....        324
O_MVP5180      KIR-MGKNITESAKNI-VT--TP...INM--I-EGI...AE-QD-YT..GPMRWRSMTLKRSN.N....        324
O_ANT70        KIRMMAKDILEGGKNI-VT---T....-NM--E--QI...DIQ.EMRI..GPMAWYSM.G.IGG.T....        317
SIVcpzGAB1     NITVRVENK-KNTDVW-VQ-VEA...V-LN-H--G-...N-RGEVQI..GP-MTFYNI...EN.V....        319
SIVcpzANT      N-SVVMNGR.KNESVLVR.FGKEFE--TI--I--G-.....-RNLQI..GP-MTFY.N....VE.IA...        320
A_ROD          R-Y--WHGR.DN.R-I-S..--KY-...--LH-K--G-...KI--Q-M-..MS-HVFHSH...YQ.P....        330
B_EHO          R-Y--WHGR.DN.R-I-S.---Y-..--TMH-K--G-...KM-VP-RT..VS-IL.F.H...SQ.P....        326
SIVAGMVER3     R-Q--W-KHRVSN.DS-LVLF-KH-...-T---K--G-...K--LPVTI..MA-LV.F.H...SQ.R....       340
SIVSYK173      DKVRFIKQKDKNESVI-LVPEALR...QII-E--G-...ESI-N-Q-..-A-....YF.....-F.VIQGKL      317

SIVRCM         .VEKRPKGAWCRFEG.NWTDAWKEVKERVKT...TKGYRGT...SNTD...KIKIRTVYGGDDEARYFWL       390
A_U455         .IG.DIRQ-H-NVSRRD-NRTIQQ-A...EQ.L...KKKFN...NK-....I-FASSS.---I-ITTHSF       374
B_HXB2R        .IG.NMRQ-H-NISRAK-NNTL-QIA...SK.L...REQFGN..NK-....I-FKQSS.---P-IVTHSF       376
D_ELI          .IG....Q-H-NISRAQ-SKTLQQ-A...RK.L...-TLL....NK-I....IKFKPSS.---P-ITTHSF      374
O_MVP5180      .TSP-SRV-Y-TYNKTV-EN-LQQTAI-YLN.L...VNQTE...NV-....I-FS--S.---A-VSHLHF      381
O_ANT70        .AGNSSRA-Y-KYNATD-GKIL-QTA--YLE.........LV..N--GSINMTFNHSS.---L-VTHLHF      374
SIVcpzGAB1     .-G.DTRS-Y-KIN-TT-NRTVE----..-A.L...ATSS....NR-AA.NITLN-AS.---P-VTHHMF       374
SIVcpzANT      .TG.DTRK-F-TVNKTL-EQ-RNKTE...HV.L...AEHWKKVDNK-NAKTIWTFQD...--P-VKVH-F      378
A_ROD          .IN----RQ---W-K-.K-K--MQ----TLAKHP...R-----..ND-R..NISFAAPGK-S-P-VA-M-T      390
B_EHO          .IN----Q---W-K-....-E-IQ----TI-NHP...R-S--T..NISQ...IRLAEHARSS-P-V--M-T      386
SIVAGMVER3     .YNT-LRQ---H-Q-..--RG------NEIVK.LPKDR-Q-....ND-E...E-YLQRL.F--P--ANL-F      400
SIVSYK173      KTGRDA-R-F--VT-.----EFF-Q-H...EQ.A...TKTWK...NV-....NTTW-SQP--L-V-TH-F       372

SIVRCM         NCNGEFLYCKLNWFLN.LLN..NETVGT..........TNEK......RKAPFVPCITKMIVNDWYTVS        440
A_U455         --G---F--NTSGLF-.SIW..-GSMS........ND.MGP........NGTITLC-RI-Q-I-M-QR-G      424
B_HXB2R        --G---F--NSTQLF-.STWF.-S-WS-E....GSNN.-EG........SDTITL--RI-Q-I-M-QK-G      431
D_ELI          --G---F--NTSGLF-.STW..-ISAW.......NNI-ESNN....STNTNITLQ-RI-Q-IKMVAGRK       429
O_MVP5180      --H---F--NTSGMF-.YTFI.-C-KSGCQEIKGSN...ET........N-NGTI--KLRQL-RS-MKGE      438
O_ANT70        --H---F--NTAKMF-.YTFSC-G-TCS......VSN.VSQ........GNNGTL--KLRQV-RS-IRGQ      428
SIVcpzGAB1     --G---F--NTSQIFTD......-I-.............NGIIIL--RIRQ--SS-MR-G                415
SIVcpzANT      --Q---F--DITPWF-.ATYTG-LI..............T........NG-LIAH-RI-Q---H-GI--       424
A_ROD          --R------NMT----.WIE...-K-..............HRNYA--HI-Q-I-T-HK-G                432
B_EHO          --R------NMTF----.WVE...-R-.............G.......L-RNYAS-HIRQ---T-HKIG       430
SIVAGMVER3     --Q---F---MD----.Y-..-R--DPDH..NPCNG.-KG-GKAPGPCAQRTY-A-HIRSVI-----L-       464
SIVSYK173      Q-G---F--NVSKLFA.NIT..-GNAS........KNN.YA........SNLRLS-AIRQ-I---RY-R       421

SIVRCM         RKVYTPPRPDALKCSAQVSYLLADIDYIND.SETN...ITLSA...EVGDYWAAELGRYKAIEIRPIGFAP      504
A_U455         QAM-A---IQGVIR-ESNITG--LTR-GG.T.NN-K.NE-FRPGGGDMR-N-KS--YK--VVK-E-L-V--      491
B_HXB2R        KAM-A---ISGQIR--SNITG--LTR-GG.NSNNES..EIFRPGGGDMR-N-RS--YK--VVK-E-L-V--      498
D_ELI          .AI-A---IERNIL--SNITG--LTR-GGIN.NS--..E-FRPGGGDMR-N-RS--YK--VVQ-E-L-V--      495
O_MVP5180      SRI-A---I-GN-T-HSNITGMILQL-QP.W.NS-G.EN--RPVGGDMK-I-RTK-YN--VVQ-K-FSV--      505
O_ANT70        SGL-A---IKGN-T-MSNITGMILQM-NT.W.NSS-MNV-FRPIGGDMK-I-RT--FN--VVRVK-FSV--      496
SIVcpzGAB1     -GI-A---IRGNIT-NSNITG--LTS-TPVT.KNSG.NL-FRPTGGNMK-I-RS--YK--VVR-E-LSV--      483
SIVcpzANT      KGI-LA--RGNVS-TSSITGMILE...GQIYN-....VKV-P.AAR-A-Q-R--S---QVV--.-LSV--      486
A_ROD          -N--L---EGE-S-NST-TSII-N--WQ-N.NQ-----..F--.EVAE.L--.RL---D--LV--T----      496
B_EHO          -N--L---EGE-S-NST-TS-I-N--W-DK.NL--....-V---.EVSE.L--.KL---D--LV--T----      494
SIVAGMVER3     --T-A---EGH-Q-TST-TGMSVELN-NSK.NR--...V----P...QIETI---------LV--T----      528
SIVSYK173      KLI-L---TAGHI--TSN-TAV-T--E-YPG.-TL-.....FTPTANVE.-V-R-D-FN--L-Q-K-----      485

SIVRCM         TEIKRYQT......KQKRVPL.VLG..FLGFLSAAGTAMGAAATALTVQSRHLLAGILQQQKNLLDIVKR      565
A_U455         -RA--RVVE......RE--AV..G--AI-----G--ST----SIT----A--Q--S--V---S--RAIEA     554
B_HXB2R        -KA--RVVQ......RE--AV..GI-AL-----G--ST----SMT----A-Q--S--V---N--RAIEA      561
D_ELI          -RA--RVVE......RE--AI..G--AM-----G--ST---RSVT----A-Q-MS--V---N--RAIEA      558
O_MVP5180      -KMS-PIINIHTPHRE-AV..G--ML--V-----ST----------RTHSV-K--V---D--RAIQA        573
O_ANT70        -R-A--PVISTR.THRE--AV..G--ML--V-----ST------T-A--THT--K--V---D--RAIQA      563
SIVcpzGAB1     -KAR--HTVARQ.KDR--AAF.G--AL-----G---ST------VT----A-Q--S--V---N--KAIEA     551
SIVcpzANT      -T.---PEIKQH...SR---GI..GI-LF---L-----ST----SI---A-T-N-.H--V---A---QAIET   550
A_ROD          -KE----SSAH...GRHT-GVF.....AT--S-----SLTVSA--T-----V---QQ---V---          560
B_EHO          -S----SSVT....PRN--GV-.....AT--S----SLT-SA---T-----V---QQ-V-V---           558
SIVAGMVER3     --VR--TGGH...DRT--..F-........G---------------Q----------------AA-EA       592
SIVSYK173      -DQR--ELPN...TRE--AAPLA----...-L---------G------L--QT-----V---QK--EA-EA    550
``` gp120 ← | → gp41

Figure 2B

```
SIVRCM       QQNLLKLTVWGTKNLQARVTAIEKYLADQSLLNTFGCAWRQVCHTVVPWTFNKT.................    619
A_U455       --H--------I-Q-----L-V-R--Q--Q--GIW---SGKLI-T-T----..-SSW...SNKSQE.......    613
B_HXB2R      --H--Q-----I-Q----IL-V-R--K--Q--GIW---SGKLI-T-A----..-ASW...SNKSLE.......    620
D_ELI        --H--Q-----I-Q----IL-V-R--K--Q--GIW---SGKHI-T-N----..-SSW...SNRSLN.......    617
C_MVP5180    --H--R-S---IRQ-R--LQ-L-TLIQN-QR--LW---KGKLI-Y-S-K-...-TSW...SGRYNDD......    633
O_ANT70      --Q--R-S---IRQ-R--LL-L-TL-QN-Q---SLW---KGKL--Y-S-K-...-R-WI.GNES.........    620
SIVcpzGAB1   --H--Q-SI--V-Q----LL-V-R--Q--QI-GLW---SGKA--Y-T----..-NSWPGSNST.D........    611
SIVcpzANT    --H--Q-S---V-Q----ML-V----S--Q--SLW---DKVT---T----...NSW..VNFTQTCAKNSSD    616
A_ROD        --E--R-------------------Q--AR--SW---F-------V.-DS........LA............    615
B_EHO        --E--R-------------------K-AQ--SW---F-------T---V.-ES........LK.........    613
SIVAGMVER3   --QM----I--V---N-----L----E--AR--AW----K-----T---QW-NR........T.........    647
SIVSYK173    --H--G-----V--N--L--T--R--AI-SNW---FK-I----A-T-E..KACGNNSNFCPK..........    612

SIVRCM       ..PEWQKESWLQWERNISYLEANITIALQEACDQHEKNVHELEKLSNWGDAFSWLNLDWWMQYIKIGFFI    687
A_U455       ..DI-NNMT-----KE---SYTGI-YQLIE-S-N-Q----ELD-LA-DK-ANL.N-F-ISN-LW--RLFVI-  680
B_HXB2R      ..QI-NHTT-ME-D-E-NNYTSL-HSLIE-S-N-Q----EQ--LE-DK-ASLWN-F-ITN-LW----LFIM-  688
D_ELI        ..EI--NMT-ME---E-DNYTGL-YSLIE-S-T-Q----EK--LE-DK-ASLWN-FSITQ-LW----FIM-   685
C_MVP5180    ..SI-DNLT-Q--DQH-NNVSSI-YDEI-A----Q----KA-LE-DE-ASLWN-FDITK-LW----AII-    701
O_ANT70      ...I-DTLT-QE-D-Q---NISST-YEEI-K--V-Q-QEKK-LE-DE-ASIWN--DITK-LW----AII-    687
SIVcpzGAB1   ..DI-GNLT-Q--DKLV-NYTGK-FGL-E---S-Q----ERD-LE-DQ-ASLWN-FDITK-LW----FLMA   679
SIVcpzANT    IQCI-ENMT-QE-D-LVQNSTGQ-YNI---I-HE-Q-R-KK--YE-DK-SSLWN-FDITQ-LW----FIM-   686
A_ROD        ...D-DNMT-QE--KQVR------SS-EQ--I-Q----MY--Q--NS-DIFGN-FD-TS-VK--QY-VL-   683
B_EHO        ...D-NNMT-Q----QVRF-D----KL--E---I-Q----MY--Q--NQ-DIFSN-FDFTS--A--RL-LY-  681
SIVAGMVER3   ...D-NNMT--E---Q-----G---TQ-E--RA--E----LDAYQ---S-S-FW--FDFSK-LNIL----LD  715
SIVSYK173    ...Q-KNMT-HR--QEVDN-TDH-DGL-R----E-Q-R---D-T---QE-DSLW--FD-SK-FF-L----YV  680

SIVRCM       VIGIIGLRVAWLLWNCLSNLRQGYRP.LSPP.SYVQQIHIHN.TGE.PQTPGEKREDGGEEGGNKYNNWL    753
A_U455       -G-L-----IVFTVLSIINRV----S-.-F.......-TLAPI.PEG.LGR--RIE-E---Q-KDRSIRL.   740
B_HXB2R      -G-LV----IVFAVLSIVNRV----S-.--F.......T-LPT.PRG.-DR-EGIE-E---R-RDRDRSIRL. 748
D_ELI        IG-L-----IVFAVLSLVNRV----S-.--F.......-TLLPA.PRG.-DR-EGTE-E---R-RDRSVRL.  745
O_MVP5180    -GAL--I--IMIIL-LVK-I----Q-.--L.........-PVPH.RQ-.AE---RTG-E---GDRP-WTAL.  761
O_ANT70      -GALV-V--IMIVL-IVK-I----Q-.--L.........-PN-H.QE-.AG---RTGGG-----RPRWIPS.  747
SIVcpzGAB1   -G------IIMTVFSVVRRV----S---L......-TL-PV.QR-.QGRL--ID-G---QDRSRVRL.     739
SIVcpzANT    -GA-V---ILLV-VS--RKV----H-.--F.......-PTQ-.QQD.-EQ-E-I---E--RKDRIRWRAL.  746
A_ROD        IVAV-A---IVIYVVQM--R--K----VF-S-PG-I------K.DRGQ-ANEE.TE----SN--DR-WP-P  751
B_EHO        ----VV--I-IYIIQM-AR--K----VF-S-F--T---P-RK.DRGQ-ANEE.TE-G--NNE-YRSWP-Q   749
SIVAGMVER3   -L-------LLYTVYS-IARV----S-.-...........P.WKGQ-DNAE.GPGE--DKRK-SSEP-Q    776
SIVSYK173    IGALVL--LVSFSVGIIK--LG--V-I-QN......PTQGRK.DPGK-ADEE........-GS-DREGLN.   735

SIVRCM       REYC.................WI..QLIHPLSRIWTQLSQICR....SCSS.IIFQSLRWILAKIQ..     795
A_U455       VS.G.................FLA-AWDDLRN-CLFSYHRLRDFA....L.IV.ARAVE-LGRSSLKGLR    786
B_HXB2R      VN.G.................SLALIWDDLRS-CLFSYHRLRDLL....L.IV.TRIVE-LGR.......    787
D_ELI        LN.G.................FSALIWDDLRS-CLFSYHRLRDLI....L.IA.VRIVE-LGR.......    784
O_MVP5180    PP.G.................FLQQLYTDLRTIILWTYH-LSNLI....-GIRRL-DYLGLGLWI..LGQ    807
O_ANT70      PQ.G.................FLPLLYTDLRTIILWTYH-LSNLA....-GIQKV-SYLRLGLWI..LGQ    793
SIVcpzGAB1   V-.G.................CLPLIWDDLRN-GIWSY-SLTSLA....C.NV.WRQLKTLGH-ILHSLR    785
SIVcpzANT    QH.G.................FFALLWVDLTSIIQWIY-ICRT-L....L.NL.WAVLQHLCR.ITFRLC    791
A_ROD        IA-I.................HFL-.R---RL-T.RLYSICRDLL....-R-F.LTL-LIYQN......L   791
B_EHO        I--I.................HFP-..RQLRD-LIWLYSGCRTLL....-KTF.QTL-PVLQP.......   788
SIVAGMVER3   K-SGTAEWKSNWCKRLTNWCSISS-..........WLYNSCLTLLVHLR..AF.QYI-YGLGE-KA.AAQ   833
SIVSYK173    VS.T.................FSRE-.....SLRQSLEAGQ-......WRTVCSSFRSLIR-LT        770

SIVRCM       .............YGWQEF.KE.FSSWFAEMALQNAYYTWR.GL.CAVARDFAGWPAMVCRRIRQGLER    847
A_U455       LGWEGLKYLWNLLL-...WG.R-LKI-AITLLDAVAVAVAGWIDRVIEIGQTIGRAILNIP---------    852
B_HXB2R      RGWEALKYWWNLLQ-...WS.Q-LKN-AVSLLNATAIAVAEGTDRVIE-VQGACRAIRHIP---------    853
D_ELI        RGWDILKYLWNLLQ-...WS.Q-LRN-ASSLFDAIAIAVAEGTDRVIEIIQRACRAVLNIP---------    850
O_MVP5180    KTIEACRLCGAVMQ-...WL.Q-LKN-ATNLLDTIVASVANWTDGIILGLQRIGQGFLHIP------A--    873
O_ANT70      KIIINVCRICAAVTQ-...WL.Q-LQN-ATSLLDTLAVAVANWTDGII-GIQRIGTGIRNIP--------    859
SIVcpzGAB1   LLRERLCLLGGIIQ-...WG.--LKI-AISLLDATAIAVAEGTDRIIEAFQVTLRIIRNIP---------    851
SIVcpzANT    NHLENNLSTLWTIIR......T-.....IIKNIDRLAIWVGEKTDSILLALQTIVRIIRE---------I   851
A_ROD        RDWLRLRT..AFLQ--CEWI.Q-..AFQAA-RATRETLAGAC-....WR-LERIGRGILA-P------A-I  855
B_EHO        .....LRLPPAYLR--ISW-.Q-..AIQAA-RA-GETLASAA-.TS.WG-L-RA--EIIAIP------A-L  849
SIVAGMVER3   ...EAVVALARLAQN...AGYQI...............WLAC-SAYRAIINSP--V-----G          874
SIVSYK173    ITWGFIS........--F....N-LKIAAASLGREIRDWVAAIWQAIY-AT-RVVEAV-ALP--L-----I   829

SIVRCM       LCN  850
A_U455       ALL  855
B_HXB2R      ILL  856
D_ELI        SLL  853
O_MVP5180    ILV  876
O_ANT70      SLL  862
SIVcpzGAB1   ALL  854
SIVcpzANT    AL-  854
A_ROD        ALL  858
B_EHO        ALL  852
SIVAGMVER3   IL-  877
SIVSYK173    YL-  832
```

Figure 2C

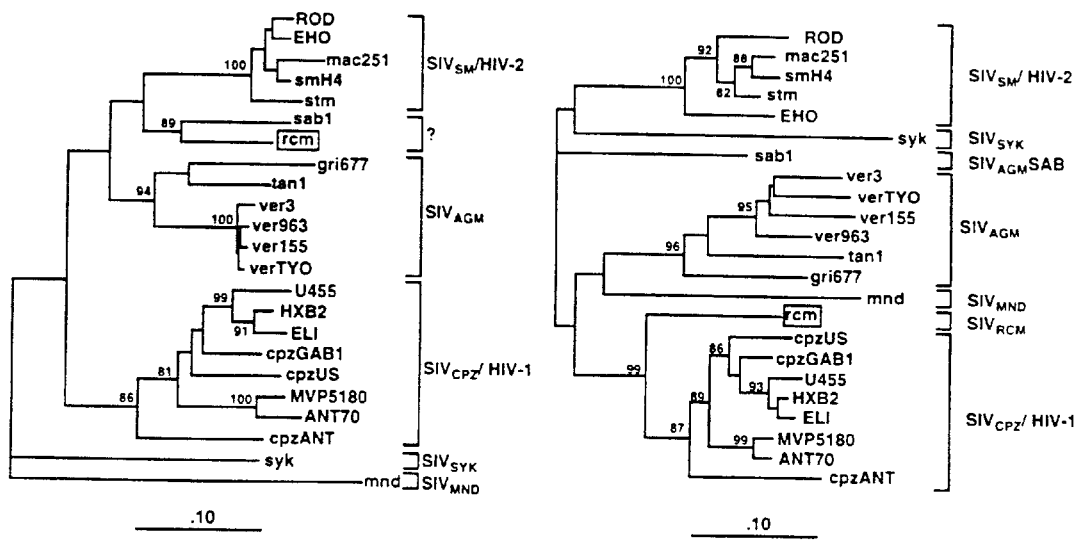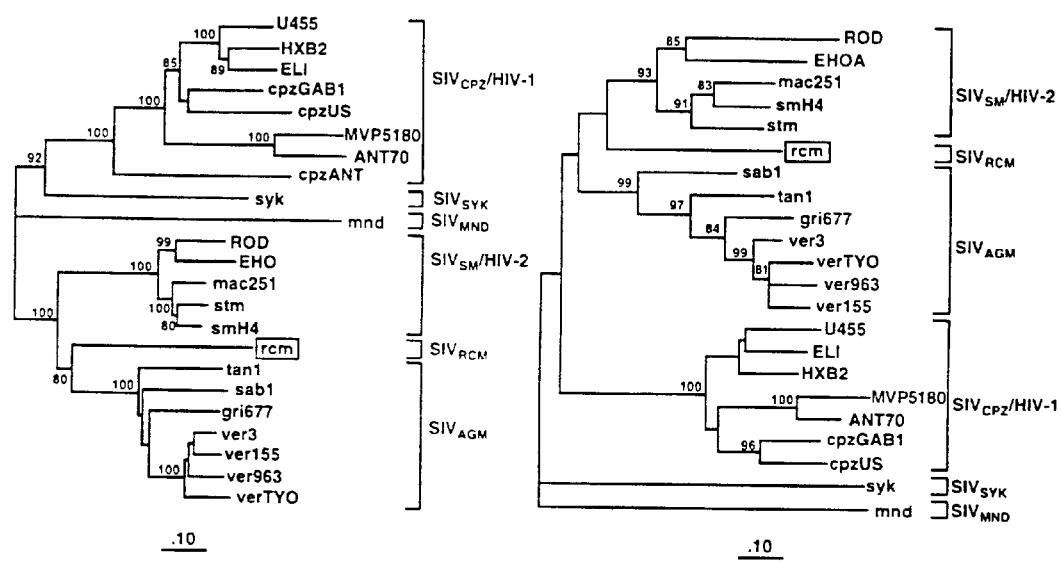
Figure 5

```
                            location of splice donor
                  first exon of rev    |        extended rev orf
SIVsmPbj     MSS..NEEELRRRLRLIHLLHQT SKYGMSWESAAYRALAIKCFRDLLCS...ICNSILWYTSMEECDSSPLLCNQE*
SIVsmM9      ---..----------F----   -------------------..------C---------------K*
SIVsmH4      ---..T---------F----   ---------------S----..------C---------N---------*
SIVmac142    -R-HTG--------------   ----L--K-----H--S--LW---Y-...--H-L--C-----L----N---------*
SIVmac251    ---HER-----K--------   ------------H--F--LW---Y-...--H-L-C---L----N---------*
SIVmac239    --NHER-----K--------   ------------H--F--LW---Y-...--H-L--C---L----N---------*
SIVmac1a11   ---HER-----K--------   ------------H--F--LW---Y-...--H-L--C---L----D---------*
SIVmac132zm  --NHER-----K--------   ------------H--F--LW---YP..--H-L--C---L----N---------*
SIVmacSTM    --D..Q-----K-----QF---- ----LP-K-T----Y-----LL---H-..V-HG---C-------D---------*

HIV2/FO784   --QAEK-----------Y----- -H-V------T--N----Y-F-I----..V-H------R--K--NT---R--K*

HIV2/BEN     --ERAD--G-QGK---LR-----  E--AW*---VCCHFTN--LLSI-*P..V-DCF--H-RV-K-IY-LI---*K*
HIV2/CAM2    -TERAD--G-Q-K----R-----  E--AWQK----CHSTS*-LLNI-QTT.--DCF--R-RV-K-IH------*K*
HIV2/EHO     -NA..R-RD-QKG---L------  E--TC**LPTCYTP-Y-YLWVYGQE..L-HCL----F--K-IN-----Y-KQ
HIV2/GH1     -HEKADG---QE-----R-----  E*DVW*--TMCCQ--S*-LLSI-HP...--DCF--RARV-K-IH------*KQ
HIV2/KR      -NGRAD--G-Q-KQ---R-----  E-NG**K--NCCHFTN*-LLNI-RP..--DCF--H-RV----IH-------K*
HIV2/MDS     -NERAD--G-Q-K----R-----  E-DAQNA----CHFTN*-LLNI-QTTT--CF--H-RV---IH-------K*
HIV2/NIHZ    -TERAD--G-Q-K----R-----  E-EG**--T-DCYCTS*-LPNT-QA..--DCF-RH-RV---IH--V----K*
HIV2/ROD     -NERAD--G-Q-K----R-----  E-D...------CHFIS*-LLSI-HP..--CF--..-HV-K-NH-------K*
HIV2/SBL1SY  -TERAD--GV--K----R-----  E-NEW*N---CCLS-N*-LLNI-HQ..--DCF--S-RV-K-IH------*K*
HIV2/ST      -NERAE-------K----R----  E*DVW*--TICCQ--S*-LLNI-RP..--DCF--RARV-K-IH------*K*
HIV2/UC1     -TT..R-KD-QKG---L------  E--TH*Q-PV-F-PTY--LWVSGS*EKL-HCL--H-C---RNG-S----HKQ
```

Figure 7

SIVrcm

TGGCGCCCGAACAGGGACTTGAGAGTGGCTGAGAGACCTCCGAGGCTAAG

GTTCGGCGCGGCAGGTCACCGCGGGAGTGGAACCTTGACCAGGTAAGAGC

TGCCTGGTGGCTTCAAAGTGCTAGAGAAAGTGAGCTAGCGAAGGAAGCAG

GGCAACCCGGTCCGGTACTGGGCCTCTAGGGAAGGAGCGAAGTCCTAGAG

AAGGGAGGAAAATGGGTGCGAGAGCCTCATTGTTGTCAGGGAAGAAGCTA  ⟶ GAG start

GACGCATGGGAATCAGTTAGGTTACGGCCCGGCGGGAAAAAGAAATACAT

GCTGAAGCATTTGGTATGGGCATGCAAAAACTAAATAAATTTGGCTTGA

GTGATCATTTGTTAGAAACAGCAACAGGATGTGAAAAAATATTAGGAGTC

CTGCTGCCTCTAGTTCCGACAGGGTCAGAGGGGCTAAAAAGCCTCTTTAA

TTTGTGCTGCGTACTCTGGTGCGTACACAAGGAAGTGAAAGTGAAAGACA

CAGAGGAAGCTGTAGCAAAAGTGAAAGAATGCTGCCATCTAGTGGAAAAA

GCAGAAAATACAACAGAAAAGAAAGGGAGCAACAGCGCCACCTAGTGG

ACAAAGAGGAAATTATCCTATAATTACTATAAATCAGCAGCCTGAGCATA

ATCCTATATCACCAAGGACTCTAAATGCCTGGGTCAAGGTGGTAGAGGAG

AAAAAATTCTCAGCAGAAGTAGCGCCCATGTTCTCGGCACTATCAGAAGG

CTGCATACCCTATGATATAAATCAAATGCTAAATGCCATAGGGGAACACC

AGGGTGCGCTGCAGATAGTAAAGGAAGTGATCAATGAGGAAGCAGCAGAC

TGGGATGCTAGACATCCAGTACCAGGCCCGATACCAGCAGGGCAACTTAG

AGAACCAACAGGAAGTGACATAGCAGGGACAACTAGCTCAATAGCAGAAC

AGATAGCTTGGACCACCAGAGCAAACAACCCCATTAATGTGGGCAATCTG

TACAGAAATTGGATAATAGTAGGGTTACAAAAATGGGTAAAAATGTACAA

TCCAGTGAACATCCTAGATATAAAGCAAGGACCAAAAGAGTCATTCAAGG

ATTATGTGGATAGATTTTATAAAGCCTTGAGAGCAGAACAGGCAGACCCG

Figure 8A

```
GCAGTAAAAAATTGGATGACACAATCACTGCTGATACAAAATGCTAACCC

AGACTGTAAAATGGTACTCAAGGGTCTGGGAATGAACCCTTCTTTAGAAG

AAATGCTAACAGCCTGTCAGGGGGTAGGAGGACCCCAGCATAAAGCTCGG

GTACTAGCAGAGGCCATGCAAATGATGCAAAGTAATATCATGGCTCAGCA

ATCAGCAAACAGGGGGCCTCCAAGAAGATCAGGAGGAAATCCAAATTTAA

GATGTTACAATTGTGGTAAGCCAGGACACATTTCTAGATATTGTAAAGCC

CCTAGAAGGAAGGGATGCTGGAAATGTGGATCCCCAGACCATCTCTTGAA
                                    ┌─> POL start
AGACTGCACAAAGCAAATAAATTTTTTAGGGAGACTCCCCTGGGGTCAGG

GGAAGCCGAGGAACTTTCCTTTGACTTCCTTGACTCCCTCTGCTCCAGGG

ATGGAGAGCAATTACGACCCTGCAGAAGAGATGCTAAAGAATTATCTGAG

GAGGGCAGGGGAACAAAAGAGACAACAGAGGCAGGAAGAGAGCAAGAAGA

GAGAGGGAGCATATCAGGAAGCCTTAACCTCCCTCAATTCGCTCTTTGGA
             GAG stop <─┐
AGCGACCAACTACAATAGCTCAAATAGAAGGGCAGAAAGTGGAGGTCCTA

TTAGACACAGGAGCAGATGACACAGTAATTGAAGGAATAGAATTAGGAAA

TGATTGGACCCCAAAAATAATAGGAGGAATAGGGGGATATATTAATGTAA

AACAATATAAAAACTGTGAAATTGAAATAGCTGGAAAAAGGACTCATGCT

CATGTGCTAGTGGGACCAACACCAGTGAATATTATAGGGAGAAATGTTTT

AAAGAAATTAGGAGCCACACTAAATTTTCCAATAAGCCAAATAGAAACTA

TAAAGGTAGAATTAAAGTCTGGACAAGATGGACCACGAGTAAAACAATGG

CCATTGTCAAAAGAAAAAATAGAAGCTTTAACAGAAATTTGCAATGCAAT

GGAGAAGGAAGGAAAAATTTCAAAAATAGGGCCAGAAAACCCCTACAACA

CACCAATATTCTGTATTAAAAGAAAGACTCCACAAAATGGAGAAAATTG

GTAGATTTTAGAGAACTAAATAAGAGAACACAGGACTTTTTTGAGGTGCA

GCTGGGAATACCACATCCAGGAGGATTAAAGCAATGTGAGAGAATAACGG
```

Figure 8B

```
TATTAGACATCGGGGATGCATATTTTTCATGTCTTCTGTATGAGCCTTTT

AGGAAATATACTGCATTTACAATACCAGCAGTAAATAATCAAGGACCAGG

AGTGAGGTATCAATATAATGTGCTGCCTCAGGGATGGAAGGGATCTCCCG

CCATCTTTCAGGCATCAGCCAATAAGATCTTACAGCCATTTAGGGAAGAG

AATCCAGATGTCATCATTTACCAGTACATGGATGATCTCTTTGTAGGCTC

AGATAGAACAAAGTTGGAACATGACAAATGATCAAACAATTAAGAGATC

ATCTACTGTTCTGGGGCTTTGAGACCCCAGACAAAAATTTCAGGATAAA

CCTCCATATTTGTGGATGGGGTATGAGCTGCACCCAAAAAGTTGGACAGT

ACAGGAGATCAAGTTACCAGAGAAGAAGAATGGACAGTTAACGATATTC

AGAAATTAGTAGGAAAGTTAAACTGGGCAAGTCAAATTTACAGTGGGCTA

AGGACTAAGGAATTGTGCAAGTTGATAAGGGGAGCAAAAGCATTAGATGA

AAAAGTAGAAATGACAAAAGAAGCAGAAATAGAATATGAAGAAACAAGA

TGATTCTAAAAGAAAAGTTGCATGGGGTGTATTATGATGAAAAGAAACCC

TTAGTGGCAAACATTCAGAAGTTAGAAGGTGGACAGTGGTCCTATCAAAT

AGAACAGGAGTCAGGAAAACCACTGAAAACAGGCAAATATGCTAAGCAGA

AAACAGCACACACCAATGAAATTAGAATGCTGGCAGGGTTAGTACAAAAA

ATTGCAAAAGAAGCCATAGTTATTTGGGGAAGGCTGCCAACATTCAGACT

GCCAATAGAGAGAGAGGTATGGGACTAATGGCGGTCCCAATACTGGCAGG

TTACCTGGATACCAGATTGGGAATTTGTTAGCACACCACCTCTTATTAGA

CTCGGGTACAACCTAGTTAAGGATCCCATACCAGGAGAGGAAGTCTACTA

TGTGGATGGGGCAGCTAACAGAAATAGTAAATAGGAAAGGCGGGATATG

TTACAAATAGAGGAAAGAAAGGTAAAGAATTAGAAGAAACTACTAAT

CAAAAGCAGAATTAGAAGCAGTATTACTGGCATTAAAAGATTCAGGGCC
```

Figure 8C

```
TAAAGTAAACATAGTCACAGATTCACAGTATGTTTATGGAATTCTAGAAG

CACAACCAGATACTAGTGACTCAGGGTTAGTGACAGAAATTATAAATCAG

ATGATAGGGAAGAAGCAGTGTACCTTTCCTGGGTGCCCGCACATAAGGG

CATCGGAGGAAATGAGGAAGTAGATAAATTAGTTAGTAAAGGAATCAGAC

AGGTACTGTTCCTAGATGGGATAGAAAAGCACAAGAAGAACATGAAAAG

TATCATAATAATTGGAGAGCATTGGCAGAAGATTTTCAAATTCCACAAAT

AGTGGCAAAAGAAATAGTAGCACAGTGTCCAAAATGTCAAGTAAAAGGGG

AAGCAATCCATGGGCAAGTGGATGCAAGTCCAGGGACTTGGCAAATGGAC

TGCACACATTTGGAAGGAAAAATAATCATAGTAGCAGTCCATGTGGCAAG

TGGATATATAGAGGCAGAAGTAATACCAGCAGAAACAGGAAAAGAGACAG

CACATTTCCTGTTGAAACTAGCAGCAAGATGGCCAGTAAGGAAGCTACAC

ACAGATAATGGAGCAAATTTCACAAGTGCAGCAGTACAGGCGGTCTGCTG

GTGGGCTCAGATAGAGCACGCCTTTGGAGTACCTTACAATCCTCAAAGTC

AAGGAGTAGTGGAAAGCATGAATAAACAATTAAAAATAATCATAGAACAA

GTAAGAGAACAAGCAGAAAATTAGAAACAGCAGTCCAAATGGCAGTTTT

GGTTCACAATTTTAAAGAAAGGGGGGATTGGGGGGTACAGTGCAGGAG

AAAGAATAATAGATATAATAGCAACAGACTTAGCAACCAATAAATTACAA

AATCAAATTTCAAAAATTCAAAATTTTCGGGTTTATTACAGAGAAGGAAG

GGATCAACTGTGGAGAGGTCCAGCTAAGCTGATCTGGAAAGGAGAAGGAG

CAGTAGTCATCCAGGAGGAGACTGGAGACTTGAAGGTAGTCCCCAGGAGA
                              ┌─► VIF start
AAAGCAAAAATCATAAAAGAATATGGCAGAAAAGATGTGGATAGTGAGGC
              POL stop ◄─┐
CAATTTGGCGGGTAGACAGGAGGAAAATTGAACAATGGCACTCTTTGGTA

AAATATCATCAGTACAAGGAAAGAAAGCAGCAAAAGAGTGGGAGTATGT
```

Figure 8D

GCCTCACTTTAAAGTACCATGGGGATGGTGGTCGCATTCAGAAGTTCACA

TACCTTTAGAGGAAGGATCAAAGTTAAAATAACCACCTATTGGAATTTG

ACAGTAGAAAAGGGATGGCTAGGGACATATGGGGTAGGAATCTTATGGAT

AAAAGGAGATTATGTAACAGATGTATTTCCTTGGACTGCAGATAGTTTAA

TACATAAAATTTATTTTCCATGTTTTACAGATAGAGCAATCAGACAAAGT

CTACTAGGGGAAAAGTTCTAGTGTGTGCCTTCCAAGGGGACATAGAGA

TCAGGTAGGGACTCTGCAATTTTTGGCAATACAAGCGTGGGCTAAAAGTC

⮕ VPX start
AGTTAGATAGGTATGGCAGAAAGAGCCCCCGAGGTCCCCACTGGGGCTGG

AGAAGCAGAGTTCCAGCCTTGGCTACGGGACATGCTAGAAAAGGTCAACT

TGGAAGCCAGGTTACACTTTCATCCAGAGTTCATTTTCCGTCTGTGGCGC

VIF stop ⬅
ACTTGTGTGGAACACTGGCATGACGTACATCAGAGAAGTTTAGAATATGC

TGCTTATAGGTACTTACTGCTGATGCAAAAGGCTTTGTTTATCCACTGTC

AGACAGGGTGTAGTCAGAGACATGGACCCAATCCTAGGGCAGTAGGAGAA

VPX stop ⬅                                        ⮕ VPR start
AGGATAACCATCCTACCGGGGATGTAATGATGGCCCTCTCTTTACAGAGA

TGGAGCTGCCCCCTGAGGATGAAGGTCCGCAACGAGAACCTTATGATGAA

TGGTTAATGGATACCCTAATAGAGTTGCAAGAAGAAGCTAAGAAACATTT

TACATATGCTTTGCTAACGCAAATAGGAGATTATGTATATGAGCAACATG

GGGATAGCATAGAGGGAGTGCAGGCAATGATTCGGCTGCTTCAAAGAGCC

⮕ TAT first exon start
TTGTTTCTTCATTTTAGAAATGGATGTGCAGGGAGTAGGATTGGAACATC

CAGAGGAAGTAATCCTCTACGATCCATTCCGCAAACGAGAAACATCATGT

VPR
stop ⬅
AACACTTGTTATTGTAAAAAATGTTGTTATCACTGCCAACTCTGCTTCCT

⮕ REV first exon start
GCAGAAAGGACTAGGCATAAATTATGCTTCCAGGGCAAGACGAAGAAGAT

TAT and REV first exon stop ⬅
CTAAGGAAGAAAATAAGGCTGATAAATTTCCTGTACCTAATCAGTAAGTA

TGGAGTGCCCTGGACTAGTACTGCTTTTAGAGCCTCAGCTAAAAAGGTTT

Figure 8E

```
TTATAGATCTTTTAGTTACAATAATTAAAGGAAAATAGAATAAGATAAGA    ENV start
TGGATAAGAAATTAGTAATAGTATTAATAGTAGTAATAGGGATAATACTA
GTACAAGGATCACAAAAACCGCAATATATAACAGTCTTCTATGGTGTCCC
AGTATGGAGAAACAGCACAGTGCCTATGTTTTGTGTGACTGATAATACTC
AATCATGGGAACTCTAAATTGTATACCAGAGGGAGGAATATCTCCAGAG
GTTTCAATAAATGTGTCAGAACGATTTGATGCTTGGAATAATAGCTTATA
TGAACAAGCAAAAGATAATGTGTGGAATCTTTATGATTCCACTCTAAAAC
CATGTGTCAGATTAAGCCCATTATGTATTACCATGAATTGTTCAGCAATA
AATGGTAGCTGGGATGGAATCCCTACCTCAGCACCACCAACAACAACAAA
AACAACAACACAAGAACTATAGGTGTAGAAAAGGAATGTACTGCTGGCA
ACGAAACATGTGAGGAAGTTCAGGATGCAGATGTGATGTCTTGTGAATTT
GCTGTAGCAGGACTAAAGAGAGATGAGAAACACAAGTATAATGATACCTG
GTATTCTAGAGACCTTTGGTGTGAAAAGGAAACAAATTCTACAAATTCTA
CAAAAAGAAATGTTTTGTAAGGCACTGCAATACAACTTCCATACAACAA
TTTTGTGAACCAAAGTACTGGGAACCATTTAGGTTAAGATATTGTGCTCC
ACCAGGGTTTGCCTTACTGGTCTGCAAAGATAAAAATTATACAGGCTTTG
ATACCTGTGTTAATGTTACTGCCACTTCATGCACACATATGATTAATACT
ACTGTGGCCTCAGGGTTTGGATTAAATGGATCAATTAATGTAAATGAGAC
TTGGATATATCAGAGAAGGCAAAGTAATAGGACAGTTATAGGTCTCAATA
GTTTTTATAATTTGTCAGTAACATGCAGGAGACCTTCAAATAGAACAGTG
AAAGGGATATCGCTAGCAACAGGAGTCTTTATCTCACTAAGAGTAGAGAA
GAGACCAAAAGGAGCTTGGTGTAGATTTGAAGGGAATTGGACGGATGCAT
GGAAAGAAGTAAAAGAGAGAGTGAAAACAACAAAAGGGTATCGAGGTACT
```

Figure 8F

```
AGTAACACAGACAAAATAAAGATAAGAACAGTATATGGTGGAGATGATGA

GGCAAGATATTTCTGGCTAAATTGTAATGGAGAATTTTTATATTGCAAGT

TAAATTGGTTTTTAAATTTGTTAAATAATGAGACAGTAGGGACAACAAAT

GAGAAGAGAAAAGCACCTTTTGTACCATGCATCACAAAAATGATAGTCAA

TGATTGGTATACAGTATCGAGGAAGGTATACACGCCACCGAGGCCAGATG

CGTTAAAGTGCAGTGCACAGGTATCCTATCTGTTGGCAGACATAGACTAT

ATTAATGACAGTGAGACAAACATCACCCTCTCAGCGGAAGTGGGTGATTA

TTGGGCAGCAGAATTGGGGAGATATAAGGCAATAGAAATCAGACCAATTG

GCTTTGCACCAACAGAAATAAAAAGGTACCAGACGAAACAGAAAAGGGTA

CCTTTGGTGCTGGGTTTTCTAGGTTTCCTCTCAGCAGCAGGTACTGCAAT

GGGCGCAGCGGCGACAGCCCTGACTGTCCAGTCCCGGCATTTGCTTGCAG

GGATATTGCAGCAGCAAAAGAACCTGCTGGACATAGTTAAGCGGCAGCAG

AATCTGCTAAAGCTCACCGTCTGGGGAACTAAAAATCTCCAGGCGCGTGT

CACTGCTATTGAGAAATACCTAGCAGACCAATCTCTATTGAATACATTTG

GGTGTGCCTGGAGACAAGTCTGCCATACAGTGGTGCCGTGGACATTCAAC

AAAACGCCTGAGTGGCAGAAAGAATCATGGTTGCAGTGGGAAAGAAATAT

CTCTTATTTAGAGGCTAACATTACAATAGCATTACAGGAGGCCCAGGATC

AACATGAGAAAAATGTGCATGAATTGGAGAAATTAAGTAATTGGGGAGAT

GCATTCAGTTGGCTGAATCTTGACTGGTGGATGCAATATATAAAAATAGG

CTTCTTTATAGTAATAGGTATCATAGGATTAAGAGTAGCTTGGCTGTTAT
```
                                                 → TAT and REV second exon start
```
GGAATTGTCTTAGTAATCTTAGGCAAGGGTATAGGCCTCTCTCCCCACCC

TCTTATGTTCAGCAGATCCATATCCACAACACGGGGGAACCGCAAACTCC

AGGAGAAAAAGAGAAGACGGTGGAGAAGAAGGTGGCAACAAGTACAACA
```
TAT second ←┐
exon stop
```
ATTGGCTGAGAGAATATTGCTGGATTCAACTGATCCACCCGTTGAGCAGG
```

Figure 8G

```
ATTTGGACGCAGCTATCGCAGATTTGCAGAAGCTGCAGCTCAATAATCTT
        REV second exon stop ←┐      ┌→ NEF start
CCAGAGCCTCCGGTGGATTTTAGCTAAGATACAATATGGGTGGCAAGAGT

TCAAAGAATTCAGCAGCTGGTTTGCTGAGATGGCGCTTCAAAATGCTTAC

TACACCTGGAGAGGGTTATGTGCGGTGGCACGAGACTTTGCTGGATGGCC

AGCCATGGTGTGCAGAAGGATCAGGCAGGGCCTCGAGAGACTTTGTAATT
ENV ←┐
stop ←┐
      AGAGGAGGCATTACAGCAGAAACGCAAGCTTCAATAGATGACATTGACTG

GTATGAAGATACTGATGACACCTTGGTAGGATTTCCAGTGAAACCTCAAG

TACCACTTAGACCAATGAGTTACAAGCTAGCAATAGACATGTCTCACTTT

TTAAAAGAAAAGGGGGGACTGGAAGGGATTTATTGGAGTATCAGAAGACA

AAGAATATTGGATATGTACCTGGAAAATGAGCATGGCATAATACCTGATT

GGCAAAACTACACTCCAGGGCCAGGAATAAGATATCCAACACTGTTTGGA

TGGCTCTGGCAATTGGTGCCAGTAGATGTATCTGATGAAGCAAGAGAAGA

TGAAGAGCATAGTTTGCTACATCCAGCAGAAACAAGTGGGATGGAAGACC

CATGGGGGGAGGTCTTGGCCTGGAAGTTTAATCCTATGCTGGCAGTAGAT

TACATAGGCTATAGACTGCATCCAGAGTTCTTTGGGGAAAGGAAGAACAA
    NEF stop ←┐
GACCCAGTAACCACATCCTCTGGGGTTGCCTTGGTAACCAGGCAGAAGAA

TCTGCTGATGCAAAAGGGACTTTCCACTGGTGCATGCGCACTGGGGAAGG

GACTTTCCGGGATGACGTGGGAGGGGGAGTGGTCAGCCCTCTCCTGCTGC

ATATAAGCAGCTGCTCTGCGCTTGTAAAACGGGTCTCTCCCTGGGAGGCT

ACCGGATTGAGCCTGGGTGTTCTCTGGTAAGTCTCTAGGAACTCCAGCTT

GAGCCTGGGTGTTCGCTGGTGTCTCTGAACAGGCTTGCTGGGGTGCCTCT

CGCTCTTCGGGTAGACCGCCAGTTGAGGCTCGGCCGGCCTCAACGGGAGA

GATCACCGCTTGCTTATAGCCTTGAAGCTCAATAAAGCATGCCAGTTAGT

TTACTGTAAGCAAGTGTGTGCCTGTTTTACCTCTCAGCAGTTAACGACTC
```

Figure 8H

TGGGGTAGGGATCCCTCAGATTCTTGTGGCAGAAGAGCCTTGGGCTAAGA

AAATTCCCTACCAGT

Figure 8I

SIVRcm_gag
MGARASLLSGKKLDAWESVRLRPGGKKKYMLKHLVWACKKLNKFGLSDHLLETATGCEKILGVLLPLVPT
GSEGLKSLFNLCCVLWCVHKEVKVKDTEEAVAKVKECCHLVEKAENTTEKEKGATAPPSGQRGNYPIITI
NQQPEHNPISPRTLNAWVKVVEEKKFSAEVAPMFSALSEGCIPYDINQMLNAIGEHQGALQIVKEVINEE
AADWDARHPVPGPIPAGQLREPTGSDIAGTTSSIAEQIAWTTRANNPINVGNLYRNWIIVGLQKWVKMYN
PVNILDIKQGPKESFKDYVDRFYKALRAEQADPAVKNWMTQSLLIQNANPDCKMVLKGLGMNPSLEEMLT
ACQGVGGPQHKARVLAEAMQMMQSNIMAQQSANRGPPRRSGGNPNLRCYNCGKPGHISRYCKAPRRKGCW
KCGSPDHLLKDCTKQINFLGRLPWGQGKPRNFPLTSLTPSAPGMESNYDPAEEMLKNYLRRAGEQKRQQR
QEESKKREGAYQEALTSLNSLFGSDQLQ

Figure 9

SIVRcm_pol
FFRETPLGSGEAEELSFDFLDSLCSRDGEQLRPCRRDAKELSEEGRGTKETTEAGREQEERGSISGSLNL
PQFALWKRPTTIAQIEGQKVEVLLDTGADDTVIEGIELGNDWTPKIIGGIGGYINVKQYKNCEIEIAGKR
THAHVLVGPTPVNIIGRNVLKKLGATLNFPISQIETIKVELKSGQDGPRVKQWPLSKEKIEALTEICNAM
EKEGKISKIGPENPYNTPIFCIKKKDSTKWRKLVDFRELNKRTQDFFEVQLGIPHPGGLKQCERITVLDI
GDAYFSCLLYEPFRKYTAFTIPAVNNQGPGVRYQYNVLPQGWKGSPAIFQASANKILQPFREENPDVIIY
QYMDDLFVGSDRTKLEHDKMIKQLRDHLLFWGFETPDKKFQDKPPYLWMGYELHPKSWTVQEIKLPEKEE
WTVNDIQKLVGKLNWASQIYSGLRTKELCKLIRGAKALDEKVEMTKEAEIEYEENKMILKEKLHGVYYDE
KKPLVANIQKLEGGQWSYQIEQESGKPLKTGKYAKQKTAHTNEIRMLAGLVQKIAKEAIVIWGRLPTFRL
PIEREVWDWRSQYWQVTWIPDWEFVSTPPLIRLGYNLVKDPIPGEEVYYVDGAANRNSKIGKAGYVTNRG
KEKVKELEETTNQKAELEAVLLALKDSGPKVNIVTDSQYVYGILEAQPDTSDSGLVTEIINQMIGKEAVY
LSWVPAHKGIGGNEEVDKLVSKGIRQVLFLDGIEKAQEEHEKYHNNWRALAEDFQIPQIVAKEIVAQCPK
CQVKGEAIHGQVDASPGTWQMDCTHLEGKIIIVAVHVASGYIEAEVIPAETGKETAHFLLKLAARWPVRK
LHTDNGANFTSAAVQAVCWWAQIEHAFGVPYNPQSQGVVESMNKQLKIIIEQVREQAEKLETAVQMAVLV
HNFKRKGGIGGYSAGERIIDIIATDLATNKLQNQISKIQNFRVYYREGRDQLWRGPAKLIWKGEGAVVIQ
EETGDLKVVPRRKAKIIKEYGRKDVDSEANLAGRQEEN

Figure 10

SIVRcm_vif
MAEKMWIVRPIWRVDRRKIEQWHSLVKYHQYKGKKAAKEWEYVPHFKVPWGWWSHSEVHIPLEEGSKLKI
TTYWNLTVEKGWLGTYGVGILWIKGDYVTDVFPWTADSLIHKIYFPCFTDRAIRQSLLGEKVLVCAFQGG
HRDQVGTLQFLAIQAWAKSQLDRYGRKSPRGPHWGWRSRVPALATGHARKGQLGSQVTLSSRVHFPSVAH
LCGTLA

Figure 11

SIVRcm_vpx
MAERAPEVPTGAGEAEFQPWLRDMLEKVNLEARLHFHPEFIFRLWRTCVEHWHDVHQRSLEYAAYRYLLL
MQKALFIHCQTGCSQRHGPNPRAVGERITILPGM

Figure 12

SIVRcm_vpr
MELPPEDEGPQREPYDEWLMDTLIELQEEAKKHFTYALLTQIGDYVYEQHGDSIEGVQAMIRLLQRALFL
HFRNGCAGSRIGTSRGSNPLRSIPQTRNIM

Figure 13

SIVRcm_tat
MDVQGVGLEHPEEVILYDPFRKRETSCNTCYCKKCCYHCQLCFLQKGLGINYASRARRRRSKEENKADKF
PVPNHRSISTTRGNRKLQEKKEKTVEKKVATSTTIG

Figure 14

SIVRcm_rev
MLPGQDEEDLRKKIRLINFLYLITDPYPQHGGTANSRRKKRRRWRRRWQQVQQLAERILLDSTDPPVEQD
LDAAIADLQKLQLNNLPEPPVDFS

Figure 15

SIVRcm_env
MDKKLVIVLIVVIGIILVQGSQKPQYITVFYGVPVWRNSTVPMFCVTDNTQSWGTLNCIPEGGISPEVSI
NVSERFDAWNNSLYEQAKDNVWNLYDSTLKPCVRLSPLCITMNCSAINGSWDGIPTSAPPTTTKTTTQRT
IGVEKECTAGNETCEEVQDADVMSCEFAVAGLKRDEKHKYNDTWYSRDLWCEKETNSTNSTKKKCFVRHC
NTTSIQQFCEPKYWEPFRLRYCAPPGFALLVCKDKNYTGFDTCVNVTATSCTHMINTTVASGFGLNGSIN
VNETWIYQRRQSNRTVIGLNSFYNLSVTCRRPSNRTVKGISLATGVFISLRVEKRPKGAWCRFEGNWTDA
WKEVKERVKTTKGYRGTSNTDKIKIRTVYGGDDEARYFWLNCNGEFLYCKLNWFLNLLNNETVGTTNEKR
KAPFVPCITKMIVNDWYTVSRKVYTPPRPDALKCSAQVSYLLADIDYINDSETNITLSAEVGDYWAAELG
RYKAIEIRPIGFAPTEIKRYQTKQKRVPLVLGFLGFLSAAGTAMGAAATALTVQSRHLLAGILQQQKNLL
DIVKRQQNLLKLTVWGTKNLQARVTAIEKYLADQSLLNTFGCAWRQVCHTVVPWTFNKTPEWQKESWLQW
ERNISYLEANITIALQEAQDQHEKNVHELEKLSNWGDAFSWLNLDWWMQYIKIGFFIVIGIIGLRVAWLL
WNCLSNLRQGYRPLSPPSYVQQIHIHNTGEPQTPGEKREDGGEEGGNKYNNWLREYCWIQLIHPLSRIWT
QLSQICRSCSSIIFQSLRWILAKIQYGWQEFKEFSSWFAEMALQNAYYTWRGLCAVARDFAGWPAMVCRR
IRQGLERLCN

Figure 16

SIVRcm_nef
MGGKSSKNSAAGLLRWRFKMLTTPGEGYVRWHETLLDGQPWCAEGSGRASRDFVIRGGITAETQASIDDI
DWYEDTDDTLVGFPVKPQVPLRPMSYKLAIDMSHFLKEKGGLEGIYWSIRRQRILDMYLENEHGIIPDWQ
NYTPGPGIRYPTLFGWLWQLVPVDVSDEAREDEEHSLLHPAETSGMEDPWGEVLAWKFNPMLAVDYIGYR
LHPEFFGERKNKTQ

Figure 17

GenBank Accession No. AF028608

SIVrcm gag gene, partial deduced amino acid sequence

```
  1 KYMLKHLVWA CKKLNKFGLS DHLLETATGC EKILGVLLPL VPTGSEGLKS LFNLCCVLWC
 61 VHKEVKVKDT EEAVAKVKEC CHLVEKAENT TEKEKGATAP PSGQRGNYPI ITINQQPEHN
121 PISPRTLNAW VKVVEEKKFS AEVAPMFSAL SEGCIPYDIN QMLNAIGEHQ GALQIVKEVI
181 NEEAADWDAR HPVPGPIPAG QLREPTGSDI AGTTSSIAEQ IAWTTRANNP INVGNLYRNW
241 IIVGLQKWVK MYNPVNILDI KQGPKESFKD YVDRFYKALR AEQADPAVKN WMTQSLLIQN
301 ANPDCKMVLK GLGMNPSL
```

Nucleotide sequence

```
  1 aaatacatgc tgaagcattt ggtatgggca tgcaaaaaac taaataaatt tggcttgagt
 61 gatcatttgt tagaaacagc aacaggatgt gaaaaaatat taggagtcct gctgcctcta
121 gttccgacag ggtcagaggg gctaaaaagc ctctttaatt tgtgctgcgt actctggtgc
181 gtacacaagg aagtgaaagt gaaagacaca gaggaagctg tagcaaaagt gaaagaatgc
241 tgccatctag tggaaaaagc agaaaataca acagaaaaag aaaagggagc aacagcgcca
301 cctagtggac aaagaggaaa ttatcctata attactataa atcagcagcc tgagcataat
361 cctatatcac caaggactct aaatgcctgg gtcaaggtgg tagaggagaa aaaattctca
421 gcagaagtag cgcccatgtt ctcggcacta tcagaaggct gcatacccta tgatataaat
481 caaatgctaa atgccatagg gaacaccag ggtgcgctgc agatagtaaa ggaagtgatc
541 aatgaggaag cagcagactg ggatgctaga catccagtac caggcccgat accagcaggg
601 caactcagag aaccaacagg aagtgacata gcaggacaa ctagctcaat agcagaacag
661 atagcttgga ccaccagagc aaacaacccc attaatgtgg caatctgta cagaaattgg
721 ataatagtag gttacaaaa atgggtaaaa atgtacaatc cagtgaacat cctagatata
781 aagcaaggac aaaagagtc attcaaggat tatgtggata gattttataa agccttgaga
841 gcagaacagg cagacccggc agtaaaaaat tggatgacac aatcactgct gatacaaaat
901 gctaacccag actgtaaaat ggtactcaag ggtctgggaa tgaacccttc ttta
```

Figure 18

GenBank Accession No. AF028607

SIVrcm pol gene, partial deduced amino acid sequence

```
  1 IPAETGKETA YFLLKLAARW PVRKLHTDNG ANFTSAAVQA VCWWAQIEHT FGVPYNPQSQ
 61 GVVESMNKQL KIIIEQVREQ AEKLETAVQM AVLVHNFKRK GGIGGYSAGE RIIDIIATDL
121 ATNKLQNQIS KIQNFRVYYR EGRDQLWXGP AKLIWKGE
```

Nucleotide sequence

```
  1 aataccagca gaaacaggaa aagagacagc atatttcctg ttgaaactag cagcaagatg
 61 gccagtaagg aagctacaca cagataatgg agcaaatttc acaagtgcag cagtacaggc
121 ggtctgctgg tgggctcaga tagagcacac ctttggagta ccttacaatc ctcaaagtca
181 aggagtagtg gaaagcatga ataaacaatt aaaaataatc atagaacaag taagagaaca
241 agcagaaaaa ttagaaacag cagtccaaat ggcagttttg gttcacaatt ttaaaagaaa
301 agggggggatt ggggggtaca gtgcaggaga agaataata gatataatag caacagactt
361 agcaaccaat aaattacaaa atcaaatttc aaaaattcaa aattttcggg tttattacag
421 agaaggaagg gatcaactgt gganaggtcc agctaagctg atctggaaag gtgaa
```

Figure 19

COMPLETE GENOME SEQUENCE OF A SIMIAN IMMUNODEFICIENCY VIRUS FROM A RED-CAPPED MANGABEY

*This work was funded by grants AI 38573-02; AI 27698-05; RO1 AI25291; and NO1 AI35170 from the National Institutes of Health. Therefore, the government may have certain rights in the invention.*

FIELD OF THE INVENTION

The present invention is in the field of virology. The invention relates to the nucleic acid sequence of the complete genome of the new simian immunodeficiency virus isolate from a red-capped mangabey, SIVrcm, and nucleic acids derived therefrom. The invention also relates to peptides encoded by and/or derived from SIVrcm nucleic acid sequences, and host cells containing these nucleic acid sequences and peptides. The invention also relates to diagnostic methods, kits and immunogens which employ the nucleic acids, peptides and/or host cells of the invention.

BACKGROUND OF THE INVENTION

Phylogenetic analyses of simian immunodeficiency virus (SIV) isolates reveal that they belong to five distinct lineages of the lentivirus family of retroviruses (47). These five SIV lentiviral lineages form a distinct sub-group because primate viruses are more closely related to each other than to lentiviruses from non-primate hosts (47). Importantly, only simian species indigenous to the African continent are naturally infected (4, 13, 28, 35). Thus far, natural SIV infections in Africa have been documented in the sooty mangabey (SM) (*Cercocebus torquatus atys*) (SIVsm strains), in Liberia (30), in Sierra Leone (4, 5), and the Ivory Coast (43); in all four sub-species of African green monkeys (agm) (*Cercopithecus aethiops*) (1, 21, 22, 25, 33, 34, 39) (SIVagm strains), in eastern, central and western Africa; in the Sykes monkey (syk) (*Cercopithecus mitis*) (SIVsyk strains) in Kenya (9); in the mandrill (mnd) (*Mandrillus sphinx*) (SIVmmd strains) (38, 50) in Gabon; and in chimpanzees (cpz) (*Pan troglodytes*) (SIVcpz strains) (19, 20, 41, 42) also from Gabon. Because these SIVs and their simian hosts are highly divergent from each other and widely distributed across Africa, it is believed that the SIV family evolved and established itself in African simians long before acquired immunodeficiency syndrome (AIDS) appeared in humans (4, 15, 18, 19, 21, 30, 37, 47).

One common characteristic among all SIVs is that none are associated with immunodeficiency or any other disease in their natural hosts (9, 13, 22, 28, 30, 35, 38). This finding is in marked contrast to AIDS, which occurs in humans and macaques infected with primate lentiviruses (2, 7, 8, 27, 35). This lack of disease in the natural SIV hosts may be an example of long-term evolution toward avirulence (16), which supports the hypothesis that SIV has infected African simians for a relatively long time.

Human AIDS is caused by two distinct primate lentiviruses, human immunodeficiency virus (HIV), types 1 and 2 (2, 7). Interestingly, the phylogeny of HIV is markedly different from SIV, because genetic analyses have shown that the human viruses do not represent separate sixth and seventh lineages of primate lentiviruses, but instead, are members of two of the five existing SIV lineages (37, 46). HIV-1 is in the HIV-1/SIVcpz group (19, 51) and HIV-2 belongs to the HIV-2/SIVsm family (18, 23). These phylogenetic data on the HIV-1 and HIV-2 lineages have long suggested separate simian origins for HIV-1 and HIV-2 (37, 46).

Molecular studies of naturally occurring SIVsm and HIV-2 strains from rural West Africa have provided convincing evidence for a simian origin of HIV-2. A close genetic relationship has been established between the HIV-2 D and E sub-types and SIVsm strains found in household pet sooty mangabeys in West Africa (4, 14, 15). Moreover, all six known subtypes of HIV-2, including a new subtype F (3), are found only within the natural range of SIV-infected sooty mangabeys in West Africa. No other area of Africa or of the world has all six known HIV-2 subtypes. Together, these data provide strong support for independent transmissions of SIVsm from naturally infected sooty mangabeys to humans.

In contrast, there is much less information to support a simian origin for HIV-1. Although SIVcpz is the closest relative to HIV-1, there are only a few isolates, thus raising questions as to the likely primate reservoir. Only three SIVcpz strains have thus far been identified (20, 41, 42, 51). The first one was isolated from a single, household pet chimpanzee in Gabon and was not part of a primate research colony (42). An additional SIVcpz strain was found in a captive chimpanzee which was wild caught in Zaire and thus likely infected in Africa (41, 51). Finally, PCR data suggested the existence of a third SIVcpz strain, again from a wild caught chimpanzee from Gabon (20). Thus, although based on limited data, the hypothesis that HIV-1 is derived from members of a larger SIVcpz lineage remains plausible. However, additional SIVs within the HIV-1/SIVcpz lineage must be found to better understand the origin of the HIV-1 family.

The present invention is based on the genetic characterization of a new SIV isolate from a red-capped mangabey (RCM), *Cercocebus torquatus torquatus*. This RCM was a household pet in Lambarene, Gabon, and was not part of a primate colony, a zoo, or a research facility. Analysis of the full-length sequence of the SIVrcm indicates that this virus is related to SIV from sooty mangabeys, albeit very distantly. Its genome organization contains a vpx gene which is unique to members of the SIVsm/HIV-2 lineage. There is also phylogenetic evidence that SIVrcm is a recombinant.

The SIVrcm sequence(s) described herein will permit the development of new serological screening assays for testing of SIVrcm infection of humans. Although such infections have not yet been documented, it should be noted that viruses from a second mangabey species (SIVs from sooty mangabeys) have crossed the species barrier and have yielded a new human AIDS virus (HIV-2). It is thus conceivable that SIVrcm is similarly infecting humans in Gabon and Cameroon. To test this possibility, strain specific reagents (antigens, polypeptides, etc.) are required to test for SIVrcm specific antibodies in people as a sign of viral infection. Such strain specific antigens can now be designed on the basis of the SIVrcm sequence(s) described herein.

If evidence is found that humans in Africa are infected with SIVrcm (regardless whether this infection is pathogenic or not), then new screening assays for the world's blood supply will have to be developed that specifically detect anti-SIVrcm antibodies or SIVrcm nucleic acids. SIVrcm sequences are necessary to design such strain-specific tests.

Additionally, the new sequences will permit the development of assays for screening of primates, such as those in the wild, in zoos, and in research facilities, for SIVrcm.

SUMMARY OF THE INVENTION

The present invention pertains to the isolation and characterization of the genomic sequence of SIVrcm, a new simian immunodeficiency virus identified from a Gabonese red-capped mangabey (RCM), and nucleic acids derived therefrom.

In particular, the present invention relates to nucleic acids comprising the complete genomic sequence of SIVrcm, as well as nucleic acids comprising the complementary (or antisense) sequence of the genomic sequence of SIVrcm, and nucleic acids derived therefrom.

The invention also relates to vectors comprising the nucleic acid genomic sequence of SIVrcm, as well as nucleic acids comprising the complementary (or antisense) sequence of the genomic sequence of SIVrcm, and nucleic acids derived therefrom.

The invention also relates to cultured host cells comprising the nucleic acid genomic sequence of SIVrcm, as well as nucleic acids comprising the complementary (or antisense) sequence of the genomic sequence of SIVrcm, and nucleic acids derived therefrom.

The invention also relates to host cells containing vectors comprising the genomic sequence of SIVrcm, as well as nucleic acids comprising the complementary (or antisense) sequence of the genomic sequence of SIVrcm, and nucleic acids derived therefrom.

The invention also relates to synthetic or recombinant polypeptides encoded by or derived from the nucleic acid sequence of the genome of SIVrcm, and fragments thereof.

The invention also relates to methods for producing the polypeptides of the invention in culture using the SIVrcm virus or nucleic acids derived therefrom, including recombinant methods for producing the polypeptides of the invention.

The invention further relates to methods of using the polypeptides of the invention as immunogens to stimulate an immune response in a mammal, such as the production of antibodies, or the generation of cytotoxic or helper T-lymphocytes.

The invention also relates to methods of using the polypeptides of the invention to detect antibodies which immunologically react with the SIVrcm virion and/or its encoded polypeptides, in a mammal or in a biological sample.

The invention also relates to kits for the detection of antibodies specific for SIVrcm in a biological sample where said kit contains at least one polypeptide encoded by or derived from the SIVrcm nucleic acid sequences of the invention.

The invention also relates to antibodies which immunologically react with the SIVrcm virion and/or its encoded polypeptides.

The invention also relates to methods of detecting SIVrcm virion and/or its encoded polypeptides, or fragments thereof, using the antibodies of the invention.

The invention also relates to kits for detecting SIVrcm virion, and/or its encoded polypeptides, wherein the kit comprises at least one antibody of the invention.

The invention also relates to a method for detecting the presence of SIVrcm virus in a mammal or a biological sample, said method comprising analyzing the DNA or RNA of a mammal or a sample for the presence of the RNAs, cDNAs or genomic DNAs which will hybridize to a nucleic acid derived from SIVrcm. Usually, when a completely complementary probe is used, high stringency conditions are desirable in order to prevent false positives. However, conditions of high stringency should only be used if the probes are complementary to target regions which lack heterogeneity. The stringency of hybridization is determined by a number of factors during hybridization and during the washing procedure, including temperature, ionic strength, length of time, and concentration of formamide, if any. The nucleic acid sequences used in probes should be unique to SIVrcm, i.e., the nucleic acid sequences should be absent from individual mammals not infected with SIVrcm.

The invention also provides diagnostic kits for the detection of SIVrcm in a mammal using the nucleic acids of the invention. In one embodiment, the kit comprises nucleic acids having sequences useful as hybridization probes in determining the presence or absence of SIVrcm RNA, cDNA or genomic DNA. In another embodiment, the kit comprises nucleic acids having sequences useful as primers for reverse-transcription polymerase chain reaction (RT-PCR) analysis of RNA for the presence of SIVrcm in a biological sample.

The invention further relates to isolated and substantially purified nucleic acids, polypeptides and/or antibodies of the invention.

The invention further relates to compositions comprising one or more of the nucleic acids, polypeptides and/or antibodies of the invention.

BRIEF DESCRIPTION OF THE FIGURES

FIG. 2. Alignment of amino acid sequences of env proteins of SIVrcm and other primate lentiviruses (SEQ ID NOS: 10–21). The homologies among the sequences are indicated by dashes. Sequences of amino acids which are uniquely present in the various polypeptides (as compared to the corresponding amino acids of the SIVrcm) are indicated by letters, i.e., the sequences themselves.

FIG. 5. Phylogenetic analysis of SIVrcm (SEQ ID NOS: 22–23) (A) gag; (B) pol (5' end); (C) env; and (D) nef genes. Phylogenies indicate discordant branching orders which strongly suggest a recombinant SIVrcm genome.

FIG. 7. Amino acid sequence alignment of the "extended rev ORF" in members of the HIV-2/SIVsm/SIVmac group (SEQ ID NOS: 24–44). The vertical line indicates the position of the splice donor, usually used to express the spliced versions of tat and rev, respectively. Stop codons are indicated as asterisks. All SIVsm/SIVmac strains as well as HIV-2/FO784 have an uninterrupted extended rev ORF.

FIG. 8. Nucelotide sequence of the SIVrcm genome (SEQ ID NO:1)

FIG. 9. Deduced amino acid sequence of the SIVrcm Gag protein (SEQ ID NO: 45).

FIG. 10. Deduced amino acid sequence of the SIVrcm Pol protein (SEQ ID NO: 46).

FIG. 11. Deduced amino acid sequence of the SIVrcm Vif protein (SEQ ID NO: 47).

FIG. 12. Deduced amino acid sequence of the SIVrcm Vpx protein (SEQ ID NO: 48).

FIG. 13. Deduced amino acid sequence of the SIVrcm Vpr protein (SEQ ID NO: 49).

FIG. 14. Deduced amino acid sequence of the SIVrcm Tat protein (SEQ ID NO: 50).

FIG. 15. Deduced amino acid sequence of the SIVrcm Rev protein (SEQ ID NO: 51).

FIG. 16. Deduced amino acid sequence of the SIVrcm Env protein (SEQ ID NO: 52).

FIG. 17. Deduced amino acid sequence of the SIVrcm Nef protein (SEQ ID NO: 53).

FIG. 18. Partial nucleotide sequence of SIVrcm gag gene and deduced amino acid sequence (SEQ ID NOS: 54–55).

FIG. 19. Partial nucleotide sequence of SIVrcm pol gene and deduced amino acid sequence (SEQ ID NOS: 56–57).

DETAILED DESCRIPTION OF THE INVENTION

Figure 1:
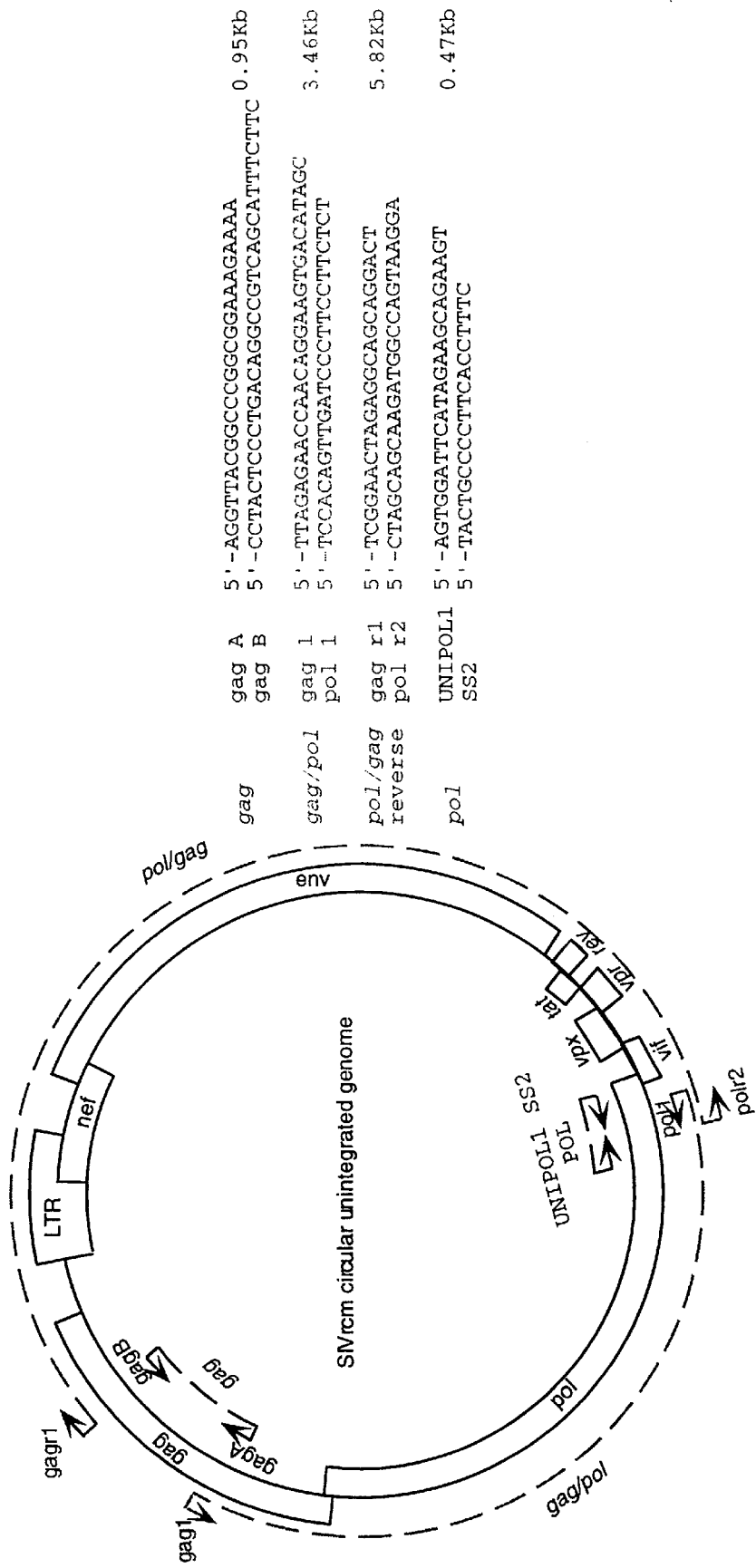
FIG. 1. PCR primer pairs (SEQ ID NOS: 2–9) and sequencing strategy.

The present invention relates to the determination of the nucleic acid sequence of the complete genome of SIVrcm, an isolate of simian immunodeficiency virus identified from a Gabonese red-capped mangabey (RCM) and nucleic acids derived therefrom. The nucleotide sequence of the SIVrcm is shown in the sequence listing as SEQ ID NO:1.

The phrase "derived from" is used throughout the specification and claims with respect to nucleic acids to describe nucleic acid sequences which correspond to a region of the designated nucleotide sequence. Preferably, the sequence of the region from which the nucleic acid is derived is, or is complementary to, a sequence which is unique to the SIVrcm genome. Whether or not a sequence is unique to the genome of SIVrcm can be determined by techniques known to those of skill in the art. For example, the sequence can be compared to sequences in databanks, e.g., GenBank, to determine whether it is present in the uninfected host or other organisms. The sequence can also be compared to the known sequences of other viral agents, including other retroviruses. The correspondence or non-correspondence of the derived sequence to other sequences can also be determined by hybridization under the appropriate stringency conditions. Hybridization techniques for determining the complementarity of nucleic acid sequences are well known in the art. In addition, mismatches of duplex polynucleotides formed by hybridization can be determined by known techniques, including for example, digestion with a nuclease such as S1 that specifically digests single-stranded areas in duplex polynucleotides.

Regions of the viral genome from which nucleic acid sequences may be derived include, but are not limited to, regions encoding specific epitopes as well as non-transcribed and non-translated sequences. Preferably, the epitope is unique to a polypeptide encoded by the SIVrcm genome. The uniqueness of the epitope may be determined by its degree of immunological cross-reactivity with other SIV viruses. Methods for determining immunological cross-reactivity are known in the art, e.g., radioimmunoassay and ELISA and other assays mentioned herein. The uniqueness of an epitope can also be determined by computer searches of known databases, e.g., for the polynucleotide sequences which encode the epitope, and by amino acid sequence comparisons with other known proteins.

The derived nucleic acid is not necessarily physically derived from the nucleotide sequence shown, but may be generated in any manner, including for example, chemical synthesis or DNA replication or reverse transcription or transcription, which are based on the information provided by the sequence of bases in the region(s) from which the nucleic acid is derived. The derived nucleic acid is comprised of at least 6–12 bases, more preferably at least 15–19 bases, more preferably at least 30 bases. The derived nucleic acid may also be larger, e.g., at least 100 bases in length, depending on the desired use of the nucleic acid. In addition, regions or combinations of regions corresponding to that of the designated sequence may be modified in ways known in the art to be consistent with an intended use. The derived nucleic acid may be a polynucleotide or polynucleotide analog.

The term "recombinant nucleotide" or "recombinant nucleic acid" as used herein intends a nucleic acid of genomic, cDNA, semisynthetic, or synthetic origin which, by virtue of its origin or manipulation: (1) is not associated with all or a portion of the nucleic acid with which it is associated in nature; and/or (2) is linked to a nucleic acid other than that to which it is linked in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA, as well as double- and single-stranded RNA. It also includes modified, for example, by methylation and/or by capping, and unmodified forms of the polynucleotide.

The present invention relates to nucleic acids having the entire genomic sequence of the SIVrcm isolate as shown in SEQ ID NO:1, as well as fragments (or partial sequences) thereof The invention also relates to nucleic acids having complementary (or antisense) sequences of the sequence shown in SEQ ID NO:1, as well as fragments (or partial sequences) thereof Partial sequences may be obtained by various methods, including restriction digestion of the complete sequence of SIVrcm, PCR amplification, and direct synthesis. Partial sequences may be all or part of the LTR and/or other untranslated regions of the SIVrcm genome, and/or all or part of the genes encoding the Gag, Pol, Vif, Vpr, Env, Tat, Rev, Nef and Vpx proteins and/or complementary (or antisense) sequences thereof Nucleic acids of the invention also include cDNA, mRNA, and other nucleic acids derived from the SIVrcm genomic sequence. Sequences of the LTRs and of the genes encoding Gag, Pol, Vif, Vpr, Env, Tat, Rev, Nef and Vpx are identified in FIGS. 9 to 17. Partial sequences of SIVrcm gag and pol genes and encoded amino acid sequence are shown in FIGS. 18 and 19. These latter sequences are available in GenBank, having Accession Numbers AF028608 and AF028607, respectively. Minor sequence variations between SEQ ID NO:1 and the pol gene of FIG. 19 are due to the fact that this partial pol gene sequence (in addition to the partial gag gene sequence) was obtained from a different clone of SIVrcm than that represented by SEQ ID NO:1.

The nucleic acids of the invention may be present in vectors or host cells in tissue culture or other media. The nucleic acids of the invention may also be isolated and substantially purified, by methods known in the art.

Nucleic acids of about 17 bases to about 35 bases in length are particularly preferred for use as primers in PCR amplification (see, e.g., the primers gag A and gag B (25 mer and 32 mer respectively)). Nucleic acids of about 14 to about 25 bases in length are particularly preferred for use in nucleotide arrays. (See, e.g., ref 80, which uses 20 to 25 mers).

The present invention also relates to vectors and host cells comprising the nucleic acids of the invention.

The present invention also relates to compositions comprising one or more of the nucleic acids, vectors, and/or host cells of the invention.

The present invention further relates to methods of using the nucleic acids, vectors, and/or host cells of the invention, and/or compositions thereof For example, the invention relates to the use of nucleic acids of the invention as diagnostic agents to detect the presence or absence of SIVrcm in a sample.

The present invention also relates to a method for detecting the presence of SIVrcm in a mammal using the nucleic acids of this invention.

In one embodiment, the detection method involves analyzing DNA of a mammal suspected of harboring SIVrcm. DNA can be isolated by methods well known in the art.

The methods for analyzing the DNA for the presence of SIVrcm include Southern blotting (63), dot and slot hybridization (60), and nucleotide arrays (see, e.g., U.S. Pat. Nos. 5,445,934 and 5,733,729).

The nucleic acid probes used in the detection methods set forth above are derived from the nucleic acid sequence shown in SEQ ID NO:1. The size of such probes is at least 10–12 bases long, more usually at least about 19 bases long, more usually from about 200 to about 500 bases, and often exceeding about 1000 bases.

The nucleic acid probes of this invention may be DNA or RNA. Nucleic acids can be synthesized using any of the known methods of nucleotide synthesis (see, e.g., refs. 54, 55, 58), or they can be isolated fragments of naturally occurring or cloned DNA. In addition, those skilled in the art would be aware that nucleotides can be synthesized by automated instruments sold by a variety of manufacturers or can be commercially custom ordered and prepared. The probes of this invention may also be nucleotide analogs, such as nucleotides linked by phosphodiester, phosphorothiodiester, methylphosphonodiester, or methylphosphonothiodiester moieties (67) and peptide nucleic acids (PNAs), in which the sugar-phosphate backbone of the polynucleotide is replaced with a polyamide or "pseudopeptide" backbone (68).

The nucleic acid probes can be labeled using methods known to one skilled in the art. Such labeling techniques can include radioactive labels, biotin, avidin, enzymes and fluorescent molecules (62).

The nucleic acid probes used in the detection methods set forth above are derived from sequences substantially homologous to the sequence shown in SEQ ID NO:1, or its complementary sequence. By "substantially homologous", as used throughout the specification and claims to describe the nucleic acid sequences of the present invention, is meant a high level of homology between the nucleic acid sequence and the sequence of SEQ ID NO:1, or its complementary sequence. Preferably, the level of homology is in excess of 80%, more preferably in excess of 90%, with a preferred nucleic acid sequence being in excess of 95% homologous with a portion of SEQ ID NO:1, or its complement. The size of such probes is usually at least 20 nucleotides, more usually from about 200 to 500 nucleotides, and often exceeding 1000 nucleotides.

Although complete complementarity is not necessary, it is preferred that the probes are made completely complementary to the corresponding portion of the SIVrcm genome, mRNA or cDNA target.

The probes can be packaged into diagnostic kits. Diagnostic kits may include ingredients for labelling and other reagents and materials needed for the particular hybridization protocol in addition to the probes.

In another embodiment of the invention, the detection method comprises analyzing the RNA of a mammal for the presence of SIVrcm. RNA can be isolated by methods well known in the art.

The methods for analyzing the RNA for the presence of SIVrcm include Northern blotting (66), dot and slot hybridization, filter hybridization (57), RNase protection (62), and reverse-transcription polymerase chain reaction (RT-PCR) (65). A preferred method is RT-PCR. In this method, the RNA can be reverse transcribed to first strand cDNA using a nucleic acid primer or primers derived from the nucleotide sequence shown in SEQ ID NO:1. Once the cDNAs are synthesized, PCR amplification is carried out using pairs of primers designed to hybridize with sequences in the genome of SIVrcm which are an appropriate distance apart (at least about 50 bases) to permit amplification of the cDNA and subsequent detection of the amplification product. Each primer of a pair is a single-stranded nucleic acid of about 20 to about 60 bases in length where one primer (the "upstream" primer) is complementary to the original RNA and the second primer (the "downstream" primer) is complementary to the first strand of cDNA generated by reverse transcriptions of the RNA. The target sequence is generally about 100 to about 300 bases in length but can be as large as 500–1500 bases or more, e.g., 9,000 bases. Optimization of the amplification reaction to obtain sufficiently specific hybridization to the SIVrcm nucleotide sequence is well within the skill in the art and is preferably achieved by adjusting the annealing temperature.

The amplification products of PCR can be detected either directly or indirectly. In one embodiment, direct detection of the amplification products is carried out via labeling of primer pairs. Labels suitable for labeling the primers of the present invention are known to one skilled in the art and include radioactive labels, biotin, avidin, enzymes and fluorescent molecules. The desired labels can be incorporated into the primers prior to performing the amplification reaction. Alternatively, the desired labels can be incorporated into the primer extension products during the amplification reaction in the form of one or more labeled dNTPs. In one embodiment of the present invention, the labeled amplified PCR products can be detected by agarose gel electrophoresis followed by ethidium bromide staining and visualization under ultraviolet light or via direct sequencing of the PCR-products. The labeled amplified PCR products can also be detected by binding to immobilized oligonucleotide arrays.

In yet another embodiment, unlabelled amplification products can be detected via hybridization with labeled nucleic acid probes in methods known to one skilled in the art, such as dot or slot blot hybridization or filter hybridization.

The invention also relates to methods of using these nucleic acids to produce polypeptides in vitro or in vivo.

In one embodiment of the invention, a recombinant method of making a polypeptide of the invention comprises:

(a) preparing of a nucleic acid capable of directing a host cell to produce a polypeptide encoded by the SIVrcm genome;

(b) cloning the nucleic acid into a vector capable of being transferred into and replicated in a host cell, such vector containing operational elements for expressing the nucleic acid, if necessary;

(c) transferring the vector containing the nucleic acid and operational elements into a host cell capable of expressing the polypeptide;

(d) growing the host under conditions appropriate for expression of the polypeptide; and (e) harvesting the polypeptide.

The present invention also relates to non-recombinant methods of making the polypeptides and nucleic acids of the invention. In addition to synthetic methods, the non-recombinant methods involve culturing SIVrcm in cell lines, preferably in uninfected human peripheral blood mononuclear cells, under conditions appropriate for expression of the polypeptides and nucleic acids. This invention thus also relates to the polypeptides and nucleic acids produced by the virus in cell culture. The polypeptides and nucleic acids may be isolated and purified by methods known in the art.

The vectors contemplated for use in the present invention include any vectors into which a nucleic acid sequence as described above can be inserted, along with any preferred or required operational elements, and which vector can then be subsequently transferred into a host cell and, preferably, replicated in such cell. Preferred vectors are those whose restriction sites have been well documented and which contain the operational elements preferred or required for transcription of the nucleic acid sequence. Vectors may also be used to prepare large amounts of nucleic acids of the invention, which may be used, e.g., to prepare probes or other nucleic acid constructs.

When expression of a polypeptide is desired, the "operational elements" as discussed herein include at least one promoter sequence capable of initiating transcription of the nucleic acid sequence, at least one leader sequence, at least one terminator codon and/or termination signal, and any other DNA sequences necessary or preferred for appropriate transcription and subsequent translation of the vector nucleic acid. In particular, it is contemplated that such vectors will preferably contain at least one origin of replication recognized by the host cell along with at least one selectable marker.

Preferred expression vectors of this invention are those which function in bacterial and/or eukaryotic cells. Examples of vectors which function in eukaryotic cells include, but are not limited to Venezuelan equine encephalitis virus vectors, simian virus vectors, vaccinia virus vectors, adenovirus vectors, herpes virus vectors, or vectors based on retroviruses, such as murine leukemia virus, or HIV or other lentivirus (76).

The selected expression vector may be transfected into a suitable bacterial or eukaryotic cell system for purposes of expressing the recombinant polypeptide. Eukaryotic cell systems include but are not limited to cell lines such as HeLa, COS-1, 293T, MRC-5, or CV-1 cells. Primary human cells, such as lymph node cells, macrophages, etc., are also useful in practicing the invention.

The expressed polypeptides may be detected directly by methods known in the art including, but not limited to, Coomassie blue staining and Western blotting or indirectly, such as in detection of the expression product of a reporter gene, such as luciferase.

In another embodiment of the invention, the method comprises administering a composition comprising a vector comprising a nucleic acid of the invention to a mammal to produce a polypeptide in vivo.

The present invention also relates to polypeptides encoded by and/or derived from the nucleotide sequences of this invention. These polypeptides may be natural, synthetic or produced by recombinant methods. Polypeptides can be obtained as a crude lysate or can be purified by standard protein purification procedures known in the art which may include differential precipitation, molecular sieve chromatography, ion-exchange chromatography, isoelectric focusing, gel electrophoresis and affinity and immunoaffinity chromatography. The polypeptides may be purified by passage through a column containing a resin which has bound thereto antibodies specific for an open reading frame (ORF) polypeptide. The present invention also relates to compositions comprising one or more of the polypeptides of the invention.

A polypeptide or amino acid sequence derived from a designated nucleic acid sequence refers to a polypeptide having an amino acid sequence identical to that of a polypeptide encoded by the sequence, or a portion thereof wherein the portion consists of at least 6–8 amino acids, and more preferably at least 10 amino acids, and more preferably at least 11–15 amino acids, and most preferably at least 30 amino acids or which is immunologically cross-reactive with a polypeptide encoded by the sequence. The polypeptide may also be larger, e.g., at least 100 amino acids in length, depending on the desired use of the polypeptide. Polypeptides from the V3-loop region and the "crown" of gp41 of Env are particularly preferred.

A recombinant or derived polypeptide is not necessarily translated from a designated nucleic acid sequence; it may be generated in any manner, including for example, chemical synthesis, or expression of a recombinant expression system, or isolation from SIVrcm.

It should be noted that the nucleotide sequences described herein represent one embodiment of the present invention. Due to the degeneracy of the genetic code, it is to be understood that numerous choices of nucleotides may be made that will lead to a sequence capable of directing production of the polypeptides set forth above. As such, nucleic acid sequences which are functionally equivalent to the sequences described herein are intended to be encompassed within the present invention. For example, preferred codons which are appropriate to the host cell may be used (see, e.g., WO 98/34640), or the sequence may be modified to reduce the effect of any inhibitory/instability sequences and to provide for Rev-independent gene expression (77).

The polypeptides of this invention consist of at least 6–12 amino acids, more preferably at least 13–18 amino acids, even more preferably at least 19–24 amino acids and most preferably at least 25–30 amino acids encoded by, or otherwise derived from, the SIVrcm genomic sequence.

The present invention further relates to the use of polypeptides of the invention as diagnostic agents.

In one embodiment, the polypeptides of the invention can be used in immunoassays for detecting the presence of antibodies against SIVrcm in a mammal and for diagnosing the presence of SIVrcm infection in a mammal.

For the purposes of the present invention, "mammal" as used throughout the specification and claims, includes, but is not limited to humans, chimpanzees, mangabeys, other primates and the like.

In a preferred embodiment, test serum is reacted with a solid phase reagent having a surface-bound polypeptide of this invention as an antigen. The solid surface reagent can be prepared by known techniques for attaching polypeptides to solid support material. These attachment methods include non-specific adsorption of the polypeptide to the support or covalent attachment of the polypeptide to a reactive group on the support. After reaction of the antigen with an antibody against any one of the viruses of this invention in the serum, unbound serum components are removed by washing and the antigen-antibody complex is reacted with a secondary antibody such as labeled anti-human antibody. The label may be an enzyme which is detected by incubating the solid support in the presence of a suitable fluorimetric or colorimetric reagent. Other detectable labels may also be used, such as radiolabels or colloidal gold, and the like.

Immunoassays of the present invention may be a radioimmunoassay, Western blot assay, immunofluorescent assay, enzyme immunoassay, chemiluminescent assay, immunohistochemical assay and the like. Standard techniques for ELISA are well known in the art. Such assays may be a direct, indirect, competitive, or noncompetitive immunoassay as described in the art (see, e.g., ref. 61). Biological samples appropriate for such detection assays include, but are not limited to serum, liver, saliva, lymphocytes or other mononuclear cells.

Polypeptides of the invention may be prepared in the form of a kit, alone, or in combinations with other reagents such as secondary antibodies, for use in immunoassays.

In yet another embodiment, the polypeptides of the invention can be used as immunogens to raise antibodies and/or stimulate cellular immunity in a mammal.

The immunogen may be a partially or substantially purified peptide. Alternatively, the immunogen may be a cell, cell lysate from cells transfected with a recombinant expression vector, or a culture supernatant containing the expressed polypeptide. The immunogen may comprise one or more structural proteins, and/or one or more nonstructural proteins of SIVrcm, or a mixture thereof The effective amount of polypeptide per unit dose sufficient to induce an immune response depends, among other things, on the species of mammal inoculated, the body weight of the mammal and the chosen inoculation regimen, as well as the presence or absence of an adjuvant, as is well known in the art. Inocula typically contain polypeptide concentrations of about 1 microgram to about 50 milligrams per inoculation (dose), preferably about 10 micrograms to about 10 milligrams per dose, most preferably about 100 micrograms to about 5 milligrams per dose.

The term "unit dose" as it pertains to the inocula refers to physically discrete units suitable as unitary dosages for mammals, each unit containing a predetermined quantity of active material (polypeptide) calculated to produce the desired immunogenic effect in association with the required diluent.

Inocula are typically prepared as a solution in a physiologically acceptable carrier such as saline, phosphate-buffered saline and the like to form an aqueous pharmaceutical composition.

The route of inoculation of the polypeptides of the invention is typically parenteral and is preferably intramuscular, sub-cutaneous and the like. The dose is administered at least once. In order to increase the antibody level, at least one booster dose may be administered after the initial injection, preferably at about 4 to 6 weeks after the first dose. Subsequent doses may be administered as indicated.

To monitor the antibody response of individuals administered the compositions of the invention, antibody titers may be determined. In most instances it will be sufficient to assess the antibody titer in serum or plasma obtained from such an individual. Decisions as to whether to administer booster inoculations or to change the amount of the composition administered to the individual may be at least partially based on the titer.

The titer may be based on an immunobinding assay which measures the concentration of antibodies in the serum which bind to a specific antigen. The ability to neutralize in vitro and in vivo biological effects of SIVrcm may also be assessed to determine the effectiveness of the immunization.

For all therapeutic, prophylactic and diagnostic uses, the polypeptide of the invention, alone or linked to a carrier, as well as antibodies and other necessary reagents and appropriate devices and accessories may be provided in kit form so as to be readily available and easily used.

Where immunoassays are involved, such kits may contain a solid support, such as a membrane (e.g., nitrocellulose), a bead, sphere, test tube, microtiter well, rod, and so forth, to which a receptor such as an antibody specific for the target molecule will bind. Such kits can also include a second receptor, such as a labelled antibody. Such kits can be used for sandwich assays. Kits for competitive assays are also envisioned.

The immunogens of this invention can also be generated by the direct administration of nucleic acids of this invention to a subject. DNA-based vaccination has been shown to stimulate humoral and cellular responses to HIV-1 antigens in mice (69–72) and macaques (72, 73). More recent studies in infected chimpanzees have shown a possible application of this strategy in HIV-1-infected humans: DNA vaccination of HIV-1-infected chimpanzees with a construct that drives expression of HIV-1 env and rev appeared well-tolerated, and immunized animals demonstrated a boost in antibody response followed by a >1 log decrease in their virus loads (74). A DNA-based vaccine containing HIV-1 env and rev genes was injected into HIV-infected human patients in three doses (30, 100 or 300 micrograms) at 10-week intervals. Increased antibodies against gp120 were observed in the 100 and 300 μg groups. Increases were also noted in cytotoxic T lymphocyte (CTL) activity against gp160-bearing targets and in lymphocyte proliferative activity (78, 79). DNA-based vaccines containing HIV gag genes, with modification of the viral nucleotide sequence to incorporate host-preferred codons (see, e.g., WO 98/34640), and/or to reduce the effect of inhibitory/instability sequences (see, e.g., ref. 77), have likewise been described.

Therefore, it is anticipated that the direct injection of RNA or DNA vectors of this invention encoding viral antigen can be used for endogenous expression of the antigen to generate the viral antigen for presentation to the immune system without the need for self-replicating agents or adjuvants, resulting in the generation of antigen-specific CTLs and protection from a subsequent challenge with a homologous or heterologous strain of virus.

CTLs in both mice and humans are capable of recognizing epitopes derived from conserved internal viral proteins and are thought to be important in the immune response against viruses. By recognition of epitopes from conserved viral proteins, CTLs may provide cross-strain protection. CTLs specific for conserved viral antigens can respond to different strains of virus, in contrast to antibodies, which are generally strain-specific.

Thus, direct injection of RNA or DNA encoding the viral antigen has the advantage of being without some of the limitations of direct peptide delivery or viral vectors (see, e.g., ref. 81 and the discussions and references therein). Furthermore, the generation of high-titer antibodies to expressed proteins after injection of DNA indicates that this may be a facile and effective means of making antibody-based vaccines targeted towards conserved or non-conserved antigens, either separately or in combination with CTL vaccines targeted towards conserved antigens. These may also be used with traditional peptide vaccines, for the generation of combination vaccines. Furthermore, because protein expression is maintained after DNA injection, the persistence of B and T cell memory may be enhanced, thereby engendering long-lived humoral and cell-mediated immunity.

Nucleic acids encoding a SIVrcm polypeptide of this invention can be introduced into animals or humans in a physiologically or pharmaceutically acceptable carrier using one of several techniques such as injection of DNA directly into human tissues; electroporation or transfection of the DNA into primary human cells in culture (ex vivo), selection of cells for desired properties and reintroduction of such cells into the body, (said selection can be for the successful homologous recombination of the incoming DNA to an appropriate preselected genomic region); generation of infectious particles containing the SIVrcm gag and/or other SIVrcm genes, infection of cells ex vivo and reintroduction of such cells into the body; or direct infection by said particles in vivo. Substantial levels of polypeptide will be produced leading to an efficient stimulation of the immune system.

Also envisioned are therapies based upon vectors, such as viral vectors containing nucleic acid sequences coding for the polypeptides described herein. These molecules, developed so that they do not provoke a pathological effect, will stimulate the immune system to respond to the polypeptides.

The effective amount of nucleic acid immunogen per unit dose to induce an immune response depends, among other things, on the species of mammal inoculated, the body weight of the mammal and the chosen inoculation regimen, as is well known in the art. Inocula typically contain nucleic acid concentrations of about 1 microgram to about 50 milligrams per inoculation (dose), preferably about 10 micrograms to about 10 milligrams per dose, most preferably about 100 micrograms to about 5 milligrams per dose.

Immunization can be conducted by conventional methods. For example, the immunogen can be used in a suitable diluent such as saline or water, or complete or incomplete adjuvants. Further, the immunogen may or may not be bound to a carrier. While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more physiologically or pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art. The immunogen can be administered by any route appropriate for antibody production such as intravenous, intraperitoneal, intramuscular, subcutaneous, and the like. The immunogen may be administered once or at periodic intervals until a significant titer of anti-SIVrcm antibody is produced. The antibody may be detected in the serum using an immunoassay. The host serum or plasma may be collected following an appropriate time interval to prove a composition comprising antibodies reactive with the SIVrcm virus particle or encoded polypeptide. The gamma globulin fraction or the IgG antibodies can be obtained, for example, by use of saturated ammonium sulfate or DEAE Sephadex, or other techniques known to those skilled in the art.

In addition to its use to raise antibodies, the administration of the immunogens of the present invention may be for use as a vaccine for either a prophylactic or therapeutic purpose. When provided prophylactically, a vaccine(s) of the invention is provided in advance of any exposure to SIVrcm or in advance of any symptoms due to SIVrcm infection. The prophylactic administration of a vaccine(s) of the invention serves to prevent or attenuate any subsequent infection of SIVrcm in a mammal. When provided therapeutically, a vaccine(s) of the invention is provided at (or shortly after) the onset of infection or at the onset of any symptom of infection or any disease or deleterious effects caused by SIVrcm. The therapeutic administration of the vaccine(s) serves to attenuate the infection or disease. The vaccine(s) of the present invention may, thus, be provided either prior to the anticipated exposure to SIVrcm or after the initiation of infection.

In another embodiment, the polypeptides of the invention can be used to prepare antibodies against SIVrcm epitopes that are useful in diagnosis.

The term "antibodies" is used herein to refer to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', F(ab')$_2$ and F(v) as well as chimeric antibody molecules.

An antibody of the present invention is typically produced by immunizing a mammal with an immunogen or vaccine of the invention. In one embodiment, the immunogen or vaccine contains one or more polypeptides of the invention, or a structurally and/or antigenically related molecule, to induce, in the mammal, antibody molecules having immunospecificity for the immunizing peptide or peptides. The peptide(s) or related molecule(s) may be monomeric, polymeric, conjugated to a carrier, and/or administered in the presence of an adjuvant. In another embodiment, the immunogen or vaccine contains one or more nucleic acids encoding one or more polypeptides of the invention, or one or more nucleic acids encoding structurally and/or antigenically related molecules, to induce, in the mammal, the production of the immunizing peptide or peptides. The antibody molecules may then be collected from the mammal if they are to be used in immunoassays or for providing passive immunity.

The antibody molecules of the present invention may be polyclonal or monoclonal. Monoclonal antibodies may be produced by methods known in the art. Portions of immunoglobulin molecules may also be produced by methods known in the art.

The antibody of the present invention may be contained in various carriers or media, including blood, plasma, serum (e.g., fractionated or unfractionated serum), hybridoma supernatants and the like. Alternatively, the antibody of the present invention is isolated to the extent desired by well known techniques such as, for example, by using DEAE SEPHADEX, or affinity chromatography. The antibodies may be purified so as to obtain specific classes or subclasses of antibody such as IgM, IgG, IgA, IgG$_1$, IgG$_2$, IgG$_3$, IgG$_4$ and the like. Antibody of the IgG class are preferred for purposes of passive protection.

The presence of the antibodies of the present invention, either polyclonal or monoclonal, can be determined by, but are not limited to, the various immunoassays described above.

The antibodies of the present invention have a number of diagnostic and therapeutic uses. The antibodies can be used as an in vitro diagnostic agent to test for the presence of SIVrcm in biological samples in standard immunoassay protocols. Preferably, the assays which use the antibodies to detect the presence of SIVrcm in a sample involve contacting the sample with at least one of the antibodies under conditions which will allow the formation of an immunological complex between the antibody and the SIVrcm antigen that may be present in the sample. The formation of an immunological complex if any, indicating the presence of SIVrcm in the sample, is then detected and measured by suitable means. Such assays include, but are not limited to, radioimmunoassays (RIA), ELISA, indirect immunofluorescence assay, Western blot and the like. The antibodies may be labeled or unlabeled depending on the type of assay used. Labels which may be coupled to the antibodies include those known in the art and include, but are not limited to, enzymes, radionucleotides, fluorogenic and chromogenic substrates, cofactors, biotin/avidin, colloidal gold and magnetic particles. Modification of the antibodies allows for coupling by any known means to carrier proteins or peptides or to known supports, for example, polystyrene or polyvinyl microtiter plates, glass tubes or glass beads and chromatographic supports, such as paper, cellulose and cellulose derivatives, and silica.

Such assays may be, for example, of direct format (where the labelled first antibody reacts with the antigen), an indirect format (where a labelled second antibody reacts with the first antibody), a competitive format (such as the addition of a labelled antigen), or a sandwich format (where both labelled and unlabelled antibody are utilized), as well as other formats described in the art. In one such assay, the biological sample is contacted with antibodies of the present invention and a labeled second antibody is used to detect the presence of SIVrcm, to which the antibodies are bound.

The antibodies of the present invention are also useful as a means of enhancing the immune response.

The antibodies may be administered with a physiologically or pharmaceutically acceptable carrier or vehicle therefor. A physiologically acceptable carrier is one that does not cause an adverse physical reaction upon administration and one in which the antibodies are sufficiently soluble and retain their activity to deliver a therapeutically effective amount of the compound. The therapeutically effective amount and method of administration of the antibodies may vary based on the individual patient, the indication being treated and other criteria evident to one of ordinary skill in the art. A therapeutically effective amount of the antibodies is one sufficient to reduce the level of infection by one or more of the viruses of this invention or attenuate any dysfunction caused by viral infection without causing significant side effects such as non-specific T cell lysis or organ damage.

The route(s) of administration useful in a particular application are apparent to one or ordinary skill in the art. Routes of administration of the antibodies include, but are not limited to, parenteral, and direct injection into an affected site. Parenteral routes of administration include but are not limited to intravenous, intramuscular, intraperitoneal and subcutaneous.

The present invention includes compositions of the antibodies described above, suitable for parenteral administration including, but not limited to, pharmaceutically acceptable sterile isotonic solutions. Such solutions include, but are not limited to, saline and phosphate buffered saline for intravenous, intramuscular, intraperitoneal, or subcutaneous injection, or direct injection into a joint or other area.

Antibodies for use to elicit passive immunity in humans are preferably obtained from other humans previously inoculated with pharmaceutical compositions comprising one or more of the polypeptides of the invention. Alternatively, antibodies derived from other species may also be used. Such antibodies used in therapeutics suffer from several drawbacks such as a limited half-life and propensity to elicit an immune response. Several methods are available to overcome these drawbacks. Antibodies made by these methods are encompassed by the present invention and are included herein. One such method is the "humanizing" of non-human antibodies by cloning the gene segment encoding the antigen binding region of the antibody to the human gene segments encoding the remainder of the antibody. Only the binding region of the antibody is thus recognized as foreign and is much less likely to cause an immune response.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies which is in the range of from about 5 mg/kg to about 20 mg/kg body weight of the mammal, although a lower or higher dose may be administered. In general, the antibodies will be administered intravenously (IV) or intramuscularly (IM).

The invention also relates to the use of antisense nucleic acids to inhibit translation of peptides encoded by SIVrcm. The antisense nucleic acids are complementary to SIVrcm mRNAs encoding peptides of this invention. The antisense nucleic acids may be in the form of synthetic nucleic acids or they may be encoded by a nucleotide construct, or they may be semi-synthetic. The antisense nucleic acids may be delivered to the cells using methods known to those skilled in the art.

Kits designed for diagnosis of SIVrcm in a biological sample can be constructed by packaging the appropriate materials, including the nucleic acids and/or polypeptides of this invention and/or antibodies which specifically react with SIVrcm antigens, along with other reagents and materials required for the particular assay.

The following examples illustrate certain embodiments of the present invention, but should not be construed as limiting its scope in any way. Certain modifications and variations will be apparent to those skilled in the art from the teachings of the forgoing disclosure and the following examples, and these are intended to be encompassed by the spirit and scope of the invention.

EXAMPLE 1

PCR Amplification, Molecular Cloning, and Sequence Analysis of the SIVrcm Genome We have PCR amplified, cloned, and sequenced a complete SIVrcm proviral genome from a short-term PBMC culture originally established from the blood of a Gabonese red capped mangabey (82). Because of the extensive genetic diversity of this new SIV strain, we had to devise a novel PCR strategy to derive its genome. First, we amplified two small fragments in gag and pol using primers corresponding to sequences highly conserved among all known primate lentiviral lineages. This allowed us to subsequently design strain-specific primers to amplify the region between gag and pol (gag/pol) as well as the regions outside (flanking) gag and pol by placing the primers in reverse and amplifying the rest of the genome from unintegrated circular DNA molecules. Strategy and primer pairs are shown in FIG. 1. Overlapping PCR fragments were sequenced in their entirety.

Figure 3:
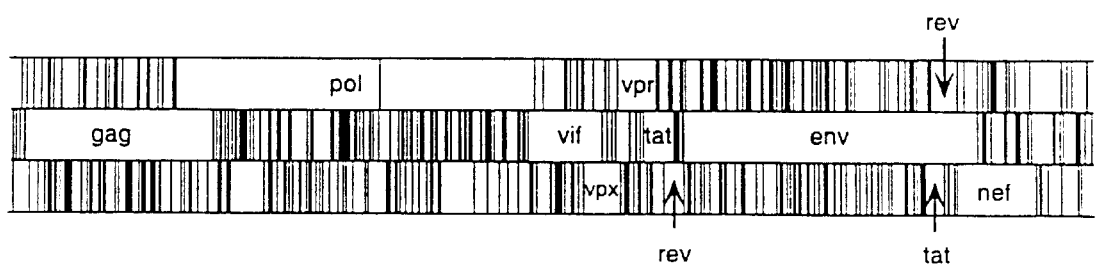
FIG. 3. Genomic organization of SIVrcm. Schematic diagram of the three possible reading frames of the SIVrcm genome. The location of stop codons are indicated by vertical lines, and the locations of the SIVrcm genes are indicated.
Figure 4:
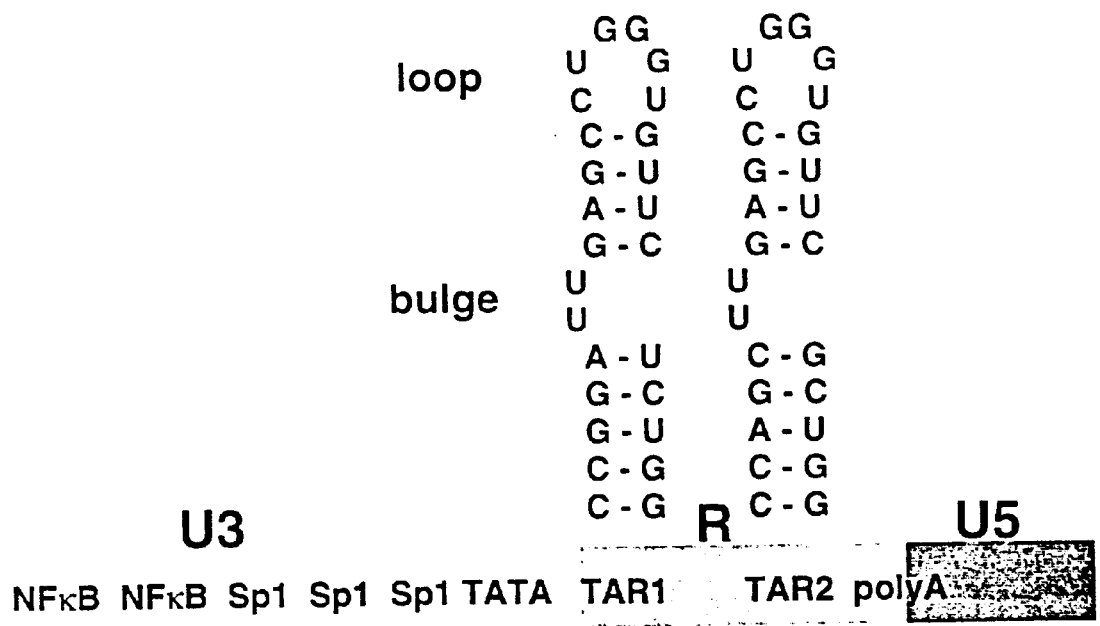
FIG. 4. Duplication of the TAR stemloop structure in the SIVrcm LTR (SEQ ID NO: 58)

Sequence analysis of the entire provirus revealed a genomic organization previously found only in members of the HIV-2/SIVsm/SIVmac group of viruses. That is, in addition to gag, pol, vif, vpr, env, tat, rev and nef genes, SIVrcm also encoded a vpx homologue thus far only been found in members of the HIV-2/SIVsm/SIVmac lineage (FIG. 3). Moreover, secondary structure analysis of its LTR sequences revealed a duplicated TAR stemloop structure, again a signature of SIVsm/SIVmac/HIV-2 viruses (FIG. 4). Based on these findings, we expected SIVrcm to fall within a greater mangabey lineage, forming a distinct subcluster similar to what has been observed for the four species-specific subclusters of SIVagm.

However, phylogenetic analyses failed to identify such a relationship of SIVrcm with the HIV-2/SIVsm/SIVmac group (FIG. 5). Instead of grouping closely with other mangabey viruses, SIVrcm clustered independently in most regions of its genome, forming a sixth lineage roughly equidistant from the other viruses (FIG. 5). In env and nef SIVsm, SIVrcm and SIVagm viruses appeared to be relatively more closely related to each other than they were to SIVcpz, SIVsyk and SIVmnd; however, even in these regions there was no particularly close relationship between the two mangabey lineages (FIGS. 5C and 5D). Also, in trees derived from the 3' and 5' pol regions, SIVrcm clustered with HIV-1 and SIVcpz viruses, with significant bootstrap values (FIG. 5B). Finally, there was also a close relationship between SIVrcm and SIVagmSAB, a virus we have previously reported to be mosaic with a divergent mangabey lineage in the 5' half of its genome (21). In the 5' half of gag, these two viruses clustered with significant bootstrap values (FIG. 5A), indicating that SIVrcm likely represents this previously hypothesized divergent mangabey lineage. These results were confirmed by the use of maximum likelihood approaches to determine tree topologies.

The results suggest that SIVrcm represents a highly divergent mangabey virus which forms an independent lineage (for most of its genome) roughly equidistant from all other primate lentiviruses. The extent of diversity between SIVrcm and the other mangabey lineage (SIVsm) is surprising, given the known relationships of SIVagm strains from different African green monkey species. One explanation for this is that mangabeys acquired their SIV infection a very long time ago (millions of years), even before African green monkeys became infected with SIVagm. Another is that these viruses have evolved with in their respective species with vastly different rates of evolution. Also of interest are the close phylogenetic relationships of SIVrcm to SIVcpz in the 3' and 5' pol regions, as well as to SIVagmSAB in the gag region, which are highly significant. These finding strongly suggest recombination events in the distant past. However, based on current data it is impossible to determine which of these lineages are mosaic. For example, it is quite conceivable the SIVrcm is non-recombinant and that both SIVcpz and SIVagmSAB viruses acquired SIVrcm sequences independently through cross-species transmission events in the past. This would also mean that HIV-1 is mosaic with SIVrcm related sequences. These findings are important because they indicate that primate lentiviral evolution is far more complex than previously appreciated, and that sequences from additional primate lentiviruses (in particular SIVcpz, SIVrcm, and SIVagm strains from Gabon and Cameroon) are critically needed to resolve the unexpected phylogenetic relationships of SIVrcm.

EXAMPLE 2

Identification of a New Reading Frame in SIVrcm and SIVsm Viruses

Analysis of the SIVrcm sequence revealed that there were about 100 bp of "non-coding sequences" between the splice donor site of the first tat and rev exons, and the initiation codon of the env open reading frame (ORF). Upon closer analysis, it was realized that the first exon of rev, instead of being terminated by a stop codon immediately downstream of the splice site, continued uninterrupted for about 100 more base pairs. Comparison of the genomic organization of members of all other major primate lentiviral lineages indicated that there was only one other group, i.e., the SIVsm/SIVmac group, that had a similarly "extended first rev exon". All other viruses had stop codons shortly after the splice site (except for members of the HIV-1/SIVcpz group, which encode the vpu gene in this region).

Figure 6:
FIG. 6. Alignment of the putative polypeptide products of the extended rev ORFs in SIVsm and SIVrcm. Asterisks denote stop codons. Conservative amino acid changes are indicated as a colon (:); a vertical line depicts the position of the splice donor.

FIG. 6 shows an alignment of the deduced amino acid sequence of the SIVsmPBj1.9 and SIVrcmGB1 extended rev ORFs. The putative PBj protein is 71 amino acids in length, while the putative SIVrcm protein is shorter, i.e., only 54 amino acids. However, this shorter length could be the result of inactivating mutations (frameshift and in frame stop codons). Assuming a "corrected" sequence, the SIVrcm extended rev ORF would encode a 105 amino acid protein (FIG. 6) with considerable sequence homology to the corresponding SIVsm product throughout its entire length. Correction of inactivating mutations would restore the predicted coding capacity of the SIVrcm rev ORF to a protein of 105 amino acids, and nucleic acids containing repaired coding sequences, as well as the polypeptides encoded by the repaired coding sequences, are also considered to be a part of the invention.

The conservation of the extended rev ORFs among different members of the HIV-2/SIVsm/SIVmac group of virus was also examined. FIG. 7 shows an amino acid sequence alignment, including all sequences from the Los Alamos HIV sequence database. The results were surprising: all SIVsm/SIVmac strains encoded a highly conserved and uninterrupted open reading frame; however, all HIV-2 strains, except one (FO784) which we was considered to represent an ill-adapted sooty managbey virus in humans, contained inactivating mutations (stop codons) in this "extended rev ORF".

The finding of an "extended rev first exon ORF" in both SIVrcm and SIVsm lineages is significant for several reasons: (i) it suggests the existence of a "mangabey virus specific" protein, which likely plays an important role in mangabey virus replication (as do all other accessory proteins); (ii) it suggests the existence of a "mangabey virus specific" protein whose expression may be abrogated as a consequence of SIVsm adaptation to the human host; (iii) it suggests the existence of a "managbey virus specific" protein, which could serve as a functional vpu equivalent (the position of this new ORF in the SIVrcm/SIVsm genome, as well as its overall length, are reminiscent of the vpu gene in HIV-1/SIVcpz, although amino acid sequence homologies between the putative SIVsm/SIVrcm extended first rev exon product and the HIV-1/SIVcpz Vpu protein were not found; however, this is not necessarily surprising since the Vpu proteins among different members of the HIV-1/SIVcpz lineage are so divergent that they cannot be aligned (52). These findings are important for the current application because they highlight another potential structural similarity between SIVrcm and SIVsm lineages. However, additional SIVrcm isolates need to be characterized to confirm the existence of this reading frame (and its putative protein product) among other viruses.

REFERENCES

1. Allan, J. S., M. Short, M. E. Taylor, S. Su, V. M. Hirsch, P. R. Johnson, G. M. Shaw, and B. H. Hahn. 1991.

Species-specific diversity among simian immunodeficiency viruses from African green monkeys. *J. Virol.* 65:2816–2828.
2. Barre-Sinoussi, F., J. C. Chermann, F. Rey, M. T. Nugeyre, S. Chamaret, J. Gruest, C. Dauguet, C. Axier-Blin, F. Vezinet-Brun, C. Rouzioux, W. Rozenbaum and L. Montagnier. 1983. Isolation of a T-lymphotropic retrovirus from a patient at risk for acquired immune deficiency syndrome (AIDS). *Science* 220:868–871.
3. Chen, Z., A. Luckay, D. L. Sodora, P. Telfer, P. Reed, A. Gettie, J. M. Kanu, J. A. Yee, D. D. Ho, L. Zhang and P. A. Marx. 1997. HIV-2 Seroprevalence and Characterization of a New HIV-2 Genetic Subtype (F) within the Natural Range of SIV Infected Sooty Mangabeys. *J. Virol.* 71:3953–3960.
4. Chen, Z., P. Telfer, P. Reed, A. Gettie, L. Zhang, D. D. Ho and P. A. Marx. 1996. Genetic characterization of new West African Simian Immunodeficiency Virus SIVsm: Geographic clustering of household-derived SIV strains with HIV-2 subtypes and genetically diverse viruses from a single feral sooty mangabey troop. *J. Virol.* 70:3617–3627.
5. Chen, Z., P. Telfer, P. Reed, L. Zhang, A. Gettie, D. D. Ho, and P. A. Marx. 1995. Isolation and characterization of the first simian immunodeficiency virus from a feral sooty mangabey (*Cercocbus atys*) in West Africa *J. Med. Primatol.* 24:108–115.
6. Chen, Z., P. Zhou, D. D. Ho, N. R. Landau and P. A. Marx. 1997. Genetically divergent strains of simian immunodeficiency virus use CCR5 as a corecptor for entry. *J. Virol.* 71:2705–2714.
7. Clavel, F., D. Guetard, F. Brun-Vezinet, S. Chamaret, M. A. Rey, M. O. Santos-Ferreira, A. G. Laurent, C. Dauguet, C. Katlama, C. Rouzioux, D. Klatzmann, J. L. Champalimaud, and L. Montagnier. 1986. Isolation of a new human retrovirus from West African patients with AIDS. *Science* 233:343–346.
8. Daniel, M. D. , N. L. Letvin, N. W. King, M. Kannagi, P. K. Sehgal, R. D. Hunt, P. J. Kanki, M. Essex and R. C. Desrosiers. 1985. Isolation of T-cell tropic HTLV-III-like retrovirus from macaques. *Science,* 228:1201–1204.
9. Emau, P., H. M. McClure, M. Isahakia, J. G. Else, and P. N. Fultz. 1991. Isolation from African Sykes' monkeys (*Cercopithecus mitis*) of a lentivirus related to human and simian immuno-deficiency viruses. *J. Virol.* 65:2135–2140.
10. Faulkner, D. M. and J. Jurka. 1988. Multiple aligned sequence editor (MASE). Trends Biochem. *Science.* 13:321–322.
11. Felsenstein, J. 1988. Phylogenies from molecular sequences: inference and reliability. *Annu. Rev. Genet.* 22:521–565.
12. Felsenstein, J. 1989. PHYLIP—Phylogeny Inference Package (Version 3.2). *Cladistics* 5:164–166.
13. Fultz, P. N., H. M. McClure, D. C. Anderson, R. B. Swenson, R. Anand, and A. Srinivasan. 1986. Isolation of a T-lymphotropic retrovirus from naturally infected sooty mangabey monkeys (*Cercocebus atys*). *Proc. Natl. Acad. Sci. USA* 83:5286–5290.
14. Gao, F., L. Yue, D. L. Robertson, S. C. Hill, H. Hui, R. J. Biggar, A. E. Neequaye, T. M. Whelan, D. D. Ho, G. M. Shaw, P. M. Sharp, and B. H. Hahn. 1994. Genetic diversity of human immunodeficiency virus type 2: evidence for distinct sequence subtypes with differences in virus biology. *J. Virol.* 68:7433–7447.
15. Gao, F., L. Yue, A. T. White, P. G. Pappas, J. Barchue, A. P. Hanson, B. M. Greene, P. M. Sharp, G. M. Shaw, and B. H. Hahn. 1992. Human infection by genetically diverse SIVsm-related HIV-2 in West Africa. *Nature* (London) 358:495–499.
16. Garnett, G. P., and R. Antia. 1994. Population Biology of Virus—Host Interactions. In The Evolutionary Biology of Viruses, Raven Press, New York, N.Y.
17. Grubb, L. 1982. Refuges and dispersal in the speciation of African forest mamamals. In Biological Diversification in the Tropics, G. T. Prance (ed.) Columbia University Press, New York pp 537–553.
18. Hirsch, V. M., R. A. Olmsted, M. Murphey-Corb, R. H. Purcell, and P. R. Johnson. 1989. An African primate lentiviruses (SIVsm) closely related to HIV-2. *Nature* (London) 339:389–392.
19. Huet, T., R. Cheynier, A. Meyerhans, G. Roelants, and S. Wain-Hobson. 1990. Genetic organization of a chimpanzee lentivirus related to HIV-1. *Nature* (London) 345:356–359.
20. Janssens, W., K. Fransen, M. Peeters, L. Heyndrickx, J. Motte, L. Bedjabaga, E. Delaporte, P. Piot and G. Van Der Groen. 1994. Phylogenetic analysis of a new chimpanzee lentivirus SIVcpz-gab2 from a wild-captured chimpanzee from Gabon. *AIDS Res. Human Retro.* 10:1191–1192.
21. Jin, M. J., H. Hui, D. L. Robertson, M. C. Muller, F. Barre-Sinoussi, V. M. Hirsch, J. S. Allan, G. M. Shaw, P. M. Sharp and B. H. Hahn. 1994. Mosaic genome structure of simian immunodeficiency virus from West African green monkeys. *EMBO J.* 13:2935–2947.
22. Johnson, P. R., A. Fomsgaard, J. Allan, M. Gravell, W. T. London, R. A. Olmsted, and V. M. Hirsch. 1990. Simian immunodeficiency viruses from African green monkeys display unusual genetic diversity. *J. Virol.* 64:1086–1092.
23. Kestler, H. W., Y. Li, Y. M. Naidu, C. V. Butler, M. F. Ochs, G. Jaenel, N. W. King, M. D. Daniel, and R. C. Desrosiers. 1988. Comparison of simian immunodeficiency virus isolates. *Nature* (London) 331:619–622.
24. Kimura, M. 1983. The neutral theory of molecular evolution. Cambridge University Press, Cambridge, United Kingdom.
25. Kraus, G., A. Werner, M. Baier, D. Binniger, F. J. Ferdinand, S. Norley, and R. Kurth. 1989. Isolation of human immunodeficiency virus-related simian immunodeficiency viruses from African green monkeys. *Proc. Natl. Acad. Sci. USA* 86:2892–2896.
26. Kusumi, K., B. Conway, S. Cunningham, A. Berson, C. Evans, A. K. N. Iversen, D. Colvin, M. V. Gallo, S. Coutre, E. G. Shpaer, D. V. Faulkner, A>deRonde, S. Volkman, C. Williams, M. S. Hirsch and J. I. Mullins. 1992. Human immunodeficiency virus type 1 envelope gene structure and diversity in vivo and after cocultivation in vitro. *J. Virol.* 66:875–885.
27. Kwon, D., et al., Unpublished data.
28. Letvin, N. L., M. D. Daniel, P. K. Sehgal, R. C. Desrosiers, R. D. Hunt, L. M. Waldron, J. J. MacKey, D. K. Schmidt, L. V. Chalifoux, and N. W. King. 1985. Induction of AIDS-like disease in macaque monkeys with T-cell tropic retrovirus STLV-III. *Science* 230:71–73.
29. Lowenstine, L. J., N. C. Pedersen, J. Higgins, K. C. Pallis, A. Uyeda, P. A. Marx, N. W. Lerche, R. J. Munn, and M. B. Gardner. 1986. Seroepidemiologic survey of captive Old World primates for antibodies to human and simian retroviruses and isolation of a lentivirus from sooty mangabeys (*Cercocebus atys*). *Int. J. Cancer* 38:563–574.
30. Marx, P. A., R. W. Compans, A. Gettie, J. K. Staas, R. M. Gilley, M. J. Mulligan, C. Dexiang, and J. H. Eldridge.

1993. Protection against vaginal SIV transmission with microencapsulated vaccine. *Science* 260:1323–1327.
31. Marx, P. A., Y. Li, N. W. Lerche, S. Sutjipto, A. Gettie, J. A. Yee, B. Brotman, A. M. Prince, A. Hanson, R. G. Webster, and R. C. Desrosiers. 1991. Isolation of Simian immunodeficiency virus related to human immunodeficiency virus type 2 from a west African pet sooty mangabey. *J. Virol.* 65(8):4480–4485.
32. Marx, P. A., A. I. Spira, A. Gettie, P. J. Dailey, R. S. Veazey, A. A. Lackner, C. J. Mahoney, C. J. Miller, L. E. Claypool, D. D. Ho and N. J. Alexander. 1996. Progesterone Implants Enhance SIV Vaginal Transmission and Early Virus Load. Nature Medicine. *Nature Medicine* 2:1084–1089.
33. Miura, T., J. Sakuragi, M. Kawamura, M. Fukasawa, E. N. Moriyama, T. Gojobori, K. Ishikawa, J. A. A. Mingle, V. B. A. Nettey, H. Akari, M. Enami, H. Tujimoto, M. Hayami. 1990. Establishment of a phylogenetic survey system for AIDS-related lentiviruses and demonstration of a new HIV-2 subgroup. *AIDS* 4:1257–1261.
34. Mojun J J, H Huxiong, D L Robertson, M C Muller, F. Barre-Sinoussi, V M Hirsch, J S Allan, G M Shaw, P M Sharp and B H Hahn. 1994. Mosaic genome structure of simian immunodeficiency virus from West African Green monkeys. *EMBO J.* 13:2935–2947.
35. Muller, M. C., N. K. Saksena, E. Nerrienet, C. Chappey, V. M. Herve, J. P. Durand, P. Legal, M. C. Lang-Campodonico, J. P. Digoutte, A. J. Georges, M. Georges, P. Sonigo, and F. Barre-Sinoussi. 1993. Simian immunodeficiency viruses from central and western Africa: evidence for a new species-specific lentivirus in tantalus monkeys. *J. Virol.* 67:1227–1235.
36. Murphey-Corb, M., L. N. Martin, S. R. Rangan, G. B. Baskin, B. J. Gormus, R. H. Wolf, W. A. Andes, M. West and R. C. Montelaro. 1986. Isolation of an HTLV-III related retrovirus from macaques with simian AIDS and its possible origin in asymptomatic mangabeys. *Nature* (London) 321:435–437.
37. Myers, G., B. H. Hahn, J. W. Mellors, L. E. Henderson, B. Korber, K-T Jeang, F. E. McCutchan and G. N. Pavlakis. 1995. Human retorviruses and AIDS. A compilation and analysis of nucleaic acid and amino acid sequences. Los Alamos National Laboratory, Los Alamos, N. Mex.
38. Myers, G., K. MacInnes, and B. Korber. 1992. The emergence of simian/human immunodeficiency viruses. *AIDS Res. Hum. Retroviruses* 8:373–386.
39. Nerienet E, Amouretti X, Muller-Trutwin M C, et al. 1998. Phylogenetic analysis of SIV and STLV type I in mandrills (*Mandrillus sphinx*): indications that intracolony transmissions are predominantly the result of male-to-male aggressive contacts. *AIDS Res. Hum. Retroviruses,* 14:785–96.
40. Ohta, Y., T. Masuda, H. Tsujimoto, K. Ishikawa, T. Kodama, S. Morikawa, M. Nakai, S. Honjo, and M. Hayami. 1988. Isolation of simian immunodeficiency virus from African green monkeys and seroepidemiologic survey of the virus in various non-human primates. *Int. J. Cancer* 41:115–122.
41. Otsyula, M., J. Yee, M. Jennings, M. Suleman, A. Gettie, R. Tarara, M. Isahakia, P. Marx and N. Lerche. 1996. Prevalence of antibodies against simian immunodeficiency virus (SIV) and simian T-lymphotropic virus (STLV) in a colony of non-human primates in Kenya, East Africa. *Annals Trop. Med. Parisitol.* 90:65–70.
42. Peeters, M., K. Fransen, E. Delaporte, M. Van den Haesevelde, G.-M. Gershy-Damet, L. Kestens, G. Van der Groen and P. Piot. 1992. Isolation and characterization of a new chimpanzee lentivirus (simian immunodeficiency virus isolate cpz-ant) from a wild-captured chimpanzee. *AIDS* 6:447–451.
43. Peeters, M., C. Honore, T. Huet, L. Bedjabaga, S. Ossari, P. Bussi, R. W. Cooper, and E. Delaporte. 1989. Isolation and partial characterization of an HIV-related virus occurring naturally in chimpanzees in Gabon. *AIDS* 3:625–630.
44. Peeters, M., W. Janssens, K. Fransen, J. Brandful, L. Hendrickx, K. Koffi, E. Delaporte, P. Piot, G. M. Gershy-Damet, and G. van der Groen. 1994. Isolation of simian immunodeficiency viruses from two sooty mangabeys in Cote d'Ivoire: virological and genetic characterization and relationship to other HIV type 2 and SIVsm/mac strains. *AIDS Res. Hum. Retroviruses.* 10:1289–1294.
45. Reimann, K. A., K. Tenner-Racz, P. Racz, D. C. Montefiori, Y. Yasutomi, W. Lin, B. J. Ransil and N. L. Letvin. 1994. Immunopathogenic events in acute infection of rhesus monkeys with simian immunodeficiency virus of macaques. *J. Virol.* 68:2362–2370.
46. Robbins C B. 1978. The Dahomey Gap—A reevaluation of its significance as a faunal barrier to West African high forest mammals. *Bull. Carnegie Mus. Nat Hist.* 6: 168–174.
47. Sharp, P. M., D. L. Robertson, F. Gao, and B. H. Hahn. 1994. Origins and diversity of human immunodeficiency viruses. *AIDS* 8 (Suppl.):S27–S42.
48. Stivahtis, G. L., M. A. Soares, M. A. Vodicka, B. H. Hahn, and M. Emerman. 1997. Conservation and host specificity of Vpr-mediated cell cycle arrest suggest a fundamental role in primate lentivirus evoluation and biology. *J. Virol.* 71:4331–4338.
49. Stivahtis, G. L., M. A. Soares, M. A. Vodicka, B. H. Hahn and M. Emerman. 1997. Conservation and host specificity of Vpr-Mediated cell cycle arrest suggest a fundamental role in primate lentivirus evoluation and biology. *J. Virol.* 71:4331–4338.
50. Tomonaga K, J Katahira, M Fukasawa, M A Hassan, M Kawamura, H Akari, T Miura, T Goto, M Nakai, M Suleman, M Isahakia and M Hayami. 1993. Isolation and characterization of simian immunodeficiency virus from African white-crowned mangabey monkeys (*Cercocebus torquatus lunulatus*). *Arch. Virol.* 129:77–92.
51. Tsujimoto, H., R. W. Cooper, T. Kodama, M. Fukasawa, T. Miura, Y. Ohta, K. I. Ishikawa, M. Nakai, E. Frost, G. E. Roelants, J. Roffi, and M. Hayami. 1988. Isolation and characterization of simian immunodeficiency virus from mandrills in Africa and its relationship to other human and simian immunodeficiency viruses. *J. Virol.* 62:4044–4050.
52. Vanden Haesevelde, M. M., M. Peeters, G. Jannes, W. Janssens, G. Van Der Groen, P. M. Sharp and E. Saman. 1996. Sequence analysis of a highly divergent HIV-1-related lentivirus isolated from a wild captured chimpanzee. *Virology* 221:346–350.
53. Wolfheim, J. H. 1983. Primates of the world. Univ. of Washington, Seattle.
54. Agarwal et al. 1972,*Angew. Chem. Int. Ed. Engl.* 11:451. The phosphotriester method of Hsiung et al. 1979, *Nucleic Acids Res.* 6:1371.
55. Baeucage et al. 1981, *Tetrahedron Letters* 22:1859–1862. Automated diethylphosphoramidite method.
56. Biedleret et al. 1988. *J. Immunol.* 141:4053
57. Hollander, M. C. et al. 1990. *Biotechniques;* 9:174–179, RNase protection (Sambrook, J. et al. 1989. In "Molecular Cloning, a Laboratory Manual", Cold Spring Harbor Press, Plainview, N.Y.).

58. Hsiung et al. 1979. *Nucleic Acids Res* 6:1371
59. Jones et al., 1986. *Nature* 321:552
60. Kafatos, F. C. et al. 1979. *Nucleic Acids Res.,* 7:1541–1522
61. Oellerich, M. 1984. *J. Clin. Chem. Clin. BioChem* 22:895–904
62. Sambrook, J. et al. 1989. In "Molecular Cloning, A Laboratory Manual", Cold Spring Harbor Press, Plainview, N.Y.
63. Southern, E. M. 1975. J. Mol. Biol., 98:503–517.
64. Verhoeyan, et al. 1988. *Science* 239:1534.
65. Watson, J. D., et al. 1992. In "Recombinant DNA" Second Edition, W. H. Freeman and Company, New York.
66. Alwine, J. C., et al. 1977. *Proc. Natl. Acad. Sci.,* 74:5350–5354.
67. See, e.g., Anderson, et al. 1996. *Antimicrob. Agents Chemother.,* 40:2004–2011; Azad, et al. 1995. *Antiviral Res.,* 28:101–111; Azad, et al. 1993. *Antimicrob. Agents Chemother.,* 37:1945–1954; Leeds, et al. 1997. *Drug. Metab. Dispos.,* 25:921–926; and references therein. See also, Cook, P. D., 1993. Monomers for preparation of oligonucleotides having chiral phosphorus linkages. U.S. Pat. No. 5,212,295 (general method of making DNA analogs, including phosphorothioates, thioesters, etc.); and Iyer et al. 1990 *J. Org. Chem.* 55:4693–4699 (synthetic method for making phosphorothioate oligos).
68. See, e.g., Nielsen, et al., WO 98/03542, Hyrup and Nielsen 1996. *Bioorg. Med. Chem.* 4:5–23; and Nielsen, et al. 1991. *Science* 254:1497–1500; and references therein.
69. Lu S, Arthos J. Montefiori D C, et al. Simian immunodeficiency virus DNA vaccine trial in macaques. *J. Virol* 1996;70:3978–91.
70. Haynes J R, Fuller D H, Eisenbraun M D, Ford M J, Pertmer T M. Accell particle-mediated DNA immunization elicits humoral, cytotoxic and protective responses. *AIDS Res Human Retroviruses* 1994; 10 (suppl 2): S43–5.
71. Okuda, K, Bukawa H, Hamajima K, et al. Induction of potent humoral and cell-mediated immune responses following direct injection of DNA encoding the HIV type 1 Env and Rev gene products. *AIDS Res Hum Retroviruses* 1995;11:933–43.
72. Wang B, Boyer J D, Srikantan V, et al. Induction of humoral and cellular immune responses to the human immunodeficiency type 1 virus in non-human primates by in vivo DNA inoculation. *J. Virol* 1995; 21:102–12.
73. Boyer J D, Wang B, Ugen K, et al. In vivo protective anti-HIV immune responses in non-human primates through DNA immunization. *J. Med. Primatol.* 1996; 25–242–50.
74. Boyer J D, Ugen K E, Chattergoon M, et al. DNA vaccination as anti-HIV immunotherapy in infected chimpanzees. *J. Infect. Dis.* 1997;176:1501–9.
75. Simon F; Mauclere P; Roques P; Loussert-Ajaka I; Muller-Trutwin M C; Saragosti S; Georges-Courbot M C; Barre-Sinoussi F; Brun-Vezinet F. Identification of a new human immunodeficiency virus type 1 distinct from group M and group O. *Nature Medicine,* 4:1032–1037.
76. See, e.g., Naldini, N., Blömer, U., Gallay, P., Ory, D., Mulligan, R., Gage, F. H., Verma, I. M. and Trono, D., "In Vivo Gene Delivery and Stable Transduction of Nondividing Cells by a Lentiviral Vector", *Science,* 272:263–267 (1996); Srinivasakumar, N., Chazal, N., Helga-Maria, C., Prasad, S., Hammarskjöld, M.-L., and Rekosh, D., "The Effect of Viral Regulatory Protein Expression on Gene Delivery by Human Immunodeficiency Virus Type 1 Vectors Produced in Stable Packaging Cell Lines", *J. Virol.,* 71:5841–5848 (August 1997); Zufferey, R., Nagy, D., Mandel, R. J., Naldini, L. and Trono, D., "Multiply Attenuated Lentiviral Vector Achieves Efficient Gene-Delivery In Vivo", *Nature Biotechnology,* 15:871–875 (September 1997); and Kim, V. N., Mitrophanous, K., Kingsman, S. M., and Kingsman, A. J., "Minimal Requirement for a Lentivirus Vector Based on Human Immunodeficiency Virus Type 1", *J. Virol.,* 72:811–816 (January 1998); concerning lentiviral vectors.
77. See, e.g., Schwartz et al.,*J. Virol.,* 66:7176–7182(1992); International Publication No. WO 93/20212 (1993); Schneider, R., Campbell, M., Nasioulas, G., Felber, B. K., and Pavlakis, G. N., "Inactivation of the human immunodeficiency virus type 1 inhibitory elements allows Rev-independent expression of Gag and Gag/protease and particle formation," *J. Virol ,* 71:4892–4903 (1997) concerning the identification and mutation of inhibitory and instability regions using multiple point mutations within HIV-1 gag, protease and pol coding regions to reduce the effects of these regions and increase expression of the encoded polypeptide.
78. MacGregor et al., *J. Infect Dis* 178:92–100 (1998).
79. Donnelly et al., *Annu. Rev. Immunol.* 15:617–648 (1997).
80. Winzeler et al., *Science* 281:1194–1197 (1998)
81. Ulmer et al., *Science,* 259:1745–1749 (1993)
82. Georges-Courbot et al., *J. Virol.,* 72:600–608 (1998)

Modification of the above described invention that are obvious to those of skill in the fields of genetic engineering, immunology, protein chemistry, medicine, and related fields are intended to be within the scope of the following claims.

All of the references cited herein above are hereby incorporated by reference.

What is claimed is:

1. An isolated and purified polypeptide encoded by nucleic acid comprising the nucleotide sequence of the genome of the simian immunodeficiency virus isolate SIVrcm shown in SEQ ID NO: 1, wherein the amino acid sequence of said polypeptide comprises a sequence selected from the group consisting of SEQ ID NO: 10, 23, 45–53, 54 and 56.

2. A composition comprising the isolated and purified polypeptide of claim 1 and a physiologically acceptable carrier.

* * * * *

SEQUENCE LISTING

<160> NUMBER OF SEQ ID NOS: 58

<210> SEQ ID NO 1
<211> LENGTH: 9465
<212> TYPE: DNA
<213> ORGANISM: Simian immunodeficiency virus
<220> FEATURE:
<223> OTHER INFORMATION: Nucleotide sequence of the SIVrcm genome

<400> SEQUENCE: 1
tggcgcccga acagggactt gagagtggct gagagacctc cgaggctaag gttcggcgcg     60

-continued

```
gcaggtcacc gcgggagtgg aaccttgacc aggtaagagc tgcctggtgg cttcaaagtg      120
ctagagaaag tgagctagcg aaggaagcag ggcaacccgg tccggtactg ggcctctagg      180
gaaggagcga agtcctagag aagggaggaa aatgggtgcg agagcctcat tgttgtcagg      240
gaagaagcta gacgcatggg aatcagttag gttacggccc ggcgggaaaa agaaatacat      300
gctgaagcat ttggtatggg catgcaaaaa actaaataaa tttggcttga gtgatcattt      360
gttagaaaca gcaacaggat gtgaaaaaat attaggagtc ctgctgcctc tagttccgac      420
agggtcagag gggctaaaaa gcctctttaa tttgtgctgc gtactctggt gcgtacacaa      480
ggaagtgaaa gtgaaagaca cagaggaagc tgtagcaaaa gtgaaagaat gctgccatct      540
agtggaaaaa gcagaaaata caacagaaaa agaaaaggga gcaacagcgc cacctagtgg      600
acaaagagga aattatccta taattactat aaatcagcag cctgagcata atcctatatc      660
accaaggact ctaaatgcct gggtcaaggt ggtagaggag aaaaaattct cagcagaagt      720
agcgcccatg ttctcggcac tatcagaagg ctgcataccc tatgatataa atcaaatgct      780
aaatgccata ggggaacacc aggtgcgct gcagatagta aaggaagtga tcaatgagga      840
agcagcagac tgggatgcta gacatccagt accaggcccg ataccagcag ggcaacttag      900
agaaccaaca ggaagtgaca tagcagggac aactagctca atagcagaac agatagcttg      960
gaccaccaga gcaaacaacc ccattaatgt gggcaatctg tacagaaatt ggataatagt     1020
agggttacaa aaatgggtaa aaatgtacaa tccagtgaac atcctagata taaagcaagg     1080
accaaaagag tcattcaagg attatgtgga tagattttat aaagccttga gagcagaaca     1140
ggcagacccg gcagtaaaaa attggatgac acaatcactg ctgatacaaa atgctaaccc     1200
agactgtaaa atggtactca agggtctggg aatgaaccct tctttagaag aaatgctaac     1260
agcctgtcag ggggtaggag accccagca taaagctcgg gtactagcag aggccatgca     1320
aatgatgcaa agtaatatca tggctcagca atcagcaaac aggggcctc caagaagatc     1380 aggaggaaat ccaaatttaa gatgttacaa ttgtggtaag ccaggacaca tttctagata     1440
ttgtaaagcc cctagaagga agggatgctg gaaatgtgga tccccagacc atctcttgaa     1500
agactgcaca aagcaaataa attttttagg gagactcccc tggggtcagg ggaagccgag     1560
gaactttcct ttgacttcct tgactccctc tgctccaggg atggagagca attacgaccc     1620
tgcagaagag atgctaaaga attatctgag gagggcaggg gaacaaaaga gacaacagag     1680
gcaggaagag agcaagaaga gagagggagc atatcaggaa gccttaacct ccctcaattc     1740
gctctttgga agcgaccaac tacaatagct caaatagaag ggcagaaagt ggaggtccta     1800
ttagacacag gagcagatga cacagtaatt gaaggaatag aattaggaaa tgattggacc     1860
ccaaaaataa taggaggaat aggggatat attaatgtaa aacaatataa aaactgtgaa     1920
attgaaatag ctgaaaaaag gactcatgct catgtgctag tgggaccaac accagtgaat     1980 attatagga gaaatgtttt aaagaaatta ggagccacac taaattttcc aataagccaa     2040
atagaaacta aaaggtaga attaaagtct ggacaagatg gaccacgagt aaaacaatgg     2100
ccattgtcaa agaaaaaat agaagcttta acagaaattt gcaatgcaat ggagaaggaa     2160
ggaaaaattt caaaaatagg gccagaaaac ccctacaaca caccaatatt ctgtattaaa     2220
aagaaagact ccacaaaatg gagaaaattg gtagatttta gagaactaaa taagagaaca     2280
caggactttt tgaggtgca gctgggaata ccacatccag gaggattaaa gcaatgtgag     2340
agaataacgg tattagacat cggggatgca tattttttcat gtcttctgta tgagccttt      2400
```

```
aggaaatata ctgcatttac aataccagca gtaaataatc aaggaccagg agtgaggtat    2460
caatataatg tgctgcctca gggatggaag ggatctcccg ccatctttca ggcatcagcc    2520
aataagatct tacagccatt tagggaagag aatccagatg tcatcattta ccagtacatg    2580
gatgatctct tgtaggctc agatagaaca aagttggaac atgacaaaat gatcaaacaa    2640
ttaagagatc atctactgtt ctggggcttt gagaccccag acaaaaaatt tcaggataaa    2700
cctccatatt tgtggatggg gtatgagctg cacccaaaaa gttggacagt acaggagatc    2760
aagttaccag agaaagaaga atggacagtt aacgatattc agaaattagt aggaaagtta    2820
aactgggcaa gtcaaattta cagtgggcta aggactaagg aattgtgcaa gttgataagg    2880
ggagcaaaag cattagatga aaaagtagaa atgacaaaag aagcagaaat agaatatgaa    2940
gaaaacaaga tgattctaaa agaaagttg catggggtgt attatgatga aaagaaaccc    3000
ttagtggcaa acattcagaa gttagaaggt ggacagtggt cctatcaaat agaacaggag    3060
tcaggaaaac cactgaaaac aggcaaatat gctaagcaga aaacagcaca caccaatgaa    3120
attagaatgc tggcagggtt agtacaaaaa attgcaaaag aagccatagt tatttgggga    3180
aggctgccaa cattcagact gccaatagag agagaggtat gggactaatg gcggtcccaa    3240
tactggcagg ttacctggat accagattgg gaatttgtta gcacaccacc tcttattaga    3300
ctcgggtaca acctagttaa ggatcccata ccaggagagg aagtctacta tgtggatggg    3360
gcagctaaca gaaatagtaa aataggaaag gcgggatatg ttacaaatag aggaaaagaa    3420 aagtaaaag aattagaaga aactactaat caaaagcag aattagaagc agtattactg    3480
gcattaaaag attcagggcc taaagtaaac atagtcacag attcacagta tgtttatgga    3540
attctagaag cacaaccaga tactagtgac tcaggggttag tgacagaaat tataaatcag    3600
atgataggga agaagcagt gtaccttttcc tgggtgcccg cacataaggg catcggagga    3660
aatgaggaag tagataaatt agttagtaaa ggaatcagac aggtactgtt cctagatggg    3720
atagaaaaag cacaagaaga acatgaaaag tatcataata attggagagc attggcagaa    3780
gattttcaaa ttccacaaat agtggcaaaa gaaatagtag cacagtgtcc aaaatgtcaa    3840
gtaaaggggg aagcaatcca tggcaagtg gatgcaagtc cagggacttg gcaaatggac    3900
tgcacacatt tggaaggaaa aataatcata gtagcagtcc atgtggcaag tggatatata    3960
gaggcagaag taataccagc agaaacagga aaagagacag cacatttcct gttgaaacta    4020
gcagcaagat ggccagtaag gaagctacac acagataatg gagcaaattt cacaagtgca    4080
gcagtacagg cggtctgctg gtgggctcag atagagcacg cctttggagt accttacaat    4140
cctcaaagtc aaggagtagt ggaaagcatg aataaacaat taaaaataat catagaacaa    4200
gtaagagaac aagcagaaaa attagaaaca gcagtccaaa tggcagtttt ggttcacaat    4260
tttaaaagaa aaggggggat tggggggtac agtgcaggag aaagaataat agatataata    4320
gcaacagact tagcaaccaa taaattacaa aatcaaattt caaaaattca aattttcgg    4380 gtttattaca gagaaggaag ggatcaactg tggagaggtc cagctaagct gatctggaaa    4440
ggagaaggag cagtagtcat ccaggaggag actggagact tgaaggtagt ccccaggaga    4500
aaagcaaaaa tcataaaaga atatggcaga aaagatgtgg atagtgaggc caatttggcg    4560
ggtagacagg aggaaaattg aacaatggca ctctttggta aaatatcatc agtacaaagg    4620
aaagaaagca gcaaaagagt gggagtatgt gcctcacttt aaagtaccat ggggatggtg    4680
gtcgcattca gaagttcaca tacctttaga ggaaggatca aagttaaaaa taaccaccta    4740
ttggaatttg acagtagaaa agggatggct agggacatat ggggtaggaa tcttatggat    4800
```

```
aaaaggagat tatgtaacag atgtatttcc ttggactgca gatagtttaa tacataaaat    4860
ttattttcca tgttttacag atagagcaat cagacaaagt ctactagggg aaaaagttct    4920
agtgtgtgcc ttccaagggg gacatagaga tcaggtaggg actctgcaat ttttggcaat    4980
acaagcgtgg gctaaaagtc agttagatag gtatggcaga aagagccccc gaggtcccca    5040
ctggggctgg agaagcagag ttccagcctt ggctacggga catgctagaa aaggtcaact    5100
tggaagccag gttacacttt catccagagt tcattttccg tctgtggcgc acttgtgtgg    5160
aacactggca tgacgtacat cagagaagtt tagaatatgc tgcttatagg tacttactgc    5220
tgatgcaaaa ggctttgttt atccactgtc agacagggtg tagtcagaga catggaccca    5280
atcctagggc agtaggagaa aggataacca tcctaccggg gatgtaatga tggccctctc    5340
tttacagaga tggagctgcc ccctgaggat gaaggtccgc aacgagaacc ttatgatgaa    5400
tggttaatgg ataccctaat agagttgcaa gaagaagcta agaaacattt tacatatgct    5460
ttgctaacgc aaataggaga ttatgtatat gagcaacatg gggatagcat agagggagtg    5520
caggcaatga ttcggctgct tcaaagagcc ttgtttcttc attttagaaa tggatgtgca    5580
gggagtagga ttggaacatc cagaggaagt aatcctctac gatccattcc gcaaacgaga    5640
aacatcatgt aacacttgtt attgtaaaaa atgttgttat cactgccaac tctgcttcct    5700
gcagaaagga ctaggcataa attatgcttc cagggcaaga cgaagaagat ctaaggaaga    5760
aaataaggct gataaatttc ctgtacctaa tcagtaagta tggagtgccc tggactagta    5820
ctgcttttag agcctcagct aaaaaggttt ttatagatct tttagttaca ataattaaag    5880
gaaaatagaa taagataaga tggataagaa attagtaata gtattaatag tagtaatagg    5940
gataatacta gtacaaggat cacaaaaacc gcaatatata acagtcttct atggtgtccc    6000
agtatggaga aacagcacag tgcctatgtt ttgtgtgact gataatactc aatcatgggg    6060
aactctaaat tgtataccag agggaggaat atctccagag gtttcaataa atgtgtcaga    6120
acgatttgat gcttggaata atagcttata tgaacaagca aaagataatg tgtggaatct    6180
ttatgattcc actctaaaac catgtgtcag attaagccca ttatgtatta ccatgaattg    6240
ttcagcaata aatggtagct gggatggaat ccctacctca gcaccaccaa caacaacaaa    6300
aacaacaaca caaagaacta taggtgtaga aaaggaatgt actgctggca acgaaacatg    6360
tgaggaagtt caggatgcag atgtgatgtc ttgtgaattt gctgtagcag gactaaagag    6420
agatgagaaa cacaagtata atgatacctg gtattctaga gaccttttggt gtgaaaagga    6480 aacaaattct acaaattcta caaaaaagaa atgttttgta aggcactgca atacaacttc    6540
catacaacaa ttttgtgaac caaagtactg ggaaccattt aggttaagat attgtgctcc    6600
accagggttt gccttactgg tctgcaaaga taaaaattat acaggctttg atacctgtgt    6660
taatgttact gccacttcat gcacacatat gattaatact actgtggcct cagggtttgg    6720
attaaatgga tcaattaatg taaatgagac ttggatatat cagagaaggc aaagtaatag    6780
gacagttata ggtctcaata gttttttataa tttgtcagta acatgcagga gaccttcaaa    6840
tagaacagtg aaagggatat cgctagcaac aggagtcttt atctcactaa gagtagagaa    6900
gagaccaaaa ggagcttggt gtagatttga agggaattgg acggatgcat ggaaagaagt    6960
aaaagagaga gtgaaaacaa caaagggta tcgaggtact agtaacacag acaaaataaa    7020
gataagaaca gtatatggtg gagatgatga ggcaagatat ttctggctaa attgtaatgg    7080
agaattttta tattgcaagt taaattggtt tttaaatttg ttaaataatg agacagtagg    7140
```

```
gacaacaaat gagaagagaa aagcacctttt tgtaccatgc atcacaaaaa tgatagtcaa    7200
tgattggtat acagtatcga ggaaggtata cacgccaccg aggccagatg cgttaaagtg    7260
cagtgcacag gtatcctatc tgttggcaga catagactat attaatgaca gtgagacaaa    7320
catcaccctc tcagcggaag tgggtgatta ttgggcagca gaattgggga gatataaggc    7380
aatagaaatc agaccaattg gctttgcacc aacagaaata aaaaggtacc agacgaaaca    7440
gaaaagggta cctttggtgc tgggttttct aggtttcctc tcagcagcag gtactgcaat    7500
gggcgcagcg gcgacagccc tgactgtcca gtcccggcat ttgcttgcag ggatattgca    7560
gcagcaaaag aacctgctgg acatagttaa gcggcagcag aatctgctaa agctcaccgt    7620
ctggggaact aaaaatctcc aggcgcgtgt cactgctatt gagaaatacc tagcagacca    7680
atctctattg aatacatttg ggtgtgcctg gagacaagtc tgccatacag tggtgccgtg    7740
gacattcaac aaaacgcctg agtggcagaa agaatcatgg ttgcagtggg aaagaaatat    7800
ctcttattta gaggctaaca ttacaatagc attacaggag gcccaggatc aacatgagaa    7860
aaatgtgcat gaattggaga aattaagtaa ttggggagat gcattcagtt ggctgaatct    7920
tgactggtgg atgcaatata taaaaatagg cttctttata gtaataggta tcataggatt    7980
aagagtagct tggctgttat ggaattgtct tagtaatctt aggcaagggt ataggcctct    8040
ctccccaccc tcttatgttc agcagatcca tatccacaac acgggggaac cgcaaactcc    8100
aggagaaaaa agagaagacg gtggagaaga aggtggcaac aagtacaaca attggctgag    8160
agaatattgc tggattcaac tgatccaccc gttgagcagg atttgacgc agctatcgca    8220
gatttgcaga agctgcagct caataatctt ccagagcctc cggtggattt tagctaagat    8280
acaatatggg tggcaagagt tcaaagaatt cagcagctgg tttgctgaga tggcgcttca    8340
aaatgcttac tacacctgga gagggttatg tgcggtggca cgagactttg ctggatggcc    8400
agccatggtg tgcagaagga tcaggcaggg cctcgagaga ctttgtaatt agaggaggca    8460
ttacagcaga aacgcaagct tcaatagatg acattgactg gtatgaagat actgatgaca    8520
ccttggtagg atttccagtg aaacctcaag taccacttag accaatgagt tacaagctag    8580
caatagacat gtctcacttt ttaaaagaaa agggggggact ggaagggatt tattggagta    8640
tcagaagaca aagaatattg gatatgtacc tggaaaatga gcatggcata atacctgatt    8700
ggcaaaacta cactccaggg ccaggaataa gatatccaac actgtttgga tggctctggc    8760
aattggtgcc agtagatgta tctgatgaag caagagaaga tgaagagcat agtttgctac    8820
atccagcaga aacaagtggg atggaagacc catgggggga ggtcttggcc tggaagtttg    8880
atcctatgct ggcagtagat tacataggct atagactgca tccagagttc tttggggaaa    8940
ggaagaacaa gacccagtaa ccacatcctc tggggttgcc ttggtaacca ggcagaagaa    9000
tctgctgatg caaagggac tttccactgg tgcatgcgca ctggggaagg acttttccgg    9060
gatgacgtgg gaggggagt ggtcagccct ctcctgctgc atataagcag ctgctctgcg    9120
cttgtaaaac gggtctctcc ctgggaggct accggattga gcctgggtgt tctctggtaa    9180
gtctctagga actccagctt gagcctgggt gttcgctggt gtctctgaac aggcttgctg    9240
gggtgcctct cgctcttcgg gtagaccgcc agttgaggct cggccggcct caacgggaga    9300
gatcaccgct tgcttatagc cttgaagctc aataaagcat gccagttagt ttactgtaag    9360
caagtgtgtg cctgttttac ctctcagcag ttaacgactc tggggtaggg atccctcaga    9420
ttcttgtggc agaagagcct tgggctaaga aaattcccta ccagt                    9465
```

```
<210> SEQ ID NO 2
<211> LENGTH: 25
<212> TYPE: DNA
<213> ORGANISM: Simian immunodeficiency virus
<220> FEATURE:
<223> OTHER INFORMATION: Gag A primer

<400> SEQUENCE: 2
aggttacggc ccggcggaaa gaaaa                                        25

<210> SEQ ID NO 3
<211> LENGTH: 32
<212> TYPE: DNA
<213> ORGANISM: Simian immunodeficiency virus
<220> FEATURE:
<223> OTHER INFORMATION: Gag B primer

<400> SEQUENCE: 3
cctactccct gacaggccgt cagcatttct tc                                32

<210> SEQ ID NO 4
<211> LENGTH: 28
<212> TYPE: DNA
<213> ORGANISM: Simian immunodeficiency virus
<220> FEATURE:
<223> OTHER INFORMATION: Gag 1 primer

<400> SEQUENCE: 4
ttagagaacc aacaggaagt cacatagc                                     28

<210> SEQ ID NO 5
<211> LENGTH: 25
<212> TYPE: DNA
<213> ORGANISM: Simian immunodeficiency virus
<220> FEATURE:
<223> OTHER INFORMATION: Gag 2 primer

<400> SEQUENCE: 5
tccacagttg atcccttcct tctct                                        25

<210> SEQ ID NO 6
<211> LENGTH: 23
<212> TYPE: DNA
<213> ORGANISM: Simian immunodeficiency virus
<220> FEATURE:
<223> OTHER INFORMATION: Gag r1 primer

<400> SEQUENCE: 6
tcggaactag aggcagcagg act                                          23

<210> SEQ ID NO 7
<211> LENGTH: 25
<212> TYPE: DNA
<213> ORGANISM: Simian immunodeficiency virus
<220> FEATURE:
<223> OTHER INFORMATION: Gag r2 primer

<400> SEQUENCE: 7
ctagcagcaa gatggccagt aagga                                        25

<210> SEQ ID NO 8
<211> LENGTH: 23
<212> TYPE: DNA
<213> ORGANISM: Simian immunodeficiency virus
<220> FEATURE:
<223> OTHER INFORMATION: UNIPOL1 primer
```

-continued

<400> SEQUENCE: 8
agtggattca tagaagcaga agt                                                    23

<210> SEQ ID NO 9
<211> LENGTH: 19
<212> TYPE: DNA
<213> ORGANISM: Simian immunodeficiency virus
<220> FEATURE:
<223> OTHER INFORMATION: SS2 primer

<400> SEQUENCE: 9
tactgcccct tcacctttc                                                         19

<210> SEQ ID NO 10
<211> LENGTH: 850
<212> TYPE: PRT
<213> ORGANISM: Simian immunodeficiency virus
<220> FEATURE:
<223> OTHER INFORMATION: Amino acid sequence of homologous region of
      SIVrcm lentiviral env protein

<400> SEQUENCE: 10

```
Met Asp Lys Lys Leu Val Ile Val Leu Ile Val Val Ile Gly Ile Ile
  1               5                  10                  15

Leu Val Gln Gly Ser Gln Lys Pro Gln Tyr Ile Thr Val Phe Tyr Gly
             20                  25                  30

Val Pro Val Trp Arg Asn Ser Thr Val Pro Met Phe Cys Val Thr Asp
         35                  40                  45

Asn Thr Gln Ser Trp Gly Thr Leu Asn Cys Ile Pro Glu Gly Gly Ile
     50                  55                  60

Ser Pro Glu Val Ser Ile Asn Val Ser Glu Arg Phe Asp Ala Trp Asn
 65                  70                  75                  80

Asn Ser Leu Tyr Glu Gln Ala Lys Asp Asn Val Trp Asn Leu Tyr Asp
                 85                  90                  95

Ser Thr Leu Lys Pro Cys Val Arg Leu Ser Pro Leu Cys Ile Thr Met
            100                 105                 110

Asn Cys Ser Ala Ile Asn Gly Ser Trp Asp Gly Ile Pro Thr Ser Ala
        115                 120                 125

Pro Pro Thr Thr Thr Lys Thr Thr Thr Gln Arg Thr Ile Gly Val Glu
    130                 135                 140

Lys Glu Cys Thr Ala Gly Asn Glu Thr Cys Glu Glu Val Gln Asp Ala
145                 150                 155                 160

Asp Val Met Ser Cys Glu Phe Ala Val Ala Gly Leu Lys Arg Asp Glu
                165                 170                 175

Lys His Lys Tyr Asn Asp Thr Trp Tyr Ser Arg Asp Leu Trp Cys Glu
            180                 185                 190

Lys Glu Thr Asn Ser Thr Asn Ser Thr Lys Lys Cys Phe Val Arg
        195                 200                 205

His Cys Asn Thr Thr Ser Ile Gln Gln Phe Cys Glu Pro Lys Tyr Trp
    210                 215                 220

Glu Pro Phe Arg Leu Arg Tyr Cys Ala Pro Pro Gly Phe Ala Leu Leu
225                 230                 235                 240

Val Cys Lys Asp Lys Asn Tyr Thr Gly Phe Asp Thr Cys Val Asn Val
                245                 250                 255

Thr Ala Thr Ser Cys Thr His Met Ile Asn Thr Thr Val Ala Ser Gly
            260                 265                 270

Phe Gly Leu Asn Gly Ser Ile Asn Val Asn Glu Thr Trp Ile Tyr Gln
```

-continued

```
              275                 280                 285
Arg Arg Gln Ser Asn Arg Thr Val Ile Gly Leu Asn Ser Phe Tyr Asn
    290                 295                 300

Leu Ser Val Thr Cys Arg Arg Pro Ser Asn Arg Thr Val Lys Gly Ile
305                 310                 315                 320

Ser Leu Ala Thr Gly Val Phe Ile Ser Leu Arg Val Glu Lys Arg Pro
                325                 330                 335

Lys Gly Ala Trp Cys Arg Phe Glu Gly Asn Trp Thr Asp Ala Trp Lys
                340                 345                 350

Glu Val Lys Glu Arg Val Lys Thr Thr Lys Gly Tyr Arg Gly Thr Ser
                355                 360                 365

Asn Thr Asp Lys Ile Lys Ile Arg Thr Val Tyr Gly Gly Asp Asp Glu
    370                 375                 380

Ala Arg Tyr Phe Trp Leu Asn Cys Asn Gly Glu Phe Leu Tyr Cys Lys
385                 390                 395                 400

Leu Asn Trp Phe Leu Asn Leu Asn Asn Glu Thr Val Gly Thr Thr
                405                 410                 415

Asn Glu Lys Arg Lys Ala Pro Phe Val Pro Cys Ile Thr Lys Met Ile
                420                 425                 430

Val Asn Asp Trp Tyr Thr Val Ser Arg Lys Val Tyr Thr Pro Pro Arg
                435                 440                 445

Pro Asp Ala Leu Lys Cys Ser Ala Gln Val Ser Tyr Leu Leu Ala Asp
    450                 455                 460

Ile Asp Tyr Ile Asn Asp Ser Glu Thr Asn Ile Thr Leu Ser Ala Glu
465                 470                 475                 480

Val Gly Asp Tyr Trp Ala Ala Glu Leu Gly Arg Tyr Lys Ala Ile Glu
                485                 490                 495

Ile Arg Pro Ile Gly Phe Ala Pro Thr Glu Ile Lys Arg Tyr Gln Thr
                500                 505                 510

Lys Gln Lys Arg Val Pro Leu Val Leu Gly Phe Leu Gly Phe Leu Ser
                515                 520                 525

Ala Ala Gly Thr Ala Met Gly Ala Ala Thr Ala Leu Thr Val Gln
    530                 535                 540

Ser Arg His Leu Leu Ala Gly Ile Leu Gln Gln Gln Lys Asn Leu Leu
545                 550                 555                 560

Asp Ile Val Lys Arg Gln Gln Asn Leu Leu Lys Leu Thr Val Trp Gly
                565                 570                 575

Thr Lys Asn Leu Gln Ala Arg Val Thr Ala Ile Glu Lys Tyr Leu Ala
                580                 585                 590

Asp Gln Ser Leu Leu Asn Thr Phe Gly Cys Ala Trp Arg Gln Val Cys
    595                 600                 605

His Thr Val Val Pro Trp Thr Phe Asn Lys Thr Pro Glu Trp Gln Lys
610                 615                 620

Glu Ser Trp Leu Gln Trp Glu Arg Asn Ile Ser Tyr Leu Glu Ala Asn
625                 630                 635                 640

Ile Thr Ile Ala Leu Gln Glu Ala Gln Asp His Glu Lys Asn Val
                645                 650                 655

His Glu Leu Glu Lys Leu Ser Asn Trp Gly Asp Ala Phe Ser Trp Leu
                660                 665                 670

Asn Leu Asp Trp Trp Met Gln Tyr Ile Lys Ile Gly Phe Phe Ile Val
                675                 680                 685

Ile Gly Ile Ile Gly Leu Arg Val Ala Trp Leu Leu Trp Asn Cys Leu
690                 695                 700
```

```
Ser Asn Leu Arg Gln Gly Tyr Arg Pro Leu Ser Pro Pro Ser Tyr Val
705                 710                 715                 720

Gln Gln Ile His Ile His Asn Thr Gly Glu Pro Gln Thr Pro Gly Glu
            725                 730                 735

Lys Arg Glu Asp Gly Gly Glu Gly Gly Asn Lys Tyr Asn Asn Trp
        740                 745                 750

Leu Arg Glu Tyr Cys Trp Ile Gln Leu Ile His Pro Leu Ser Arg Ile
            755                 760                 765

Trp Thr Gln Leu Ser Gln Ile Cys Arg Ser Cys Ser Ser Ile Ile Phe
    770                 775                 780

Gln Ser Leu Arg Trp Ile Leu Ala Lys Ile Gln Tyr Gly Trp Gln Glu
785                 790                 795                 800

Phe Lys Glu Phe Ser Ser Trp Phe Ala Glu Met Ala Leu Gln Asn Ala
                805                 810                 815

Tyr Tyr Thr Trp Arg Gly Leu Cys Ala Val Ala Arg Asp Phe Ala Gly
            820                 825                 830

Trp Pro Ala Met Val Cys Arg Arg Ile Arg Gln Gly Leu Glu Arg Leu
        835                 840                 845

Cys Asn
    850

<210> SEQ ID NO 11
<211> LENGTH: 855
<212> TYPE: PRT
<213> ORGANISM: Simian immunodeficiency virus
<220> FEATURE:
<223> OTHER INFORMATION: Amino acid sequence of homologous region of
      A_U455 lentiviral env protein

<400> SEQUENCE: 11

Met Arg Val Met Gly Ile Gln Arg Asn Tyr Pro Cys Leu Trp Arg Trp
1               5                   10                  15

Gly Thr Met Ile Leu Gly Leu Ile Ile Ile Cys Asn Ala Gln Gln Leu
            20                  25                  30

Trp Val Thr Val Tyr Tyr Gly Val Pro Val Trp Lys Asp Ala Val Thr
        35                  40                  45

Thr Leu Phe Cys Ala Ser Asp Ala Lys Ala Tyr Asp Ala Glu Val His
    50                  55                  60

Asn Val Trp Ala Thr His Ala Cys Val Pro Thr Asp Pro Asn Pro Gln
65                  70                  75                  80

Glu Ile Asp Leu Val Asn Val Thr Glu Glu Phe Asn Met Trp Lys Asn
                85                  90                  95

Asn Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asp
        115                 120                 125

Cys His Asn Ile Thr Ile Asn Asn Thr Asn Asn Thr Asn Ile Thr
    130                 135                 140

Asp Gly Val Arg Glu Glu Met Lys Asn Cys Ser Phe Asn Met Thr Thr
145                 150                 155                 160

Glu Leu Arg Asp Lys Lys Gln Lys Val Tyr Ser Leu Phe Tyr Arg Leu
                165                 170                 175

Asp Ile Val Gln Ile Asn Lys Ser Asp Asn Asn Ser Tyr Arg Leu Ile
            180                 185                 190

Asn Cys Asn Thr Ser Thr Ile Thr Gln Ala Cys Pro Lys Val Ser Phe
```

```
                195                 200                 205
Glu Pro Ile Pro Ile His Tyr Cys Ala Pro Ala Gly Phe Ala Ile Leu
            210                 215                 220
Lys Cys Lys Asp Pro Glu Phe Asn Gly Lys Gly Pro Cys Arg Asn Val
225                 230                 235                 240
Ser Thr Val Gln Cys Thr His Gly Ile Lys Pro Val Val Ser Thr Gln
                245                 250                 255
Leu Leu Leu Asn Gly Ser Leu Ala Glu Arg Glu Ile Arg Ile Arg Ser
            260                 265                 270
Glu Asn Phe Thr Asn Asn Ala Lys Thr Ile Ile Val Gln Leu Val Asn
                275                 280                 285
Pro Val Lys Ile Asn Cys Ser Arg Pro Tyr Asn Thr Arg Lys Asn Ile
            290                 295                 300
Arg Arg Tyr Ser Ile Gly Ser Gly Gln Ala Phe Tyr Val Thr Gly Lys
305                 310                 315                 320
Ile Ile Gly Asp Ile Arg Gln Ala His Cys Asn Val Ser Arg Arg Asp
                325                 330                 335
Trp Asn Arg Thr Ile Gln Gln Val Ala Glu Gln Leu Lys Lys Lys Phe
            340                 345                 350
Asn Asn Lys Thr Ile Ile Phe Ala Ser Ser Ser Gly Gly Asp Ile Glu
            355                 360                 365
Ile Thr Thr His Ser Phe Asn Cys Gly Gly Glu Phe Phe Tyr Cys Asn
            370                 375                 380
Thr Ser Gly Leu Phe Asn Ser Ile Trp Asn Gly Ser Met Ser Asn Asp
385                 390                 395                 400
Met Gly Pro Asn Gly Thr Ile Thr Leu Gln Cys Arg Ile Lys Gln Ile
                405                 410                 415
Ile Asn Met Trp Gln Arg Val Gly Gln Ala Met Tyr Ala Pro Pro Ile
            420                 425                 430
Gln Gly Val Ile Arg Cys Glu Ser Asn Ile Thr Gly Leu Leu Leu Thr
            435                 440                 445
Arg Asp Gly Gly Thr Asn Asn Thr Lys Asn Glu Thr Phe Arg Pro Gly
450                 455                 460
Gly Gly Asp Met Arg Asp Asn Trp Lys Ser Glu Leu Tyr Lys Tyr Lys
465                 470                 475                 480
Val Val Lys Ile Glu Pro Leu Gly Val Ala Pro Thr Arg Ala Lys Arg
                485                 490                 495
Arg Val Val Glu Arg Glu Lys Arg Ala Val Gly Leu Gly Ala Ile Phe
            500                 505                 510
Leu Gly Phe Leu Gly Ala Ala Gly Ser Thr Met Gly Ala Ala Ser Ile
            515                 520                 525
Thr Leu Thr Val Gln Ala Arg Gln Leu Leu Ser Gly Ile Val Gln Gln
            530                 535                 540
Gln Ser Asn Leu Leu Arg Ala Ile Glu Ala Gln Gln His Leu Leu Lys
545                 550                 555                 560
Leu Thr Val Trp Gly Ile Lys Gln Leu Gln Ala Arg Val Leu Ala Val
                565                 570                 575
Glu Arg Tyr Leu Gln Asp Gln Gln Leu Leu Gly Ile Trp Gly Cys Ser
            580                 585                 590
Gly Lys Leu Ile Cys Thr Thr Thr Val Pro Trp Asn Ser Ser Trp Ser
            595                 600                 605
Asn Lys Ser Gln Glu Asp Ile Trp Asn Asn Met Thr Trp Leu Gln Trp
610                 615                 620
```

-continued

```
Glu Lys Glu Ile Ser Ser Tyr Thr Gly Ile Ile Tyr Gln Leu Ile Glu
625                 630                 635                 640

Glu Ser Gln Asn Gln Gln Glu Lys Asn Glu Leu Asp Leu Leu Ala Leu
                645                 650                 655

Asp Lys Trp Ala Asn Leu Asn Trp Phe Asn Ile Ser Asn Trp Leu Trp
            660                 665                 670

Tyr Ile Arg Leu Phe Val Ile Ile Val Gly Gly Leu Ile Gly Leu Arg
        675                 680                 685

Ile Val Phe Thr Val Leu Ser Ile Ile Asn Arg Val Arg Gln Gly Tyr
    690                 695                 700

Ser Pro Leu Ser Phe Gln Thr Leu Ala Pro Ile Pro Glu Gly Leu Gly
705                 710                 715                 720

Arg Pro Gly Arg Ile Glu Glu Glu Gly Gly Glu Gln Gly Lys Asp Arg
                725                 730                 735

Ser Ile Arg Leu Val Ser Gly Phe Leu Ala Ile Ala Trp Asp Asp Leu
            740                 745                 750

Arg Asn Leu Cys Leu Phe Ser Tyr His Arg Leu Arg Asp Phe Ala Leu
        755                 760                 765

Ile Val Ala Arg Ala Val Glu Leu Leu Gly Arg Ser Ser Leu Lys Gly
    770                 775                 780

Leu Arg Leu Gly Trp Glu Gly Leu Lys Tyr Leu Trp Asn Leu Leu Leu
785                 790                 795                 800

Tyr Trp Gly Arg Glu Leu Lys Ile Ser Ala Ile Thr Leu Leu Asp Ala
                805                 810                 815

Val Ala Val Ala Val Ala Gly Trp Ile Asp Arg Val Ile Glu Ile Gly
            820                 825                 830

Gln Thr Ile Gly Arg Ala Ile Leu Asn Ile Pro Arg Arg Ile Arg Gln
        835                 840                 845

Gly Leu Glu Arg Ala Leu Leu
    850                 855

<210> SEQ ID NO 12
<211> LENGTH: 855
<212> TYPE: PRT
<213> ORGANISM: Simian immunodeficiency virus
<220> FEATURE:
<223> OTHER INFORMATION: Amino acid sequence of homologous region of
      B_HXB2R lentiviral env protein

<400> SEQUENCE: 12

Met Arg Val Met Gly Ile Gln Arg Asn Tyr Pro Cys Leu Trp Arg Trp
  1               5                  10                  15

Gly Thr Met Ile Leu Gly Leu Ile Ile Ile Cys Asn Ala Gln Gln Leu
             20                  25                  30

Trp Val Thr Val Tyr Tyr Gly Val Pro Val Trp Lys Asp Ala Val Thr
         35                  40                  45

Thr Leu Phe Cys Ala Ser Asp Ala Lys Ala Tyr Asp Ala Glu Val His
     50                  55                  60

Asn Val Trp Ala Thr His Ala Cys Val Pro Thr Asp Pro Asn Pro Gln
 65                  70                  75                  80

Glu Ile Asp Leu Val Asn Val Thr Glu Glu Phe Asn Met Trp Lys Asn
                 85                  90                  95

Asn Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asp
```

```
            115                 120                 125
Cys His Asn Ile Thr Ile Asn Asn Thr Asn Asn Asn Thr Asn Ile Thr
            130                 135                 140

Asp Gly Val Arg Glu Glu Met Lys Asn Cys Ser Phe Asn Met Thr Thr
145                 150                 155                 160

Glu Leu Arg Asp Lys Lys Gln Lys Val Tyr Ser Leu Phe Tyr Arg Leu
                165                 170                 175

Asp Ile Val Gln Ile Asn Lys Thr Asp Asn Asn Ser Tyr Arg Leu Ile
            180                 185                 190

Asn Cys Asn Thr Ser Thr Ile Thr Gln Ala Cys Pro Lys Val Ser Phe
            195                 200                 205

Glu Pro Ile Pro Ile His Tyr Cys Ala Pro Ala Gly Phe Ala Ile Leu
210                 215                 220

Lys Cys Lys Asp Pro Glu Phe Asn Gly Lys Gly Pro Cys Arg Asn Val
225                 230                 235                 240

Ser Thr Val Gln Cys Thr His Gly Ile Lys Pro Val Val Ser Thr Gln
                245                 250                 255

Leu Leu Leu Asn Gly Ser Leu Ala Glu Arg Glu Ile Arg Ile Arg Ser
            260                 265                 270

Glu Asn Phe Thr Asn Asn Ala Lys Thr Ile Ile Val Gln Leu Val Asn
            275                 280                 285

Pro Val Lys Ile Asn Cys Ser Arg Pro Tyr Asn Thr Arg Lys Asn Ile
            290                 295                 300

Arg Arg Tyr Ser Ile Gly Ser Gly Gln Ala Phe Tyr Val Thr Gly Lys
305                 310                 315                 320

Ile Ile Gly Asp Ile Arg Gln Ala His Cys Asn Val Ser Arg Arg Asp
                325                 330                 335

Trp Asn Arg Thr Ile Gln Gln Val Ala Glu Gln Leu Lys Lys Lys Phe
            340                 345                 350

Asn Asn Lys Thr Ile Ile Phe Ala Ser Ser Ser Gly Gly Asp Ile Glu
            355                 360                 365

Ile Thr Thr His Ser Phe Asn Cys Gly Gly Glu Phe Phe Tyr Cys Asn
            370                 375                 380

Thr Ser Gly Leu Phe Asn Ser Ile Trp Asn Gly Ser Met Ser Asn Asp
385                 390                 395                 400

Met Gly Pro Asn Gly Thr Ile Thr Leu Gln Cys Arg Ile Lys Gln Ile
                405                 410                 415

Ile Asn Met Trp Gln Arg Val Gly Gln Ala Met Tyr Ala Pro Pro Ile
            420                 425                 430

Gln Gly Val Ile Arg Cys Glu Ser Asn Ile Thr Gly Leu Leu Leu Thr
            435                 440                 445

Arg Asp Gly Gly Thr Asn Asn Thr Lys Asn Glu Thr Phe Arg Pro Gly
450                 455                 460

Gly Gly Asp Met Arg Asp Asn Trp Lys Ser Glu Leu Tyr Lys Tyr Lys
465                 470                 475                 480

Val Val Lys Ile Glu Pro Leu Gly Val Ala Pro Thr Arg Ala Lys Arg
                485                 490                 495

Arg Val Val Glu Arg Glu Lys Arg Ala Val Gly Leu Gly Ala Ile Phe
            500                 505                 510

Leu Gly Phe Leu Gly Ala Ala Gly Ser Thr Met Gly Ala Ala Ser Ile
            515                 520                 525

Thr Leu Thr Val Gln Ala Arg Gln Leu Leu Ser Gly Ile Val Gln Gln
530                 535                 540
```

-continued

```
Gln Ser Asn Leu Leu Arg Ala Ile Glu Ala Gln Gln His Leu Leu Lys
545                 550                 555                 560

Leu Thr Val Trp Gly Ile Lys Gln Leu Gln Ala Arg Val Leu Ala Val
                565                 570                 575

Glu Arg Tyr Leu Gln Asp Gln Gln Leu Leu Gly Ile Trp Gly Cys Ser
            580                 585                 590

Gly Lys Leu Ile Cys Thr Thr Thr Val Pro Trp Asn Ser Ser Trp Ser
        595                 600                 605

Asn Lys Ser Gln Glu Asp Ile Trp Asn Asn Met Thr Trp Leu Gln Trp
    610                 615                 620

Glu Lys Glu Ile Ser Ser Tyr Thr Gly Ile Ile Tyr Gln Leu Ile Glu
625                 630                 635                 640

Glu Ser Gln Asn Gln Gln Glu Lys Asn Glu Leu Asp Leu Leu Ala Leu
                645                 650                 655

Asp Lys Trp Ala Asn Leu Asn Trp Phe Asn Ile Ser Asn Trp Leu Trp
            660                 665                 670

Tyr Ile Arg Leu Phe Val Ile Ile Val Gly Gly Leu Ile Gly Leu Arg
        675                 680                 685

Ile Val Phe Thr Val Leu Ser Ile Ile Asn Arg Val Arg Gln Gly Tyr
    690                 695                 700

Ser Pro Leu Ser Phe Gln Thr Leu Ala Pro Ile Pro Glu Gly Leu Gly
705                 710                 715                 720

Arg Pro Gly Arg Ile Glu Glu Glu Gly Gly Glu Gln Gly Lys Asp Arg
                725                 730                 735

Ser Ile Arg Leu Val Ser Gly Phe Leu Ala Ile Ala Trp Asp Asp Leu
            740                 745                 750

Arg Asn Leu Cys Leu Phe Ser Tyr His Arg Leu Arg Asp Phe Ala Leu
        755                 760                 765

Ile Val Ala Arg Ala Val Glu Leu Leu Gly Arg Ser Ser Leu Lys Gly
    770                 775                 780

Leu Arg Leu Gly Trp Glu Gly Leu Lys Tyr Leu Trp Asn Leu Leu Leu
785                 790                 795                 800

Tyr Trp Gly Arg Glu Leu Lys Ile Ser Ala Ile Thr Leu Leu Asp Ala
                805                 810                 815

Val Ala Val Ala Val Ala Gly Trp Ile Asp Arg Val Ile Glu Ile Gly
            820                 825                 830

Gln Thr Ile Gly Arg Ala Ile Leu Asn Ile Pro Arg Arg Ile Arg Gln
        835                 840                 845

Gly Leu Glu Arg Ala Leu Leu
    850                 855

<210> SEQ ID NO 13
<211> LENGTH: 853
<212> TYPE: PRT
<213> ORGANISM: Simian immunodeficiency virus
<220> FEATURE:
<223> OTHER INFORMATION: Amino acid sequence of homologous region of
      D_ELI lentiviral env protein

<400> SEQUENCE: 13

Met Arg Ala Arg Gly Ile Glu Arg Asn Cys Gln Asn Trp Trp Lys Trp
  1               5                  10                  15

Gly Ile Met Leu Leu Gly Ile Leu Met Thr Cys Ser Ala Ala Asp Asn
            20                  25                  30

Leu Trp Val Thr Val Tyr Tyr Gly Val Pro Val Trp Lys Glu Ala Thr
```

-continued

```
             35                  40                  45
Thr Thr Leu Phe Cys Ala Ser Asp Ala Lys Ser Tyr Glu Thr Glu Ala
         50                  55                  60
His Asn Ile Trp Ala Thr His Ala Cys Val Pro Thr Asp Pro Asn Pro
 65                  70                  75                  80
Gln Glu Ile Ala Leu Glu Asn Val Thr Glu Asn Phe Asn Met Trp Lys
                 85                  90                  95
Asn Asn Met Val Glu Gln Met His Glu Asp Ile Ile Ser Leu Trp Asp
                100                 105                 110
Gln Ser Leu Lys Pro Cys Val Lys Leu Thr Pro Leu Cys Val Thr Leu
                115                 120                 125
Asn Cys Ser Asp Glu Leu Arg Asn Asn Gly Thr Met Gly Asn Asn Val
130                 135                 140
Thr Thr Glu Glu Lys Gly Met Lys Asn Cys Ser Phe Asn Val Thr Thr
145                 150                 155                 160
Val Leu Lys Asp Lys Lys Gln Gln Val Tyr Ala Leu Phe Tyr Arg Leu
                165                 170                 175
Asp Ile Val Pro Ile Asp Asn Asp Ser Ser Thr Asn Ser Thr Asn Tyr
                180                 185                 190
Arg Leu Ile Asn Cys Asn Thr Ser Ala Ile Thr Gln Ala Cys Pro Lys
                195                 200                 205
Val Ser Phe Glu Pro Ile Pro Ile His Tyr Cys Ala Pro Ala Gly Phe
210                 215                 220
Ala Ile Leu Lys Cys Arg Asp Lys Lys Phe Asn Gly Thr Gly Pro Cys
225                 230                 235                 240
Thr Asn Val Ser Thr Val Gln Cys Thr His Gly Ile Arg Pro Val Val
                245                 250                 255
Ser Thr Gln Leu Leu Leu Asn Gly Ser Leu Ala Glu Glu Val Ile
                260                 265                 270
Ile Arg Ser Glu Asn Leu Thr Asn Asn Ala Lys Asn Ile Ile Ala His
                275                 280                 285
Leu Asn Glu Ser Val Lys Ile Thr Cys Ala Arg Pro Tyr Gln Asn Thr
290                 295                 300
Arg Gln Arg Thr Pro Ile Gly Leu Gly Gln Ser Leu Tyr Thr Thr Arg
305                 310                 315                 320
Ser Arg Ser Ile Ile Gly Gln Ala His Cys Asn Ile Ser Arg Ala Gln
                325                 330                 335
Trp Ser Lys Thr Leu Gln Gln Val Ala Arg Lys Leu Gly Thr Leu Leu
                340                 345                 350
Asn Lys Thr Ile Ile Lys Phe Lys Pro Ser Ser Gly Gly Asp Pro Glu
                355                 360                 365
Ile Thr Thr His Ser Phe Asn Cys Gly Gly Glu Phe Phe Tyr Cys Asn
        370                 375                 380
Thr Ser Gly Leu Phe Asn Ser Thr Trp Asn Ile Ser Ala Trp Asn Asn
385                 390                 395                 400
Ile Thr Glu Ser Asn Asn Ser Thr Asn Thr Asn Ile Thr Leu Gln Cys
                405                 410                 415
Arg Ile Lys Gln Ile Ile Lys Met Val Ala Gly Arg Lys Ala Ile Tyr
                420                 425                 430
Ala Pro Pro Ile Glu Arg Asn Ile Leu Cys Ser Ser Asn Ile Thr Gly
                435                 440                 445
Leu Leu Leu Thr Arg Asp Gly Gly Ile Asn Asn Ser Thr Asn Glu Thr
450                 455                 460
```

-continued

```
Phe Arg Pro Gly Gly Asp Met Arg Asp Asn Trp Arg Ser Glu Leu
465                 470                 475                 480

Tyr Lys Tyr Lys Val Val Gln Ile Glu Pro Leu Gly Val Ala Pro Thr
            485                 490                 495

Arg Ala Lys Arg Val Val Glu Arg Glu Lys Arg Ala Ile Gly Leu
        500                 505                 510

Gly Ala Met Phe Leu Gly Phe Leu Gly Ala Ala Gly Ser Thr Met Gly
        515                 520                 525

Ala Arg Ser Val Thr Leu Thr Val Gln Ala Arg Gln Leu Met Ser Gly
530                 535                 540

Ile Val Gln Gln Gln Asn Asn Leu Leu Arg Ala Ile Glu Ala Gln Gln
545                 550                 555                 560

His Leu Leu Gln Leu Thr Val Trp Gly Ile Lys Gln Leu Gln Ala Arg
                565                 570                 575

Ile Leu Ala Val Glu Arg Tyr Leu Lys Asp Gln Gln Leu Leu Gly Ile
            580                 585                 590

Trp Gly Cys Ser Gly Lys His Ile Cys Thr Thr Asn Val Pro Trp Asn
        595                 600                 605

Ser Ser Trp Ser Asn Arg Ser Leu Asn Glu Ile Trp Gln Asn Met Thr
610                 615                 620

Trp Met Glu Trp Glu Arg Glu Ile Asp Asn Tyr Thr Gly Leu Ile Tyr
625                 630                 635                 640

Ser Leu Ile Glu Glu Ser Gln Thr Gln Gln Glu Lys Asn Glu Lys Glu
                645                 650                 655

Leu Leu Glu Leu Asp Lys Trp Ala Ser Leu Trp Asn Trp Phe Ser Ile
            660                 665                 670

Thr Gln Trp Leu Trp Tyr Ile Lys Ile Phe Ile Met Ile Ile Gly Gly
        675                 680                 685

Leu Ile Gly Leu Arg Ile Val Phe Ala Val Leu Ser Leu Val Asn Arg
690                 695                 700

Val Arg Gln Gly Tyr Ser Pro Leu Ser Phe Gln Thr Leu Leu Pro Ala
705                 710                 715                 720

Pro Arg Gly Pro Asp Arg Pro Glu Gly Thr Glu Glu Glu Gly Gly Glu
                725                 730                 735

Arg Gly Arg Asp Arg Ser Val Arg Leu Leu Asn Gly Phe Ser Ala Leu
            740                 745                 750

Ile Trp Asp Asp Leu Arg Ser Leu Cys Leu Phe Ser Tyr His Arg Leu
        755                 760                 765

Arg Asp Leu Ile Leu Ile Ala Val Arg Ile Val Glu Leu Leu Gly Arg
770                 775                 780

Arg Gly Trp Asp Ile Leu Lys Tyr Leu Trp Asn Leu Leu Gln Tyr Trp
785                 790                 795                 800

Ser Gln Glu Leu Arg Asn Ser Ala Ser Ser Leu Phe Asp Ala Ile Ala
                805                 810                 815

Ile Ala Val Ala Glu Gly Thr Asp Arg Val Ile Glu Ile Ile Gln Arg
            820                 825                 830

Ala Cys Arg Ala Val Leu Asn Ile Pro Arg Arg Ile Arg Gln Gly Leu
        835                 840                 845

Glu Arg Ser Leu Leu
    850
```

<210> SEQ ID NO 14
<211> LENGTH: 875

-continued

```
<212> TYPE: PRT
<213> ORGANISM: Simian immunodeficiency virus
<220> FEATURE:
<223> OTHER INFORMATION: Amino acid sequence of homologous region of
      C-MVP5180 lentiviral env protein

<400> SEQUENCE: 14

Met Thr Val Thr Met Lys Val Met Lys Lys Asn Asn Arg Lys Ser Trp
  1               5                  10                  15

Ser Leu Tyr Ile Ala Met Ala Leu Leu Ile Pro Cys Leu Ser Tyr Ser
             20                  25                  30

Lys Gln Leu Tyr Ala Thr Val Tyr Ser Gly Val Pro Val Trp Glu Glu
         35                  40                  45

Ala Ala Pro Val Leu Phe Cys Ala Ser Asp Ala Asn Leu Thr Ser Thr
     50                  55                  60

Glu Gln His Asn Ile Trp Ala Ser Gln Ala Cys Val Pro Thr Asp Pro
 65                  70                  75                  80

Asn Pro His Glu Phe Pro Leu Gly Asn Val Thr Asp Asn Phe Asp Ile
                 85                  90                  95

Trp Lys Asn Tyr Met Val Asp Gln Met His Glu Asp Ile Ile Ser Leu
            100                 105                 110

Trp Glu Gln Ser Leu Lys Pro Cys Glu Lys Met Thr Phe Leu Cys Val
        115                 120                 125

Gln Met Asn Cys Val Asp Leu Gln Thr Asn Lys Thr Gly Leu Leu Asn
    130                 135                 140

Glu Thr Ile Asn Glu Met Arg Asn Cys Ser Phe Asn Val Thr Thr Val
145                 150                 155                 160

Leu Thr Asp Lys Lys Glu Gln Lys Gln Ala Leu Phe Tyr Val Ser Asp
                165                 170                 175

Leu Ser Lys Val Asn Asp Ser Asn Ala Val Asn Gly Thr Thr Tyr Met
            180                 185                 190

Leu Thr Asn Cys Asn Ser Thr Ile Ile Lys Gln Ala Cys Pro Lys Val
        195                 200                 205

Ser Phe Glu Pro Ile Pro Ile His Tyr Cys Ala Pro Thr Gly Tyr Ala
    210                 215                 220

Ile Phe Lys Cys Asn Asp Thr Asp Phe Asn Gly Thr Gly Leu Cys His
225                 230                 235                 240

Asn Ile Ser Val Val Thr Cys Thr His Gly Ile Lys Pro Thr Val Ser
                245                 250                 255

Thr Gln Leu Ile Leu Asn Gly Thr Leu Ser Arg Glu Lys Ile Arg Ile
            260                 265                 270

Met Gly Lys Asn Ile Thr Glu Ser Ala Lys Asn Ile Ile Val Thr Leu
        275                 280                 285

Asn Thr Pro Ile Asn Met Thr Cys Ile Arg Glu Gly Ile Ala Glu Val
    290                 295                 300

Gln Asp Ile Tyr Thr Gly Pro Met Arg Trp Arg Ser Met Thr Leu Lys
305                 310                 315                 320

Arg Ser Asn Asn Thr Ser Pro Arg Ser Arg Val Ala Tyr Cys Thr Tyr
                325                 330                 335

Asn Lys Thr Val Trp Glu Asn Ala Leu Gln Gln Thr Ala Ile Arg Tyr
            340                 345                 350

Leu Asn Leu Val Asn Gln Thr Glu Asn Val Thr Ile Ile Phe Ser Arg
        355                 360                 365

Thr Ser Gly Gly Asp Ala Glu Val Ser His Leu His Phe Asn Cys His
    370                 375                 380
```

-continued

```
Gly Glu Phe Phe Tyr Cys Asn Thr Ser Gly Met Phe Asn Tyr Thr Phe
385                 390                 395                 400

Ile Asn Cys Thr Lys Ser Gly Cys Gln Glu Ile Lys Gly Ser Asn Glu
            405                 410                 415

Thr Asn Lys Asn Gly Thr Ile Pro Cys Lys Leu Arg Gln Leu Val Arg
            420                 425                 430

Ser Trp Met Lys Gly Glu Ser Arg Ile Tyr Ala Pro Pro Ile Pro Gly
            435                 440                 445

Asn Leu Thr Cys His Ser Asn Ile Thr Gly Met Ile Leu Gln Leu Asp
            450                 455                 460

Gln Pro Trp Asn Ser Thr Gly Glu Asn Thr Leu Arg Pro Val Gly Gly
465                 470                 475                 480

Asp Met Lys Asp Ile Trp Arg Thr Lys Leu Tyr Asn Tyr Lys Val Val
                485                 490                 495

Gln Ile Lys Pro Phe Ser Val Ala Pro Thr Lys Met Ser Arg Pro Ile
                500                 505                 510

Ile Asn Ile His Thr Pro His Arg Glu Lys Arg Ala Val Gly Leu Gly
            515                 520                 525

Met Leu Phe Leu Gly Val Leu Ser Ala Ala Gly Ser Thr Met Gly Ala
            530                 535                 540

Ala Ala Thr Ala Leu Thr Val Arg Thr His Ser Val Leu Lys Gly Ile
545                 550                 555                 560

Val Gln Gln Gln Asp Asn Leu Leu Arg Ala Ile Gln Ala Gln Gln His
                565                 570                 575

Leu Leu Arg Leu Ser Val Trp Gly Ile Arg Gln Leu Arg Ala Arg Leu
                580                 585                 590

Gln Ala Leu Glu Thr Leu Ile Asn Gln Gln Arg Leu Asn Leu Trp Gly
            595                 600                 605

Cys Lys Gly Lys Leu Ile Cys Tyr Thr Ser Val Lys Trp Asn Thr Ser
            610                 615                 620

Trp Ser Gly Arg Tyr Asn Asp Asp Ser Ile Trp Asp Asn Leu Thr Trp
625                 630                 635                 640

Gln Gln Trp Asp Gln His Ile Asn Asn Val Ser Ser Ile Ile Tyr Asp
                645                 650                 655

Glu Ile Gln Ala Ala Gln Asp Gln Gln Glu Lys Asn Val Lys Ala Leu
                660                 665                 670

Leu Glu Leu Asp Glu Trp Ala Ser Leu Trp Asn Trp Phe Asp Ile Thr
            675                 680                 685

Lys Trp Leu Trp Tyr Ile Lys Ile Ala Ile Ile Val Gly Ala Leu
690                 695                 700

Ile Gly Ile Arg Val Ile Met Ile Ile Leu Asn Leu Val Lys Asn Ile
705                 710                 715                 720

Arg Gln Gly Tyr Gln Pro Leu Ser Leu Gln Ile Pro Val Pro His Arg
                725                 730                 735

Gln Glu Ala Glu Thr Pro Gly Arg Thr Gly Glu Glu Gly Gly Glu Gly
            740                 745                 750

Asp Arg Pro Lys Trp Thr Ala Leu Pro Pro Gly Phe Leu Gln Leu
            755                 760                 765

Tyr Thr Asp Leu Arg Thr Ile Ile Leu Trp Thr Tyr His Leu Leu Ser
            770                 775                 780

Asn Leu Ile Ser Gly Ile Arg Arg Leu Ile Asp Tyr Leu Gly Leu Gly
785                 790                 795                 800
```

-continued

```
Leu Trp Ile Leu Gly Gln Lys Thr Ile Glu Ala Cys Arg Leu Cys Gly
                805                 810                 815

Ala Val Met Gln Tyr Trp Leu Gln Glu Leu Lys Asn Ser Ala Thr Asn
            820                 825                 830

Leu Leu Asp Thr Ile Ala Val Ser Val Ala Asn Trp Thr Asp Gly Ile
        835                 840                 845

Ile Leu Gly Leu Gln Arg Ile Gly Gln Gly Phe Leu His Ile Pro Arg
    850                 855                 860

Arg Ile Arg Gln Gly Ala Glu Arg Ile Leu Val
865                 870                 875
```

<210> SEQ ID NO 15
<211> LENGTH: 862
<212> TYPE: PRT
<213> ORGANISM: Simian immunodeficiency virus
<220> FEATURE:
<223> OTHER INFORMATION: Amino acid sequence of homologous region of O_ANT70 lentiviral env protein

<400> SEQUENCE: 15

```
Met Ile Val Thr Met Lys Ala Met Glu Lys Arg Asn Lys Lys Leu Trp
  1               5                  10                  15

Thr Leu Tyr Leu Ala Met Ala Leu Ile Thr Pro Cys Leu Ser Leu Arg
             20                  25                  30

Gln Leu Tyr Ala Thr Val Tyr Ala Gly Val Pro Val Trp Glu Asp Ala
         35                  40                  45

Thr Pro Val Leu Phe Cys Ala Ser Asp Ala Asn Leu Thr Ser Thr Glu
     50                  55                  60

Lys His Asn Ile Trp Ala Ser Gln Ala Cys Val Pro Thr Asp Pro Thr
 65                  70                  75                  80

Pro Tyr Glu Tyr Pro Leu His Asn Val Thr Asp Asp Phe Asn Ile Trp
                 85                  90                  95

Lys Asn Tyr Met Val Glu Gln Met Gln Glu Asp Ile Ile Ser Leu Trp
            100                 105                 110

Asp Gln Ser Leu Lys Pro Cys Val Gln Met Thr Phe Leu Cys Val Gln
        115                 120                 125

Met Glu Cys Thr Asn Ile Ala Gly Thr Thr Asn Glu Asn Leu Met Lys
    130                 135                 140

Lys Cys Glu Phe Asn Val Thr Thr Val Ile Lys Asp Lys Lys Glu Lys
145                 150                 155                 160

Lys Gln Ala Leu Phe Tyr Val Ser Asp Leu Met Glu Leu Asn Glu Thr
                165                 170                 175

Ser Ser Thr Asn Lys Thr Asn Ser Lys Met Tyr Thr Leu Thr Asn Cys
            180                 185                 190

Asn Ser Thr Thr Ile Thr Gln Ala Cys Pro Lys Val Ser Phe Glu Pro
        195                 200                 205

Ile Pro Ile His Tyr Cys Ala Pro Ala Gly Tyr Ala Ile Phe Lys Cys
    210                 215                 220

Asn Ser Thr Glu Phe Asn Gly Thr Gly Thr Cys Arg Asn Ile Thr Val
225                 230                 235                 240

Val Thr Cys Thr His Gly Ile Arg Pro Thr Val Ser Thr Gln Leu Ile
                245                 250                 255

Leu Asn Gly Thr Leu Ser Lys Gly Lys Ile Arg Met Met Ala Lys Asp
            260                 265                 270

Ile Leu Glu Gly Gly Lys Asn Ile Ile Val Thr Leu Asn Ser Thr Leu
        275                 280                 285
```

-continued

```
Asn Met Thr Cys Glu Arg Pro Gln Ile Asp Ile Gln Glu Met Arg Ile
290                 295                 300
Gly Pro Met Ala Trp Tyr Ser Met Gly Ile Gly Thr Ala Gly Asn
305                 310                 315                 320
Ser Ser Arg Ala Ala Tyr Cys Lys Tyr Asn Ala Thr Asp Trp Gly Lys
                325                 330                 335
Ile Leu Lys Gln Thr Ala Glu Arg Tyr Leu Glu Leu Val Asn Asn Thr
                340                 345                 350
Gly Ser Ile Asn Met Thr Phe Asn His Ser Ser Gly Gly Asp Leu Glu
                355                 360                 365
Val Thr His Leu His Phe Asn Cys His Gly Glu Phe Phe Tyr Cys Asn
370                 375                 380
Thr Ala Lys Met Phe Asn Tyr Thr Phe Ser Cys Asn Gly Thr Thr Cys
385                 390                 395                 400
Ser Val Ser Asn Val Ser Gln Gly Asn Asn Gly Thr Leu Pro Cys Lys
                405                 410                 415
Leu Arg Gln Val Val Arg Ser Trp Ile Arg Gly Gln Ser Gly Leu Tyr
                420                 425                 430
Ala Pro Pro Ile Lys Gly Asn Leu Thr Cys Met Ser Asn Ile Thr Gly
                435                 440                 445
Met Ile Leu Gln Met Asp Asn Thr Trp Asn Ser Ser Asn Asn Asn Val
450                 455                 460
Thr Phe Arg Pro Ile Gly Gly Asp Met Lys Asp Ile Trp Arg Thr Glu
465                 470                 475                 480
Leu Phe Asn Tyr Lys Val Val Arg Val Lys Pro Phe Ser Val Ala Pro
                485                 490                 495
Thr Arg Ile Ala Arg Pro Val Ile Ser Thr Arg Thr His Arg Glu Lys
                500                 505                 510
Arg Ala Val Gly Leu Gly Met Leu Phe Leu Gly Val Leu Ser Ala Ala
                515                 520                 525
Gly Ser Thr Met Gly Ala Ala Ala Thr Thr Leu Ala Val Gln Thr His
530                 535                 540
Thr Leu Leu Lys Gly Ile Val Gln Gln Gln Asp Asn Leu Leu Arg Ala
545                 550                 555                 560
Ile Gln Ala Gln Gln Gln Leu Leu Arg Leu Ser Trp Gly Ile Arg Gln
                565                 570                 575
Leu Arg Ala Arg Leu Leu Ala Leu Glu Thr Leu Leu Gln Asn Gln Gln
                580                 585                 590
Leu Leu Ser Leu Trp Gly Cys Lys Gly Lys Leu Val Cys Tyr Thr Ser
                595                 600                 605
Val Lys Trp Asn Arg Thr Trp Ile Gly Asn Glu Ser Ile Trp Asp Thr
610                 615                 620
Leu Thr Trp Gln Glu Trp Asp Arg Gln Ile Ser Asn Ile Ser Ser Thr
625                 630                 635                 640
Ile Tyr Glu Glu Ile Gln Lys Ala Gln Val Gln Gln Glu Gln Asn Glu
                645                 650                 655
Lys Lys Leu Leu Glu Leu Asp Glu Trp Ala Ser Ile Trp Asn Trp Leu
                660                 665                 670
Asp Ile Thr Lys Trp Leu Trp Tyr Ile Lys Ile Ala Ile Ile Ile Val
                675                 680                 685
Gly Ala Leu Val Gly Val Arg Val Ile Met Ile Val Leu Asn Ile Val
                690                 695                 700
```

-continued

Lys Asn Ile Arg Gln Gly Tyr Gln Pro Leu Ser Leu Gln Ile Pro Asn
705 710 715 720

His His Gln Glu Glu Ala Gly Thr Pro Gly Arg Thr Gly Gly Gly Gly
725 730 735

Gly Glu Glu Gly Arg Pro Arg Trp Ile Pro Ser Pro Gln Gly Phe Leu
740 745 750

Pro Leu Leu Tyr Thr Asp Leu Arg Thr Ile Ile Leu Trp Thr Tyr His
755 760 765

Leu Leu Ser Asn Leu Ala Ser Gly Ile Gln Lys Val Ile Ser Tyr Leu
770 775 780

Arg Leu Gly Leu Trp Ile Leu Gly Gln Lys Ile Ile Asn Val Cys Arg
785 790 795 800

Ile Cys Ala Ala Val Thr Gln Tyr Trp Leu Gln Glu Leu Gln Asn Ser
805 810 815

Ala Thr Ser Leu Leu Asp Thr Leu Ala Val Ala Val Ala Asn Trp Thr
820 825 830

Asp Gly Ile Ile Ala Gly Ile Gln Arg Ile Gly Thr Gly Ile Arg Asn
835 840 845

Ile Pro Arg Arg Ile Arg Gln Gly Leu Glu Arg Ser Leu Leu
850 855 860

<210> SEQ ID NO 16
<211> LENGTH: 854
<212> TYPE: PRT
<213> ORGANISM: Simian immunodeficiency virus
<220> FEATURE:
<223> OTHER INFORMATION: Amino acid sequence of homologous region of
SIVcpzGAB1 lentiviral env protein

<400> SEQUENCE: 16

Met Lys Val Met Glu Lys Lys Lys Arg Asp Trp Asn Ser Leu Ser Ile
1 5 10 15

Ile Thr Ile Ile Thr Ile Ile Leu Leu Thr Pro Cys Leu Thr Ser Glu
20 25 30

Leu Trp Val Thr Val Tyr Tyr Gly Val Pro Val Trp His Asp Ala Asp
35 40 45

Pro Val Leu Phe Cys Ala Ser Asp Ala Lys Ala His Ser Thr Glu Ala
50 55 60

His Asn Ile Trp Ala Thr Gln Ala Cys Val Pro Thr Asp Pro Ser Pro
65 70 75 80

Gln Glu Val Phe Leu Pro Asn Val Ile Glu Ser Phe Asn Met Trp Lys
85 90 95

Asn Asn Met Val Asp Gln Met His Glu Asp Ile Ile Ser Leu Trp Asp
100 105 110

Gln Ser Leu Lys Pro Cys Val Lys Leu Thr Pro Leu Cys Val Thr Leu
115 120 125

Gln Cys Ser Lys Ala Asn Phe Ser Gln Ala Lys Asn Leu Thr Asn Gln
130 135 140

Thr Ser Ser Pro Pro Leu Glu Met Lys Asn Cys Ser Phe Asn Val Thr
145 150 155 160

Thr Glu Leu Arg Asp Lys Lys Lys Gln Val Tyr Ser Leu Phe Tyr Val
165 170 175

Glu Asp Val Val Asn Leu Gly Asn Glu Asn Asn Thr Tyr Arg Ile Ile
180 185 190

Asn Cys Asn Thr Thr Ala Ile Thr Gln Ala Cys Pro Lys Thr Ser Phe
195 200 205

```
Glu Pro Ile Pro Ile His Tyr Cys Ala Pro Ala Gly Phe Ala Ile Leu
210                 215                 220

Lys Cys Asn Asp Lys Asp Phe Ser Gly Lys Gly Lys Cys Thr Asn Val
225                 230                 235                 240

Ser Thr Val His Cys Thr His Gly Ile Lys Pro Val Val Thr Thr Gln
                245                 250                 255

Leu Leu Ile Asn Gly Ser Leu Ala Glu Gly Asn Ile Thr Val Arg Val
            260                 265                 270

Glu Asn Lys Ser Lys Asn Thr Asp Val Trp Ile Val Gln Leu Val Glu
        275                 280                 285

Ala Val Ser Leu Asn Cys His Arg Pro Gly Asn Asn Thr Arg Gly Glu
290                 295                 300

Val Gln Ile Gly Pro Gly Met Thr Phe Tyr Asn Ile Glu Asn Val Val
305                 310                 315                 320

Gly Asp Thr Arg Ser Ala Tyr Cys Lys Ile Asn Gly Thr Trp Asn
                325                 330                 335

Arg Thr Val Glu Glu Val Lys Lys Ala Leu Ala Thr Ser Ser Asn Arg
            340                 345                 350

Thr Ala Ala Asn Ile Thr Leu Asn Arg Ala Ser Gly Gly Asp Pro Glu
            355                 360                 365

Val Thr His His Met Phe Asn Cys Gly Gly Glu Phe Phe Tyr Cys Asn
370                 375                 380

Thr Ser Gln Ile Phe Thr Asp Asn Ile Thr Asn Gly Ile Ile Ile Leu
385                 390                 395                 400

Pro Cys Arg Ile Arg Gln Ile Val Ser Ser Trp Met Arg Val Gly Arg
                405                 410                 415

Gly Ile Tyr Ala Pro Pro Ile Arg Gly Asn Ile Thr Cys Asn Ser Asn
            420                 425                 430

Ile Thr Gly Leu Leu Leu Thr Ser Asp Thr Pro Val Thr Asn Asn Ser
            435                 440                 445

Gly Asn Leu Thr Phe Arg Pro Thr Gly Gly Asn Met Lys Asp Ile Trp
450                 455                 460

Arg Ser Glu Leu Tyr Lys Tyr Lys Val Val Arg Ile Glu Pro Leu Ser
465                 470                 475                 480

Val Ala Pro Thr Lys Ala Arg Arg His Thr Val Ala Arg Gln Lys Asp
                485                 490                 495

Arg Gln Lys Arg Ala Ala Phe Gly Leu Gly Ala Leu Phe Leu Gly Phe
            500                 505                 510

Leu Gly Ala Ala Gly Ser Thr Met Gly Ala Ala Ala Val Thr Leu Thr
            515                 520                 525

Val Gln Ala Arg Gln Leu Leu Ser Gly Ile Val Gln Gln Gln Asn Asn
530                 535                 540

Leu Leu Lys Ala Ile Glu Ala Gln Gln His Leu Leu Gln Leu Ser Ile
545                 550                 555                 560

Trp Gly Val Lys Gln Leu Gln Ala Arg Leu Leu Ala Val Glu Arg Tyr
                565                 570                 575

Leu Gln Asp Gln Gln Ile Leu Gly Leu Trp Gly Cys Ser Gly Lys Ala
            580                 585                 590

Val Cys Tyr Thr Thr Val Pro Trp Asn Asn Ser Trp Pro Gly Ser Asn
            595                 600                 605

Ser Thr Asp Asp Ile Trp Gly Asn Leu Thr Trp Gln Gln Trp Asp Lys
610                 615                 620
```

Leu Val Ser Asn Tyr Thr Gly Lys Ile Phe Gly Leu Glu Glu Ala
625                 630                 635                 640

Gln Ser Gln Gln Glu Lys Asn Glu Arg Asp Leu Leu Glu Leu Asp Gln
                645                 650                 655

Trp Ala Ser Leu Trp Asn Trp Phe Asp Ile Thr Lys Trp Leu Trp Tyr
                660                 665                 670

Ile Lys Ile Phe Leu Met Ala Val Gly Ile Ile Gly Leu Arg Ile
                675                 680                 685

Ile Met Thr Val Phe Ser Val Val Arg Val Arg Gln Gly Tyr Ser
690                 695                 700

Pro Leu Ser Leu Gln Thr Leu Ile Pro Val Gln Arg Glu Gln Gly Arg
705                 710                 715                 720

Leu Gly Glu Ile Asp Glu Gly Gly Gly Glu Gln Asp Arg Ser Arg Ser
                725                 730                 735

Val Arg Leu Val Glu Gly Cys Leu Pro Leu Ile Trp Asp Asp Leu Arg
                740                 745                 750

Asn Leu Gly Ile Trp Ser Tyr Gln Ser Leu Thr Ser Leu Ala Cys Asn
                755                 760                 765

Val Trp Arg Gln Leu Lys Thr Leu Gly His Leu Ile Leu His Ser Leu
770                 775                 780

Arg Leu Leu Arg Glu Arg Leu Cys Leu Leu Gly Gly Ile Ile Gln Tyr
785                 790                 795                 800

Trp Gly Lys Glu Leu Lys Ile Ser Ala Ile Ser Leu Leu Asp Ala Thr
                805                 810                 815

Ala Ile Ala Val Ala Glu Gly Thr Asp Arg Ile Ile Glu Ala Phe Gln
                820                 825                 830

Val Thr Leu Arg Ile Ile Arg Asn Ile Pro Arg Arg Ile Arg Gln Gly
                835                 840                 845

Leu Glu Arg Ala Leu Leu
    850

<210> SEQ ID NO 17
<211> LENGTH: 854
<212> TYPE: PRT
<213> ORGANISM: Simian immunodeficiency virus
<220> FEATURE:
<223> OTHER INFORMATION: Amino acid sequence of homologous region of
      SIVcpzANT lentiviral env protein

<400> SEQUENCE: 17

Met Arg Lys Pro Ile His Ile Ile Trp Gly Leu Ala Leu Leu Ile Gln
1               5                   10                  15

Phe Ile Glu Lys Gly Thr Asn Glu Asp Tyr Val Thr Val Phe Tyr Gly
                20                  25                  30

Val Pro Val Trp Arg Asn Ala Thr Pro Thr Leu Phe Cys Ala Thr Asn
                35                  40                  45

Ala Ser Met Thr Ser Thr Glu Val His Asn Val Trp Ala Thr Thr Ser
        50                  55                  60

Cys Val Pro Ile Asp Pro Asp Pro Ile Val Arg Leu Asn Thr Ser
65                  70                  75                  80

Val Trp Phe Asn Ala Tyr Lys Asn Tyr Met Val Glu Ser Met Thr Glu
                85                  90                  95

Asp Met Gln Leu Phe Gln Gln Ser His Lys Pro Cys Val Lys Leu Thr
                100                 105                 110

Pro Met Cys Ile Lys Met Asn Cys Thr Gly Tyr Asn Gly Thr Pro Thr
                115                 120                 125

-continued

```
Thr Pro Ser Thr Thr Thr Ser Thr Val Thr Pro Lys Thr Thr Thr Pro
    130                 135                 140
Ile Val Asp Gly Met Lys Leu Gln Glu Cys Asn Phe Asn Gln Ser Thr
145                 150                 155                 160
Gly Phe Lys Asp Lys Lys Gln Lys Met Lys Ala Ile Phe Tyr Lys Gly
                165                 170                 175
Asp Leu Met Lys Cys Gln Asp Asn Asn Glu Thr Asn Cys Tyr Tyr Leu
            180                 185                 190
Trp His Cys Asn Thr Thr Thr Ile Thr Gln Ser Cys Glu Lys Ser Thr
        195                 200                 205
Phe Glu Pro Ile Pro Ile His Tyr Cys Ala Pro Ala Gly Tyr Ala Ile
    210                 215                 220
Leu Arg Cys Glu Asp Glu Asp Phe Thr Gly Val Gly Met Cys Lys Asn
225                 230                 235                 240
Val Ser Val Val His Cys Thr His Gly Ile Ser Pro Met Val Ala Thr
                245                 250                 255
Trp Leu Leu Leu Asn Gly Thr Tyr Gln Thr Asn Thr Ser Val Val Met
                260                 265                 270
Asn Gly Arg Lys Asn Glu Ser Val Leu Val Arg Phe Gly Lys Glu Phe
            275                 280                 285
Glu Asn Leu Thr Ile Thr Cys Ile Arg Pro Gly Asn Arg Thr Val Arg
        290                 295                 300
Asn Leu Gln Ile Gly Pro Gly Met Thr Phe Tyr Asn Val Glu Ile Ala
305                 310                 315                 320
Thr Gly Asp Thr Arg Lys Ala Phe Cys Thr Val Asn Lys Thr Leu Trp
                325                 330                 335
Glu Gln Ala Arg Asn Lys Thr Glu His Val Leu Ala Glu His Trp Lys
            340                 345                 350
Lys Val Asp Asn Lys Thr Asn Ala Lys Thr Ile Trp Thr Phe Gln Asp
        355                 360                 365
Gly Asp Pro Glu Val Lys Val His Trp Phe Asn Cys Gln Gly Glu Phe
    370                 375                 380
Phe Tyr Cys Asp Ile Thr Pro Trp Phe Asn Ala Thr Tyr Thr Gly Asn
385                 390                 395                 400
Leu Ile Thr Asn Gly Ala Leu Ile Ala His Cys Arg Ile Lys Gln Ile
                405                 410                 415
Val Asn His Trp Gly Ile Val Ser Lys Gly Ile Tyr Leu Ala Pro Arg
            420                 425                 430
Arg Gly Asn Val Ser Cys Thr Ser Ser Ile Thr Gly Ile Met Leu Glu
        435                 440                 445
Gly Gln Ile Tyr Asn Glu Thr Val Lys Val Ser Pro Ala Ala Arg Val
    450                 455                 460
Ala Asp Gln Trp Arg Ala Glu Leu Ser Arg Tyr Gln Val Val Glu Ile
465                 470                 475                 480
Pro Leu Ser Val Ala Pro Thr Thr Lys Arg Pro Glu Ile Lys Gln His
                485                 490                 495
Ser Arg Gln Lys Arg Gly Ile Gly Ile Gly Leu Phe Phe Leu Gly Leu
            500                 505                 510
Leu Ser Ala Ala Gly Ser Thr Met Gly Ala Ala Ser Ile Ala Leu Thr
        515                 520                 525
Ala Gln Thr Arg Asn Leu His Gly Ile Val Gln Gln Gln Ala Asn Leu
    530                 535                 540
```

-continued

```
Leu Gln Ala Ile Glu Thr Gln Gln His Leu Leu Gln Leu Ser Val Trp
545                 550                 555                 560

Gly Val Lys Gln Leu Gln Ala Arg Met Leu Ala Val Glu Lys Tyr Leu
                565                 570                 575

Arg Asp Gln Gln Leu Leu Ser Leu Trp Gly Cys Ala Asp Lys Val Thr
            580                 585                 590

Cys His Thr Thr Val Pro Trp Asn Asn Ser Trp Val Asn Phe Thr Gln
        595                 600                 605

Thr Cys Ala Lys Asn Ser Ser Asp Ile Gln Cys Ile Trp Glu Asn Met
    610                 615                 620

Thr Trp Gln Glu Trp Asp Arg Leu Val Gln Asn Ser Thr Gly Gln Ile
625                 630                 635                 640

Tyr Asn Ile Leu Gln Ile Ala His Glu Gln Gln Glu Arg Asn Lys Lys
                645                 650                 655

Glu Leu Tyr Glu Leu Asp Lys Trp Ser Ser Leu Trp Asn Trp Phe Asp
            660                 665                 670

Ile Thr Gln Trp Leu Trp Tyr Ile Lys Ile Phe Ile Met Ile Val Gly
        675                 680                 685

Ala Ile Val Gly Leu Arg Ile Leu Leu Val Leu Val Ser Cys Leu Arg
    690                 695                 700

Lys Val Arg Gln Gly Tyr His Pro Leu Ser Phe Gln Ile Pro Thr Gln
705                 710                 715                 720

Asn Gln Gln Asp Pro Glu Gln Pro Glu Glu Ile Arg Glu Glu Gly Gly
                725                 730                 735

Arg Lys Asp Arg Ile Arg Trp Arg Ala Leu Gln His Gly Phe Phe Ala
            740                 745                 750

Leu Leu Trp Val Asp Leu Thr Ser Ile Ile Gln Trp Ile Tyr Gln Ile
        755                 760                 765

Cys Arg Thr Cys Leu Leu Asn Leu Trp Ala Val Leu Gln His Leu Cys
    770                 775                 780

Arg Ile Thr Phe Arg Leu Cys Asn His Leu Glu Asn Asn Leu Ser Thr
785                 790                 795                 800

Leu Trp Thr Ile Ile Arg Thr Glu Ile Lys Asn Ile Asp Arg Leu
                805                 810                 815

Ala Ile Trp Val Gly Glu Lys Thr Asp Ser Ile Leu Leu Ala Leu Gln
            820                 825                 830

Thr Ile Val Arg Ile Ile Arg Glu Val Pro Arg Arg Ile Arg Gln Gly
        835                 840                 845

Leu Glu Ile Ala Leu Asn
    850

<210> SEQ ID NO 18
<211> LENGTH: 858
<212> TYPE: PRT
<213> ORGANISM: Simian immunodeficiency virus
<220> FEATURE:
<223> OTHER INFORMATION: Amino acid sequence of homologous region of
      A_ROD lentiviral env protein

<400> SEQUENCE: 18

Met Met Asn Gln Leu Leu Ile Ala Ile Leu Leu Ala Ser Ala Cys Leu
  1               5                  10                  15

Val Tyr Cys Thr Gln Tyr Val Thr Val Phe Tyr Gly Val Pro Thr Trp
                 20                  25                  30

Lys Asn Ala Thr Ile Pro Leu Phe Cys Ala Thr Arg Asn Arg Asp Thr
             35                  40                  45
```

```
Trp Gly Thr Ile Gln Cys Leu Pro Asp Asn Asp Tyr Gln Glu Ile
 50                  55                  60
Thr Leu Asn Val Thr Glu Ala Phe Asp Ala Trp Asn Asn Thr Val Thr
 65                  70                  75                  80
Glu Gln Ala Ile Glu Asp Val Trp His Leu Phe Glu Thr Ser Ile Lys
                 85                  90                  95
Pro Cys Val Lys Leu Thr Pro Leu Cys Val Ala Met Lys Cys Ser Ser
                100                 105                 110
Thr Glu Ser Ser Thr Gly Asn Asn Thr Thr Ser Lys Ser Thr Ser Thr
                115                 120                 125
Thr Thr Thr Thr Pro Thr Asp Gln Glu Gln Glu Ile Ser Glu Asp Thr
            130                 135                 140
Pro Cys Ala Arg Ala Asp Asn Cys Ser Gly Leu Gly Glu Glu Glu Thr
145                 150                 155                 160
Ile Asn Cys Gln Phe Asn Met Thr Gly Leu Glu Arg Asp Lys Lys Lys
                165                 170                 175
Gln Tyr Asn Glu Thr Trp Tyr Ser Lys Asp Val Val Cys Glu Thr Asn
                180                 185                 190
Asn Ser Thr Asn Gln Thr Gln Cys Tyr Met Asn His Cys Asn Thr Ser
                195                 200                 205
Val Ile Thr Glu Ser Cys Asp Lys His Tyr Trp Asp Ala Ile Arg Phe
            210                 215                 220
Arg Tyr Cys Ala Pro Pro Gly Tyr Ala Leu Leu Arg Cys Asn Asp Thr
225                 230                 235                 240
Asn Tyr Ser Gly Phe Ala Pro Asn Cys Ser Lys Val Val Ala Ser Thr
                245                 250                 255
Cys Thr Arg Met Met Glu Thr Gln Thr Ser Thr Trp Phe Gly Phe Asn
                260                 265                 270
Gly Thr Arg Ala Glu Asn Arg Thr Tyr Ile Tyr Trp His Gly Arg Asp
            275                 280                 285
Asn Arg Thr Ile Ile Ser Leu Asn Lys Tyr Tyr Asn Leu Ser Leu His
            290                 295                 300
Cys Lys Arg Pro Gly Asn Lys Ile Val Lys Gln Ile Met Leu Met Ser
305                 310                 315                 320
Gly His Val Phe His Ser His Tyr Gln Pro Ile Asn Lys Arg Pro Arg
                325                 330                 335
Gln Ala Trp Cys Trp Phe Lys Gly Lys Trp Lys Asp Ala Met Gln Glu
                340                 345                 350
Val Lys Glu Thr Leu Ala Lys His Pro Arg Tyr Arg Gly Thr Asn Asp
            355                 360                 365
Thr Arg Asn Ile Ser Phe Ala Ala Pro Gly Lys Gly Ser Asp Pro Glu
            370                 375                 380
Val Ala Tyr Met Trp Thr Asn Cys Arg Gly Glu Phe Leu Tyr Cys Asn
385                 390                 395                 400
Met Thr Trp Phe Leu Asn Trp Ile Glu Asn Lys Thr His Arg Asn Tyr
                405                 410                 415
Ala Pro Cys His Ile Lys Gln Ile Ile Asn Thr Trp His Lys Val Gly
            420                 425                 430
Arg Asn Val Tyr Leu Pro Pro Arg Glu Gly Glu Leu Ser Cys Asn Ser
            435                 440                 445
Thr Val Thr Ser Ile Ile Ala Asn Ile Asp Trp Gln Asn Asn Asn Gln
450                 455                 460
```

```
Thr Asn Ile Thr Phe Ser Ala Glu Val Ala Glu Leu Tyr Arg Leu Glu
465                 470                 475                 480

Leu Gly Asp Tyr Lys Leu Val Glu Ile Thr Pro Ile Gly Phe Ala Pro
                485                 490                 495

Thr Lys Glu Lys Arg Tyr Ser Ser Ala His Gly Arg His Thr Arg Gly
            500                 505                 510

Val Phe Val Leu Gly Phe Leu Gly Phe Leu Ala Thr Ala Gly Ser Ala
        515                 520                 525

Met Gly Ala Ala Ser Leu Thr Val Ser Ala Gln Ser Arg Thr Leu Leu
    530                 535                 540

Ala Gly Ile Val Gln Gln Gln Gln Leu Leu Asp Val Val Lys Arg
545                 550                 555                 560

Gln Gln Glu Leu Leu Arg Leu Thr Val Trp Gly Thr Lys Asn Leu Gln
                565                 570                 575

Ala Arg Val Thr Ala Ile Glu Lys Tyr Leu Gln Asp Gln Ala Arg Leu
            580                 585                 590

Asn Ser Trp Gly Cys Ala Phe Arg Gln Val Cys His Thr Thr Val Pro
        595                 600                 605

Trp Val Asn Asp Ser Leu Ala Pro Asp Trp Asp Asn Met Thr Trp Gln
    610                 615                 620

Glu Trp Glu Lys Gln Val Arg Tyr Leu Glu Ala Asn Ile Ser Lys Ser
625                 630                 635                 640

Leu Glu Gln Ala Gln Ile Gln Gln Glu Lys Asn Met Tyr Glu Leu Gln
                645                 650                 655

Lys Leu Asn Ser Trp Asp Ile Phe Gly Asn Trp Phe Asp Leu Thr Ser
            660                 665                 670

Trp Val Lys Tyr Ile Gln Tyr Gly Val Leu Ile Ile Val Ala Val Ile
        675                 680                 685

Ala Leu Arg Ile Ile Tyr Val Val Gln Met Leu Ser Arg Leu Arg
690                 695                 700

Lys Gly Tyr Arg Pro Val Phe Ser Ser Pro Gly Tyr Ile Gln Gln
705                 710                 715                 720

Ile His Ile His Lys Asp Arg Gly Gln Pro Ala Asn Glu Glu Thr Glu
                725                 730                 735

Glu Asp Gly Gly Ser Asn Gly Gly Asp Arg Tyr Trp Pro Trp Pro Ile
            740                 745                 750

Ala Tyr Ile His Phe Leu Ile Arg Gln Leu Ile Arg Leu Leu Thr Arg
        755                 760                 765

Leu Tyr Ser Ile Cys Arg Asp Leu Leu Ser Arg Ser Phe Leu Thr Leu
770                 775                 780

Gln Leu Ile Tyr Gln Asn Leu Arg Asp Trp Leu Arg Leu Arg Thr Ala
785                 790                 795                 800

Phe Leu Gln Tyr Gly Cys Glu Trp Ile Gln Glu Ala Phe Gln Ala Ala
                805                 810                 815

Ala Arg Ala Thr Arg Glu Thr Leu Ala Gly Ala Cys Arg Gly Leu Trp
            820                 825                 830

Arg Val Leu Glu Arg Ile Gly Arg Gly Ile Leu Ala Val Pro Arg Arg
        835                 840                 845

Ile Arg Gln Gly Ala Glu Ile Ala Leu Leu
        850                 855

<210> SEQ ID NO 19
<211> LENGTH: 852
<212> TYPE: PRT
```

-continued

```
<213> ORGANISM: Simian immunodeficiency virus
<220> FEATURE:
<223> OTHER INFORMATION: Amino acid sequence of homologous region of
      B_EHO lentiviral env protein

<400> SEQUENCE: 19

Met Ala His Val Asn Asn Tyr Leu Leu Val Thr Leu Leu Leu Ile Ser
  1               5                  10                  15

Ile Tyr Gly Tyr Met Gly Lys Asn Phe Val Thr Val Phe Tyr Gly Ile
             20                  25                  30

Pro Ala Trp Lys Asn Ala Ser Ile Pro Leu Phe Cys Ala Thr Arg Asn
         35                  40                  45

Arg Asp Thr Trp Gly Thr Val Gln Cys Leu Pro Asp Asn Asp Asp Tyr
     50                  55                  60

Thr Glu Ile Gln Leu Asn Ile Thr Glu Ala Phe Asp Ala Trp Asp Asn
 65                  70                  75                  80

Thr Val Thr Asp Gln Ala Thr Lys Asp Val Trp Ser Leu Phe Glu Thr
                 85                  90                  95

Ser Ile Lys Pro Cys Val Lys Leu Thr Pro Leu Cys Val Thr Met Lys
            100                 105                 110

Cys Asn Lys Thr Trp Ser Ser Ala Ser Lys Glu Thr Thr Thr Ser Ser
        115                 120                 125

Ala Ser Leu Arg Ser Ser Thr Gln Thr Leu Leu Asn Glu Asp Ser Lys
    130                 135                 140

Cys Ile Gln Asn Asp Ser Cys Ala Gly Ile Gly Leu Glu Glu Met Ile
145                 150                 155                 160

Asp Cys Gln Phe Lys Met Thr Gly Leu Lys Arg Asp Glu Ser Lys Gln
                165                 170                 175

Tyr Lys Asp Thr Trp Tyr Lys Gln Asp Leu Val Cys Glu Lys Gly Thr
            180                 185                 190

Arg Ser Asn Glu Ser Lys Cys Tyr Ile Lys Thr Cys Asn Thr Ser Ile
        195                 200                 205

Ile Gln Glu Ser Cys Asp Lys His Tyr Trp Asp Ser Leu Arg Phe Arg
    210                 215                 220

Tyr Cys Ala Pro Pro Gly Phe Ala Leu Leu Arg Cys Asn Asp Thr Lys
225                 230                 235                 240

Tyr Ser Gly Phe Met Pro Asn Cys Ser Lys Val Val Val Ser Leu Tyr
                245                 250                 255

Arg Met Met Glu Thr Gln Thr Ser Thr Trp Phe Gly Phe Asn Gly Thr
            260                 265                 270

Arg Ala Glu Asn Arg Thr Tyr Ile Tyr Trp His Gly Lys Asp Asn Arg
        275                 280                 285

Thr Ile Ile Ser Leu Asn Ser Tyr Tyr Asn Leu Thr Met His Cys Lys
    290                 295                 300

Arg Pro Gly Asn Lys Met Val Val Pro Ile Arg Thr Val Ser Gly Ile
305                 310                 315                 320

Leu Phe His Ser Gln Pro Ile Asn Lys Arg Pro Lys Gln Ala Trp Cys
                325                 330                 335

Trp Phe Lys Gly Asn Trp Thr Glu Ala Ile Gln Glu Val Lys Glu Thr
            340                 345                 350

Ile Lys Asn His Pro Arg Tyr Ser Gly Thr Thr Asn Ile Ser Gln Ile
        355                 360                 365

Arg Leu Ala Glu His Ala Arg Ser Ser Asp Pro Glu Val Arg Tyr Met
    370                 375                 380
```

-continued

```
Trp Thr Asn Cys Arg Gly Glu Phe Leu Tyr Cys Asn Met Thr Phe Phe
385                 390                 395                 400

Leu Asn Trp Val Glu Asn Arg Thr Gly Leu Lys Arg Asn Tyr Ala Ser
            405                 410                 415

Cys His Ile Arg Gln Ile Val Asn Thr Trp His Lys Ile Gly Arg Asn
            420                 425                 430

Val Tyr Leu Pro Pro Arg Glu Gly Leu Ser Cys Asn Ser Thr Val
        435                 440                 445

Thr Ser Leu Ile Ala Asn Ile Asp Trp Ile Asp Lys Asn Leu Thr Asn
450                 455                 460

Ile Thr Val Ser Ala Glu Val Ser Glu Leu Tyr Lys Leu Glu Leu Gly
465                 470                 475                 480

Asp Tyr Lys Leu Val Glu Ile Thr Pro Ile Gly Phe Ala Pro Thr Ser
                485                 490                 495

Ile Lys Arg Tyr Ser Ser Val Thr Pro Arg Asn Lys Arg Gly Val Leu
            500                 505                 510

Val Leu Gly Phe Leu Gly Phe Leu Ala Thr Ala Gly Ser Ala Met Gly
            515                 520                 525

Ala Ala Ser Leu Thr Leu Ser Ala Gln Ser Arg Thr Leu Leu Ala Gly
            530                 535                 540

Ile Val Gln Gln Gln Gln Leu Val Asp Val Val Lys Arg Gln Gln
545                 550                 555                 560

Glu Leu Leu Arg Leu Thr Val Trp Gly Thr Lys Asn Leu Gln Ala Arg
            565                 570                 575

Val Thr Ala Ile Glu Lys Tyr Leu Lys Asp Gln Ala Gln Leu Asn Ser
            580                 585                 590

Trp Gly Cys Ala Phe Arg Gln Val Cys His Thr Thr Val Pro Trp Val
        595                 600                 605

Asn Glu Ser Leu Lys Pro Asp Trp Asn Met Thr Trp Gln Gln Trp
        610                 615                 620

Glu Arg Gln Val Arg Phe Leu Asp Ala Asn Ile Thr Lys Leu Leu Glu
625                 630                 635                 640

Glu Ala Gln Ile Gln Gln Glu Lys Asn Met Tyr Glu Leu Gln Lys Leu
                645                 650                 655

Asn Gln Trp Asp Ile Phe Ser Asn Trp Phe Asp Phe Thr Ser Trp Met
            660                 665                 670

Ala Tyr Ile Arg Leu Gly Leu Tyr Ile Val Ile Gly Ile Val Val Leu
        675                 680                 685

Arg Ile Ala Ile Tyr Ile Ile Gln Met Leu Ala Arg Leu Arg Lys Gly
        690                 695                 700

Tyr Arg Pro Val Phe Ser Ser Pro Ser Tyr Thr Gln Ile Pro
705                 710                 715                 720

Ile Arg Lys Asp Arg Gly Gln Pro Ala Asn Glu Glu Thr Glu Glu Gly
            725                 730                 735

Gly Gly Asn Asn Glu Gly Tyr Arg Ser Trp Pro Trp Gln Ile Glu Tyr
                740                 745                 750

Ile His Phe Pro Ile Arg Gln Leu Arg Asp Leu Leu Ile Trp Leu Tyr
        755                 760                 765

Ser Gly Cys Arg Thr Leu Leu Ser Lys Thr Phe Gln Thr Leu Gln Pro
        770                 775                 780

Val Leu Gln Pro Leu Arg Leu Pro Pro Ala Tyr Leu Arg Tyr Gly Ile
785                 790                 795                 800

Ser Trp Phe Gln Glu Ala Ile Gln Ala Ala Ala Arg Ala Ala Gly Glu
```

-continued

```
                805                 810                 815
Thr Leu Ala Ser Ala Ala Arg Thr Ser Trp Gly Val Leu Arg Arg Ala
                820                 825                 830
Ala Gly Glu Ile Ile Ala Ile Pro Arg Ile Arg Gln Gly Ala Glu
            835                 840                 845
Leu Ala Leu Leu
        850

<210> SEQ ID NO 20
<211> LENGTH: 877
<212> TYPE: PRT
<213> ORGANISM: Simian immunodeficiency virus
<220> FEATURE:
<223> OTHER INFORMATION: Amino acid sequence of homologous region of
      SIVAGMVER3 lentiviral env protein

<400> SEQUENCE: 20

Met Lys Leu Thr Leu Leu Ile Gly Ile Leu Leu Ile Gly Ile Gly Val
  1               5                  10                  15

Val Leu Asn Thr Arg Gln Gln Trp Val Thr Val Phe Tyr Gly Val Pro
                 20                  25                  30

Val Trp Lys Asn Ser Ser Val Gln Ala Phe Cys Met Thr Pro Thr Thr
             35                  40                  45

Arg Leu Trp Ala Thr Thr Asn Ser Ile Pro Asp Asp His Asp Tyr Thr
         50                  55                  60

Glu Val Pro Leu Asn Ile Thr Glu Pro Phe Glu Ala Trp Ala Asp Arg
 65                  70                  75                  80

Asn Pro Leu Val Ala Gln Ala Gly Ser Asn Ile His Leu Leu Phe Glu
                 85                  90                  95

Gln Thr Leu Lys Pro Cys Val Lys Leu Ser Pro Leu Cys Ile Lys Met
                100                 105                 110

Ser Cys Val Glu Leu Asn Ser Ser Glu Pro Thr Thr Thr Pro Lys Ser
            115                 120                 125

Thr Thr Ala Ser Thr Thr Asn Ile Thr Ala Ser Thr Thr Thr Leu Pro
        130                 135                 140

Cys Val Gln Asn Lys Thr Ser Thr Val Leu Glu Ser Cys Asn Glu Thr
145                 150                 155                 160

Ile Ile Glu Lys Glu Leu Asn Glu Glu Pro Ala Ser Asn Cys Thr Phe
                165                 170                 175

Ala Met Ala Gly Tyr Val Arg Asp Gln Lys Lys Tyr Ser Val Val
            180                 185                 190

Trp Asn Asp Ala Glu Ile Met Cys Lys Lys Gly Asn Asn Ser Asn Arg
        195                 200                 205

Glu Cys Tyr Met Ile His Cys Asn Asp Ser Val Ile Lys Glu Ala Cys
    210                 215                 220

Asp Lys Thr Tyr Trp Asp Glu Leu Arg Leu Arg Tyr Cys Ala Pro Ala
225                 230                 235                 240

Gly Phe Ala Leu Leu Lys Cys Asn Asp Tyr Asp Tyr Ala Gly Phe Lys
                245                 250                 255

Thr Asn Cys Ser Asn Val Ser Val Val His Cys Thr Asn Leu Ile Asn
            260                 265                 270

Thr Thr Val Thr Thr Gly Leu Leu Leu Asn Gly Ser Tyr Ser Glu Asn
        275                 280                 285

Arg Thr Gln Ile Trp Gln Lys His Arg Val Ser Asn Asp Ser Val Leu
    290                 295                 300
```

-continued

```
Val Leu Phe Asn Lys His Tyr Asn Leu Thr Val Thr Cys Lys Arg Pro
305                 310                 315                 320

Gly Asn Lys Thr Val Leu Pro Val Thr Ile Met Ala Gly Leu Val Phe
                325                 330                 335

His Ser Gln Arg Tyr Asn Thr Arg Leu Arg Gln Ala Trp Cys His Phe
                340                 345                 350

Gln Gly Asn Trp Arg Gly Ala Trp Lys Glu Val Lys Asn Glu Ile Val
                355                 360                 365

Lys Leu Pro Lys Asp Arg Tyr Gln Gly Thr Asn Asp Thr Glu Ile
370                 375                 380

Tyr Leu Gln Arg Leu Phe Gly Asp Pro Glu Ala Ala Asn Leu Trp Phe
385                 390                 395                 400

Asn Cys Gln Gly Glu Phe Phe Tyr Cys Lys Met Asp Trp Phe Leu Asn
                405                 410                 415

Tyr Leu Asn Asn Arg Thr Val Asp Pro Asp His Asn Pro Cys Asn Gly
                420                 425                 430

Thr Lys Gly Lys Gly Lys Ala Pro Gly Pro Cys Ala Gln Arg Thr Tyr
                435                 440                 445

Val Ala Cys His Ile Arg Ser Val Ile Asn Asp Trp Tyr Thr Leu Ser
                450                 455                 460

Arg Lys Thr Tyr Ala Pro Pro Arg Glu Gly His Leu Gln Cys Thr Ser
465                 470                 475                 480

Thr Val Thr Gly Met Ser Val Glu Leu Asn Tyr Asn Ser Lys Asn Arg
                485                 490                 495

Thr Asn Val Thr Leu Ser Pro Gln Ile Glu Thr Ile Trp Ala Ala Glu
                500                 505                 510

Leu Gly Arg Tyr Lys Leu Val Glu Ile Thr Pro Ile Gly Phe Ala Pro
                515                 520                 525

Thr Glu Val Arg Arg Tyr Thr Gly Gly His Asp Arg Thr Lys Arg Val
                530                 535                 540

Pro Phe Val Leu Gly Phe Leu Gly Phe Leu Gly Ala Ala Gly Thr Ala
545                 550                 555                 560

Met Gly Ala Ala Ala Thr Ala Leu Thr Val Gln Ser Gln His Leu Leu
                565                 570                 575

Ala Gly Ile Leu Gln Gln Lys Asn Leu Leu Ala Ala Val Glu Ala
                580                 585                 590

Gln Gln Gln Met Leu Lys Leu Thr Ile Trp Gly Val Lys Asn Leu Asn
                595                 600                 605

Ala Arg Val Thr Ala Leu Glu Lys Tyr Leu Glu Asp Gln Ala Arg Leu
610                 615                 620

Asn Ala Trp Gly Cys Ala Trp Lys Gln Val Cys His Thr Thr Val Pro
625                 630                 635                 640

Trp Gln Trp Asn Asn Arg Thr Pro Asp Trp Asn Asn Met Thr Trp Leu
                645                 650                 655

Glu Trp Glu Arg Gln Ile Ser Tyr Leu Glu Gly Asn Ile Thr Thr Gln
                660                 665                 670

Leu Glu Glu Ala Arg Ala Gln Glu Glu Lys Asn Leu Asp Ala Tyr Gln
                675                 680                 685

Lys Leu Ser Ser Trp Ser Asp Phe Trp Ser Trp Phe Asp Phe Ser Lys
                690                 695                 700

Trp Leu Asn Ile Leu Lys Ile Gly Phe Leu Asp Val Leu Gly Ile Ile
705                 710                 715                 720

Gly Leu Arg Leu Leu Tyr Thr Val Tyr Ser Cys Ile Ala Arg Val Arg
```

-continued

```
                725                 730                 735

Gln Gly Tyr Ser Pro Leu Ser Pro Gln Ile His Ile His Pro Trp Lys
            740                 745                 750

Gly Gln Pro Asp Asn Ala Glu Gly Pro Gly Glu Gly Gly Asp Lys Arg
        755                 760                 765

Lys Asn Ser Ser Glu Pro Trp Gln Lys Glu Ser Gly Thr Ala Glu Trp
    770                 775                 780

Lys Ser Asn Trp Cys Lys Arg Leu Thr Asn Trp Cys Ser Ile Ser Ser
785                 790                 795                 800

Ile Trp Leu Tyr Asn Ser Cys Leu Thr Leu Leu Val His Leu Arg Ser
                805                 810                 815

Ala Phe Gln Tyr Ile Gln Tyr Gly Leu Gly Glu Leu Lys Ala Ala Ala
            820                 825                 830

Gln Glu Ala Val Val Ala Leu Ala Arg Leu Ala Gln Asn Ala Gly Tyr
        835                 840                 845

Gln Ile Trp Leu Ala Cys Arg Ser Ala Tyr Arg Ala Ile Ile Asn Ser
    850                 855                 860

Pro Arg Arg Val Arg Gln Gly Leu Glu Gly Ile Leu Asn
865                 870                 875

<210> SEQ ID NO 21
<211> LENGTH: 832
<212> TYPE: PRT
<213> ORGANISM: Simian immunodeficiency virus
<220> FEATURE:
<223> OTHER INFORMATION: Amino acid sequence of homologous region of
      SIVSYK173 lentiviral env protein

<400> SEQUENCE: 21

Met Ala Ala Phe Arg Thr Tyr Ile Val Cys Leu Phe Ser Leu Ile Ser
  1               5                  10                  15

Leu Gly Phe Met Glu Lys Gln Gln Tyr Val Thr Val Phe Tyr Gly Ile
             20                  25                  30

Pro His Trp Glu Asp Ala Tyr Ala Pro Leu Phe Cys Thr Thr Ser His
         35                  40                  45

Lys Gly Gly Trp Ala Thr Lys Asn Cys Val Pro Ser Ala Asp Gln Ile
     50                  55                  60

Glu Val Arg Val Asn Ile Thr Gly Glu Tyr Phe Pro Ala Trp Asn Ser
 65                  70                  75                  80

Ser His Met Ile Arg Gln Gln Ile Leu Glu Asp Met Ser Ala Leu Phe
                 85                  90                  95

Leu Gln Ala Asn Arg Pro Cys Val Lys Leu Ala Pro Met Cys Ile Arg
            100                 105                 110

Met Leu Cys Thr Leu Asp Asn Ser Pro Ala Thr Ser Thr Pro Thr Thr
        115                 120                 125

Ser Pro Pro Thr Thr Pro Pro Asn Glu Thr Trp Trp Gly Asp Asn Ser
    130                 135                 140

Thr Glu Pro Arg Phe Asn Cys Ser Phe Asn Leu Thr Gly Gly Phe Lys
145                 150                 155                 160

Asp Lys Lys Gln Gln Tyr Arg Ala Phe Phe Tyr Lys Asp Asp Leu Met
                165                 170                 175

Lys Glu Glu Gly Asn Ser Ser Tyr Tyr Tyr Leu Leu His Cys Asn Thr
            180                 185                 190

Ser Val Ile Ser Ala Ala Cys Glu Lys Gln Thr Phe Gln Pro Phe Pro
        195                 200                 205
```

```
-continued

Ile Gln Tyr Cys Ala Pro Pro Gly Tyr Ser Leu Leu Lys Cys Asn Asp
    210                 215                 220

Thr Asn Phe Glu Gly Asp Asp Val Cys Thr Asn Val Thr Ala Val Ser
225                 230                 235                 240

Cys Thr Gln Glu Phe Asn Thr Leu Ala Ser Thr Trp Phe Gln Leu Asn
                245                 250                 255

Gly Thr Tyr Lys Ala Lys Asp Lys Val Arg Phe Ile Lys Gln Lys Asp
                260                 265                 270

Lys Asn Glu Ser Val Ile Ile Leu Val Pro Glu Ala Leu Arg Leu Gln
            275                 280                 285

Ile Ile Cys Glu Arg Pro Gly Asn Glu Ser Ile Lys Asn Ile Gln Leu
        290                 295                 300

Ala Ala Gly Tyr Phe Leu Pro Val Ile Gln Lys Leu Lys Thr Gly
305                 310                 315                 320

Arg Asp Ala Lys Arg Ala Phe Cys Arg Val Thr Gly Asn Trp Thr Glu
                325                 330                 335

Phe Phe Lys Gln Val His Glu Gln Ala Thr Lys Thr Trp Lys Asn Val
            340                 345                 350

Thr Asn Thr Thr Trp Arg Ser Gln Pro Gly Gly Asp Leu Glu Val Arg
        355                 360                 365

Thr His Trp Phe Gln Cys Gly Gly Glu Phe Phe Tyr Cys Asn Val Ser
    370                 375                 380

Lys Leu Phe Ala Asn Ile Thr Asn Gly Asn Ala Ser Lys Asn Asn Tyr
385                 390                 395                 400

Ala Ser Asn Leu Arg Leu Ser Cys Ala Ile Arg Gln Ile Ile Asn Asp
                405                 410                 415

Trp Arg Tyr Val Arg Lys Leu Ile Tyr Leu Pro Pro Thr Ala Gly His
            420                 425                 430

Ile Lys Cys Thr Ser Asn Val Thr Ala Val Leu Thr Asp Ile Glu Tyr
        435                 440                 445

Tyr Pro Gly Ser Thr Leu Asn Phe Thr Pro Thr Ala Asn Val Glu Asp
    450                 455                 460

Val Trp Arg Ala Asp Leu Phe Asn Tyr Lys Leu Ile Gln Ile Lys Pro
465                 470                 475                 480

Ile Gly Phe Ala Pro Thr Asp Gln Arg Arg Tyr Glu Leu Pro Asn Thr
                485                 490                 495

Arg Glu Lys Arg Ala Ala Pro Leu Ala Leu Gly Phe Leu Gly Leu Leu
            500                 505                 510

Ser Ala Ala Gly Thr Ala Met Gly Gly Ala Ala Thr Ala Leu Thr Leu
        515                 520                 525

Gln Ser Gln Thr Leu Leu Ala Gly Ile Val Gln Gln Gln Gln Lys Leu
    530                 535                 540

Leu Glu Ala Val Glu Ala Gln Gln His Leu Leu Gly Leu Thr Val Trp
545                 550                 555                 560

Gly Val Lys Asn Leu Asn Ala Arg Leu Thr Ala Leu Glu Thr Tyr Leu
                565                 570                 575

Arg Asp Gln Ala Ile Leu Ser Asn Trp Gly Cys Ala Phe Lys Gln Ile
            580                 585                 590

Cys His Thr Ala Val Thr Trp Glu Lys Ala Cys Gly Asn Asn Ser Asn
        595                 600                 605

Phe Cys Pro Lys Pro Gln Trp Lys Asn Met Thr Trp His Arg Trp Glu
    610                 615                 620

Gln Glu Val Asp Asn Leu Thr Asp His Ile Asp Gly Leu Leu Arg Glu
```

```
625                 630                 635                 640

Ala Gln Glu Gln Gln Glu Arg Asn Val His Asp Leu Thr Lys Leu Gln
                645                 650                 655

Glu Trp Asp Ser Leu Trp Ser Trp Phe Asp Leu Ser Lys Trp Phe Phe
                660                 665                 670

Tyr Leu Lys Ile Gly Phe Tyr Val Ile Gly Ala Leu Val Leu Leu Arg
                675                 680                 685

Leu Val Ser Phe Ser Val Gly Ile Ile Lys Asn Leu Leu Gly Gly Tyr
            690                 695                 700

Val Pro Ile Leu Gln Asn Pro Thr Gln Gly Arg Lys Asp Pro Gly Lys
705                 710                 715                 720

Pro Ala Asp Glu Glu Glu Gly Ser Gly Asp Arg Glu Gly Leu Asn Val
                725                 730                 735

Ser Thr Phe Ser Arg Glu Ser Leu Arg Gln Ser Leu Glu Ala Gly Gln
                740                 745                 750

Gln Leu Trp Arg Thr Val Cys Ser Ser Phe Arg Ser Leu Ile Arg Gln
                755                 760                 765

Leu Thr Ile Thr Trp Gly Phe Ile Ser Tyr Gly Phe Asn Glu Leu Lys
                770                 775                 780

Ile Ala Ala Ala Ser Leu Gly Arg Glu Ile Arg Asp Trp Val Ala Ala
785                 790                 795                 800

Ile Trp Gln Ala Ile Tyr Ala Ala Thr Arg Arg Val Val Glu Ala Val
                805                 810                 815

Ala Ala Leu Pro Arg Arg Leu Arg Gln Gly Leu Glu Ile Tyr Leu Asn
                820                 825                 830

<210> SEQ ID NO 22
<211> LENGTH: 71
<212> TYPE: PRT
<213> ORGANISM: Simian immunodeficiency virus
<220> FEATURE:
<223> OTHER INFORMATION: Putative amino acid sequence of homologous
      region of extended rev ORF in SIVsmPbj1.9

<400> SEQUENCE: 22

Met Ser Ser Asn Glu Glu Glu Leu Arg Arg Arg Leu Arg Leu Ile His
  1               5                  10                  15

Leu Leu His Gln Thr Ser Lys Tyr Gly Met Ser Trp Glu Ser Ala Ala
             20                  25                  30

Tyr Arg Ala Leu Ala Ile Lys Cys Phe Arg Asp Leu Leu Cys Ser Ile
         35                  40                  45

Cys Asn Ser Ile Leu Trp Tyr Thr Ser Met Glu Glu Cys Asp Ser Ser
     50                  55                  60

Pro Leu Leu Cys Asn Gln Gly
 65                  70

<210> SEQ ID NO 23
<211> LENGTH: 75
<212> TYPE: PRT
<213> ORGANISM: Simian immunodeficiency virus
<220> FEATURE:
<223> OTHER INFORMATION: Putative amino acid sequence of homologous
      region of extended rev ORF in SIVrcmGB-1

<400> SEQUENCE: 23

Met Leu Pro Gly Gln Asp Glu Glu Asp Leu Arg Lys Lys Ile Arg Leu
  1               5                  10                  15

Ile Asn Phe Leu Tyr Leu Ile Ser Lys Tyr Gly Val Pro Trp Thr Ser
```

```
                    20                  25                  30

Thr Ala Phe Arg Ala Ser Ala Lys Lys Val Phe Ile Asp Leu Leu Val
                35                  40                  45

Thr Ile Ile Lys Gly Lys Tyr Asn Ser Leu Leu Trp Cys Pro Ser Met
            50                  55                  60

Glu Lys Gln His Ser Ala Tyr Val Leu Cys Asp
 65                  70                  75

<210> SEQ ID NO 24
<211> LENGTH: 71
<212> TYPE: PRT
<213> ORGANISM: Simian immunodeficiency virus
<220> FEATURE:
<223> OTHER INFORMATION: Amino acid sequence of homologous region
      of extended rev ORF in SIVsmPbj

<400> SEQUENCE: 24

Met Ser Ser Asn Glu Glu Glu Leu Arg Arg Arg Leu Arg Leu Ile His
 1               5                  10                  15

Leu Leu His Gln Thr Ser Lys Tyr Gly Met Ser Trp Glu Ser Ala Ala
                20                  25                  30

Tyr Arg Ala Leu Ala Ile Lys Cys Phe Arg Asp Leu Leu Cys Ser Ile
            35                  40                  45

Cys Asn Ser Ile Leu Trp Tyr Thr Ser Met Glu Glu Cys Asp Ser Ser
        50                  55                  60

Pro Leu Leu Cys Asn Gln Glu
 65                  70

<210> SEQ ID NO 25
<211> LENGTH: 71
<212> TYPE: PRT
<213> ORGANISM: Simian immunodeficiency virus
<220> FEATURE:
<223> OTHER INFORMATION: Amino acid sequence of homologous region
      of extended rev ORF in SIVsmM9

<400> SEQUENCE: 25

Met Ser Ser Asn Glu Glu Glu Leu Arg Arg Arg Leu Arg Leu Ile His
 1               5                  10                  15

Phe Leu His Gln Thr Ser Lys Tyr Gly Met Ser Trp Glu Ser Ala Ala
                20                  25                  30

Tyr Arg Ala Leu Ala Ile Lys Cys Phe Arg Asp Leu Leu Cys Ser Ile
            35                  40                  45

Cys Asn Ser Ile Leu Trp Cys Thr Ser Met Glu Glu Cys Asp Ser Ser
        50                  55                  60

Pro Leu Leu Cys Asn Gln Lys
 65                  70

<210> SEQ ID NO 26
<211> LENGTH: 71
<212> TYPE: PRT
<213> ORGANISM: Simian immunodeficiency virus
<220> FEATURE:
<223> OTHER INFORMATION: Amino acid sequence of homologous region
      of extended rev ORF in SIVsmH4

<400> SEQUENCE: 26

Met Ser Ser Thr Glu Glu Glu Leu Arg Arg Arg Leu Arg Leu Ile His
 1               5                  10                  15

Phe Leu His Gln Thr Ser Lys Tyr Gly Met Ser Trp Glu Ser Ala Ala
                20                  25                  30
```

```
Tyr Arg Ala Leu Ala Ser Lys Cys Phe Arg Asp Leu Cys Ser Ile
        35                  40                  45

Cys Asn Ser Ile Leu Trp Cys Thr Ser Met Glu Glu Cys Asp Asn Ser
    50                  55                  60

Pro Leu Leu Cys Asn Gln Glu
65              70

<210> SEQ ID NO 27
<211> LENGTH: 73
<212> TYPE: PRT
<213> ORGANISM: Simian immunodeficiency virus
<220> FEATURE:
<223> OTHER INFORMATION: Amino acid sequence of homologous region
      of extended rev ORF in SIVmac142

<400> SEQUENCE: 27

Met Arg Ser His Thr Gly Glu Glu Leu Arg Arg Arg Leu Arg Leu
1               5                   10                  15

Ile His Leu Leu His Gln Thr Ser Lys Tyr Gly Leu Ser Trp Lys Ser
                20                  25                  30

Ala Ala Tyr Arg His Leu Ala Ser Lys Cys Leu Trp Asp Leu Leu Tyr
        35                  40                  45

Ser Ile Cys His Ser Leu Leu Trp Cys Thr Ser Leu Glu Glu Cys Asp
    50                  55                  60

Asn Ser Pro Leu Leu Cys Asn Gln Glu
65                  70

<210> SEQ ID NO 28
<211> LENGTH: 73
<212> TYPE: PRT
<213> ORGANISM: Simian immunodeficiency virus
<220> FEATURE:
<223> OTHER INFORMATION: Amino acid sequence of homologous region
      of extended rev ORF in SIVmac251

<400> SEQUENCE: 28

Met Ser Ser His Glu Arg Glu Glu Leu Arg Lys Arg Leu Arg Leu
1               5                   10                  15

Ile His Leu Leu His Gln Thr Ser Lys Tyr Gly Met Ser Trp Glu Ser
                20                  25                  30

Ala Ala Tyr Arg His Leu Ala Phe Lys Cys Leu Trp Asp Leu Leu Tyr
        35                  40                  45

Ser Ile Cys His Ser Leu Leu Trp Cys Thr Ser Leu Glu Glu Cys Asp
    50                  55                  60

Asn Ser Pro Leu Leu Cys Asn Gln Glu
65                  70

<210> SEQ ID NO 29
<211> LENGTH: 73
<212> TYPE: PRT
<213> ORGANISM: Simian immunodeficiency virus
<220> FEATURE:
<223> OTHER INFORMATION: Amino acid sequence of homologous region
      of extended rev ORF in SIVmac239

<400> SEQUENCE: 29

Met Ser Asn His Glu Arg Glu Glu Leu Arg Lys Arg Leu Arg Leu
1               5                   10                  15

Ile His Leu Leu His Gln Thr Ser Lys Tyr Gly Met Ser Trp Glu Ser
                20                  25                  30
```

```
Ala Ala Tyr Arg His Leu Ala Phe Lys Cys Leu Trp Asp Leu Leu Tyr
        35                  40                  45

Ser Ile Cys His Ser Leu Leu Trp Cys Thr Ser Leu Glu Glu Cys Asp
    50                  55                  60

Asn Ser Pro Leu Leu Cys Asn Gln Glu
65                  70

<210> SEQ ID NO 30
<211> LENGTH: 73
<212> TYPE: PRT
<213> ORGANISM: Simian immunodeficiency virus
<220> FEATURE:
<223> OTHER INFORMATION: Amino acid sequence of homologous region
      of extended rev ORF in SIVmac1all

<400> SEQUENCE: 30

Met Ser Ser His Glu Arg Glu Glu Leu Arg Lys Arg Leu Arg Leu
1               5                   10                  15

Ile His Leu Leu His Gln Thr Ser Lys Tyr Gly Met Ser Trp Glu Ser
            20                  25                  30

Ala Ala Tyr Arg His Leu Ala Phe Lys Cys Leu Trp Asp Leu Leu Tyr
        35                  40                  45

Ser Ile Cys His Ser Leu Leu Trp Cys Thr Ser Leu Glu Glu Cys Asp
    50                  55                  60

Asp Ser Pro Leu Leu Cys Asn Gln Glu
65                  70

<210> SEQ ID NO 31
<211> LENGTH: 73
<212> TYPE: PRT
<213> ORGANISM: Simian immunodeficiency virus
<220> FEATURE:
<223> OTHER INFORMATION: Amino acid sequence of homologous region
      of extended rev ORF in SIVmac132zm

<400> SEQUENCE: 31

Met Ser Asn His Glu Arg Glu Glu Leu Arg Lys Arg Leu Arg Leu
1               5                   10                  15

Ile His Leu Leu His Gln Thr Ser Lys Tyr Gly Met Ser Trp Glu Ser
            20                  25                  30

Ala Ala Tyr Arg His Leu Ala Phe Lys Cys Leu Trp Asp Leu Leu Tyr
        35                  40                  45

Pro Ile Cys His Ser Leu Leu Trp Cys Thr Ser Leu Glu Glu Cys Asp
        50                  55                  60

Asn Ser Pro Leu Leu Cys Asn Gln Glu
65                  70

<210> SEQ ID NO 32
<211> LENGTH: 71
<212> TYPE: PRT
<213> ORGANISM: Simian immunodeficiency virus
<220> FEATURE:
<223> OTHER INFORMATION: Amino acid sequence of homologous region
      of extended rev ORF in SIVmacSTM

<400> SEQUENCE: 32

Met Ser Asp Gln Glu Glu Glu Leu Arg Lys Arg Leu Arg Leu Ile Gln
1               5                   10                  15

Phe Leu His Gln Thr Ser Lys Tyr Gly Leu Pro Trp Lys Ser Thr Ala
            20                  25                  30

Tyr Arg Tyr Leu Ala Ile Lys Cys Leu Leu Asp Leu Leu His Ser Val
```

-continued

```
                35                  40                  45
Cys His Gly Ile Leu Trp Cys Thr Ser Met Glu Glu Cys Asp Asp Ser
        50                  55                  60
Pro Leu Leu Cys Asn Gln Glu
65                  70

<210> SEQ ID NO 33
<211> LENGTH: 73
<212> TYPE: PRT
<213> ORGANISM: Human immunodeficiency virus
<220> FEATURE:
<223> OTHER INFORMATION: Amino acid sequence of homologous region
      of extended rev ORF in HIV2/FO784

<400> SEQUENCE: 33

Met Ser Gln Ala Glu Lys Glu Glu Leu Arg Arg Leu Arg Leu
  1               5                  10                  15

Ile Tyr Leu Leu His Gln Thr Ser Lys His Gly Val Ser Trp Glu Ser
                20                  25                  30

Ala Thr Tyr Arg Asn Leu Ala Ile Lys Tyr Phe Phe Asp Ile Leu Cys
            35                  40                  45

Ser Val Cys His Ser Ile Leu Trp Tyr Thr Arg Met Glu Lys Cys Asp
        50                  55                  60

Asn Thr Pro Leu Leu Arg Asn Gln Lys
65                  70

<210> SEQ ID NO 34
<211> LENGTH: 73
<212> TYPE: PRT
<213> ORGANISM: Human immunodeficiency virus
<220> FEATURE:
<222> LOCATION: 30, 47, 72
<223> OTHER INFORMATION: Amino acid sequence of homologous region
      of extended rev ORF in HIV2/BEN; Xaa = other =
      inactivating mutations

<400> SEQUENCE: 34

Met Ser Glu Arg Ala Asp Glu Glu Gly Leu Gln Gly Lys Leu Arg Leu
  1               5                  10                  15

Leu Arg Leu Leu His Gln Thr Ser Glu Tyr Gly Ala Trp Xaa Glu Ser
                20                  25                  30

Ala Val Cys Cys His Phe Thr Asn Lys Cys Leu Leu Ser Ile Leu Xaa
            35                  40                  45

Pro Val Cys Asp Cys Phe Leu Trp His Thr Arg Val Glu Lys Cys Ile
        50                  55                  60

Tyr Ser Leu Ile Leu Cys Asn Xaa Lys
65                  70

<210> SEQ ID NO 35
<211> LENGTH: 74
<212> TYPE: PRT
<213> ORGANISM: Human immunodeficiency virus
<220> FEATURE:
<222> LOCATION: 41, 73
<223> OTHER INFORMATION: Amino acid sequence of homologous region
      of extended rev ORF in HIV2/CAM2; Xaa = other =
      inactivating mutations

<400> SEQUENCE: 35

Met Thr Glu Arg Ala Asp Glu Glu Gly Leu Gln Arg Lys Leu Arg Leu
  1               5                  10                  15

Ile Arg Leu Leu His Gln Thr Ser Glu Tyr Gly Ala Trp Gln Lys Ser
```

```
                        20                  25                  30
Ala Ala Tyr Cys His Ser Thr Ser Xaa Cys Leu Leu Asn Ile Leu Gln
            35                  40                  45

Thr Thr Ile Cys Asp Cys Phe Leu Trp Arg Thr Arg Val Glu Lys Cys
    50                  55                  60

Ile His Ser Pro Leu Leu Cys Asn Xaa Lys
65                  70
```

<210> SEQ ID NO 36
<211> LENGTH: 72
<212> TYPE: PRT
<213> ORGANISM: Human immunodeficiency virus
<220> FEATURE:
<222> LOCATION: 28, 29
<223> OTHER INFORMATION: Amino acid sequence of homologous region
      of extended rev ORF in HIV2/EHO; Xaa = other =
      inactivating mutations

<400> SEQUENCE: 36

```
Met Asn Ala Arg Glu Arg Asp Leu Gln Lys Gly Leu Arg Leu Leu His
 1               5                  10                  15

Leu Leu His Gln Thr Ser Glu Tyr Gly Thr Cys Xaa Xaa Leu Pro Thr
            20                  25                  30

Cys Tyr Thr Pro Ala Tyr Lys Tyr Leu Trp Val Tyr Gly Gln Glu Leu
        35                  40                  45

Cys His Cys Leu Leu Trp Tyr Thr Arg Met Glu Lys Cys Ile Asn Ser
    50                  55                  60

Pro Leu Leu Cys Tyr Gln Lys Gln
65                  70
```

<210> SEQ ID NO 37
<211> LENGTH: 74
<212> TYPE: PRT
<213> ORGANISM: Human immunodeficiency virus
<220> FEATURE:
<222> LOCATION: 26, 30, 41, 72
<223> OTHER INFORMATION: Amino acid sequence of homologous region
      of extended rev ORF in HIV2/GH1; Xaa = other =
      inactivating mutations

<400> SEQUENCE: 37

```
Met His Glu Lys Ala Asp Gly Glu Glu Leu Gln Glu Arg Leu Arg Leu
 1               5                  10                  15

Ile Arg Leu Leu His Gln Thr Ser Glu Xaa Asp Val Trp Xaa Glu Ser
            20                  25                  30

Thr Met Cys Cys Gln Leu Ala Ser Xaa Cys Leu Leu Ser Ile Leu His
        35                  40                  45

Pro Ile Cys Asp Cys Phe Leu Trp Arg Ala Arg Val Glu Lys Cys Ile
    50                  55                  60

His Ser Pro Leu Leu Cys Asn Xaa Lys Gln
65                  70
```

<210> SEQ ID NO 38
<211> LENGTH: 73
<212> TYPE: PRT
<213> ORGANISM: Human immunodeficiency virus
<220> FEATURE:
<222> LOCATION: 29, 30, 41
<223> OTHER INFORMATION: Amino acid sequence of homologous region
      of extended rev ORF in HIV2/KR; Xaa = other =
      inactivating mutations

<400> SEQUENCE: 38

Met Asn Gly Arg Ala Asp Glu Glu Gly Leu Gln Arg Lys Gln Arg Leu
1               5                   10                  15

Ile Arg Leu Leu His Gln Thr Ser Glu Tyr Asn Gly Xaa Xaa Lys Ser
                20                  25                  30

Ala Asn Cys Cys His Phe Thr Asn Xaa Cys Leu Leu Asn Ile Leu Arg
            35                  40                  45

Pro Ile Cys Asp Cys Phe Leu Trp His Thr Arg Val Glu Glu Cys Ile
        50                  55                  60

His Ser Pro Leu Leu Cys Asn Gln Lys
65                  70

<210> SEQ ID NO 39
<211> LENGTH: 75
<212> TYPE: PRT
<213> ORGANISM: Human immunodeficiency virus
<220> FEATURE:
<222> LOCATION: 41
<223> OTHER INFORMATION: Amino acid sequence of homologous region
      of extended rev ORF in HIV2/MDS; Xaa = other =
      inactivating mutation

<400> SEQUENCE: 39

Met Asn Glu Arg Ala Asp Glu Glu Gly Leu Gln Arg Lys Leu Arg Leu
1               5                   10                  15

Ile Arg Leu Leu His Gln Thr Ser Glu Tyr Asp Ala Gln Asn Ala Ser
                20                  25                  30

Ala Ala Tyr Cys His Phe Thr Asn Xaa Cys Leu Leu Asn Ile Leu Gln
            35                  40                  45

Thr Thr Thr Ile Cys Asn Cys Phe Leu Trp His Thr Arg Val Glu Glu
        50                  55                  60

Cys Ile His Ser Pro Leu Leu Cys Asn Gln Lys
65                  70                  75

<210> SEQ ID NO 40
<211> LENGTH: 73
<212> TYPE: PRT
<213> ORGANISM: Human immunodeficiency virus
<220> FEATURE:
<222> LOCATION: 29, 30, 41
<223> OTHER INFORMATION: Amino acid sequence of homologous region
      of extended rev ORF in HIV2/NIHZ; Xaa = other =
      inactivating mutations

<400> SEQUENCE: 40

Met Thr Glu Arg Ala Asp Glu Glu Gly Leu Gln Arg Lys Leu Arg Leu
1               5                   10                  15

Ile Arg Leu Leu His Gln Thr Ser Glu Tyr Glu Gly Xaa Xaa Glu Ser
                20                  25                  30

Thr Ala Asp Cys Tyr Cys Thr Ser Xaa Cys Leu Pro Asn Thr Leu Gln
            35                  40                  45

Ala Ile Cys Asp Cys Phe Leu Arg His Thr Arg Val Glu Glu Cys Ile
        50                  55                  60

His Ser Pro Val Leu Cys Asn Gln Lys
65                  70

<210> SEQ ID NO 41
<211> LENGTH: 69
<212> TYPE: PRT
<213> ORGANISM: Human immunodeficiency virus
<220> FEATURE:
<222> LOCATION: 38

-continued

<223> OTHER INFORMATION: Amino acid sequence of homologous region
of extended rev ORF in HIV2/ROD; Xaa = other =
inactivating mutations

<400> SEQUENCE: 41

Met Asn Glu Arg Ala Asp Glu Glu Gly Leu Gln Arg Lys Leu Arg Leu
1               5                   10                  15

Ile Arg Leu Leu His Gln Thr Ser Glu Tyr Asp Glu Ser Ala Ala Tyr
            20                  25                  30

Cys His Phe Ile Ser Xaa Cys Leu Leu Ser Ile Leu His Pro Ile Cys
        35                  40                  45

Asn Cys Phe Leu Trp Thr His Val Glu Lys Cys Asn His Ser Pro Leu
    50                  55                  60

Leu Cys Asn Gln Lys
65

<210> SEQ ID NO 42
<211> LENGTH: 73
<212> TYPE: PRT
<213> ORGANISM: Human immunodeficiency virus
<220> FEATURE:
<222> LOCATION: 30, 41, 72
<223> OTHER INFORMATION: Amino acid sequence of homologous region
of extended rev ORF in HIV2/SBLISY; Xaa = other =
inactivating mutations

<400> SEQUENCE: 42

Met Thr Glu Arg Ala Asp Glu Glu Gly Val Arg Arg Lys Leu Arg Leu
1               5                   10                  15

Ile Arg Leu Leu His Gln Thr Ser Glu Tyr Asn Glu Trp Xaa Asn Ser
            20                  25                  30

Ala Ala Cys Cys Leu Ser Ala Asn Xaa Cys Leu Leu Asn Ile Leu His
        35                  40                  45

Gln Ile Cys Asp Cys Phe Leu Trp Ser Thr Arg Val Glu Lys Cys Ile
    50                  55                  60

His Ser Pro Leu Leu Cys Asn Xaa Lys
65                  70

<210> SEQ ID NO 43
<211> LENGTH: 73
<212> TYPE: PRT
<213> ORGANISM: Human immunodeficiency virus
<220> FEATURE:
<222> LOCATION: 26, 30, 41, 72
<223> OTHER INFORMATION: Amino acid sequence of homologous region
of extended rev ORF in HIV2/ST; Xaa = other =
inactivating mutations

<400> SEQUENCE: 43

Met Asn Glu Arg Ala Glu Glu Glu Leu Arg Arg Lys Leu Arg Leu
1               5                   10                  15

Ile Arg Leu Leu His Gln Thr Ser Glu Xaa Asp Val Trp Xaa Glu Ser
            20                  25                  30

Thr Ile Cys Cys Gln Leu Ala Ser Xaa Cys Leu Leu Asn Ile Leu Arg
        35                  40                  45

Pro Ile Cys Asp Cys Phe Leu Trp Arg Ala Arg Val Glu Lys Cys Ile
    50                  55                  60

His Ser Pro Leu Leu Cys Asn Xaa Lys
65                  70

<210> SEQ ID NO 44

```
<211> LENGTH: 74
<212> TYPE: PRT
<213> ORGANISM: Human immunodeficiency virus
<220> FEATURE:
<222> LOCATION: 28, 47
<223> OTHER INFORMATION: Amino acid sequence of homologous region
      of extended rev ORF in HIV2/UC1; Xaa = other =
      inactivating mutations

<400> SEQUENCE: 44

Met Thr Thr Arg Glu Lys Asp Leu Gln Lys Gly Leu Arg Leu Leu His
 1               5                  10                  15

Leu Leu His Gln Thr Ser Glu Tyr Gly Thr His Xaa Gln Ser Pro Val
            20                  25                  30

Tyr Phe Ala Pro Thr Tyr Lys Cys Leu Trp Val Ser Gly Ser Xaa Glu
        35                  40                  45

Lys Leu Cys His Cys Leu Leu Trp His Thr Cys Met Glu Glu Arg Asn
 50                  55                  60

Gly Ser Ser Leu Leu Cys Asn His Lys Gln
 65                  70

<210> SEQ ID NO 45
<211> LENGTH: 518
<212> TYPE: PRT
<213> ORGANISM: Simian immunodeficiency virus
<220> FEATURE:
<223> OTHER INFORMATION: Deduced amino acid sequence of SIVrcm Gag
      protein

<400> SEQUENCE: 45

Met Gly Ala Arg Ala Ser Leu Leu Ser Gly Lys Lys Leu Asp Ala Trp
 1               5                  10                  15

Glu Ser Val Arg Leu Arg Pro Gly Gly Lys Lys Lys Tyr Met Leu Lys
            20                  25                  30

His Leu Val Trp Ala Cys Lys Lys Leu Asn Lys Phe Gly Leu Ser Asp
        35                  40                  45

His Leu Leu Glu Thr Ala Thr Gly Cys Glu Lys Ile Leu Gly Val Leu
 50                  55                  60

Leu Pro Leu Val Pro Thr Gly Ser Glu Gly Leu Lys Ser Leu Phe Asn
 65                  70                  75                  80

Leu Cys Cys Val Leu Trp Cys Val His Lys Glu Val Lys Val Lys Asp
                85                  90                  95

Thr Glu Glu Ala Val Ala Lys Val Lys Glu Cys Cys His Leu Val Glu
            100                 105                 110

Lys Ala Glu Asn Thr Thr Glu Lys Glu Lys Gly Ala Thr Ala Pro Pro
        115                 120                 125

Ser Gly Gln Arg Gly Asn Tyr Pro Ile Ile Thr Ile Asn Gln Gln Pro
 130                 135                 140

Glu His Asn Pro Ile Ser Pro Arg Thr Leu Asn Ala Trp Val Lys Val
145                 150                 155                 160

Val Glu Glu Lys Lys Phe Ser Ala Glu Val Ala Pro Met Phe Ser Ala
                165                 170                 175

Leu Ser Glu Gly Cys Ile Pro Tyr Asp Ile Asn Gln Met Leu Asn Ala
            180                 185                 190

Ile Gly Glu His Gln Gly Ala Leu Gln Ile Val Lys Glu Val Ile Asn
        195                 200                 205

Glu Glu Ala Ala Asp Trp Asp Ala Arg His Pro Val Pro Gly Pro Ile
 210                 215                 220
```

```
Pro Ala Gly Gln Leu Arg Glu Pro Thr Gly Ser Asp Ile Ala Gly Thr
225                 230                 235                 240

Thr Ser Ser Ile Ala Glu Gln Ile Ala Trp Thr Thr Arg Ala Asn Asn
            245                 250                 255

Pro Ile Asn Val Gly Asn Leu Tyr Arg Asn Trp Ile Ile Val Gly Leu
        260                 265                 270

Gln Lys Trp Val Lys Met Tyr Asn Pro Val Asn Ile Leu Asp Ile Lys
    275                 280                 285

Gln Gly Pro Lys Glu Ser Phe Lys Asp Tyr Val Asp Arg Phe Tyr Lys
290                 295                 300

Ala Leu Arg Ala Glu Gln Ala Asp Pro Ala Val Lys Asn Trp Met Thr
305                 310                 315                 320

Gln Ser Leu Leu Ile Gln Asn Ala Asn Pro Asp Cys Lys Met Val Leu
            325                 330                 335

Lys Gly Leu Gly Met Asn Pro Ser Leu Glu Glu Met Leu Thr Ala Cys
        340                 345                 350

Gln Gly Val Gly Gly Pro Gln His Lys Ala Arg Val Leu Ala Glu Ala
    355                 360                 365

Met Gln Met Met Gln Ser Asn Ile Met Ala Gln Gln Ser Ala Asn Arg
370                 375                 380

Gly Pro Pro Arg Ser Gly Gly Asn Pro Asn Leu Arg Cys Tyr Asn
385                 390                 395                 400

Cys Gly Lys Pro Gly His Ile Ser Arg Tyr Cys Lys Ala Pro Arg Arg
            405                 410                 415

Lys Gly Cys Trp Lys Cys Gly Ser Pro Asp His Leu Leu Lys Asp Cys
        420                 425                 430

Thr Lys Gln Ile Asn Phe Leu Gly Arg Leu Pro Trp Gly Gln Gly Lys
    435                 440                 445

Pro Arg Asn Phe Pro Leu Thr Ser Leu Thr Pro Ser Ala Pro Gly Met
450                 455                 460

Glu Ser Asn Tyr Asp Pro Ala Glu Glu Met Leu Lys Asn Tyr Leu Arg
465                 470                 475                 480

Arg Ala Gly Glu Gln Lys Arg Gln Gln Arg Gln Glu Ser Lys Lys
            485                 490                 495

Arg Glu Gly Ala Tyr Gln Glu Ala Leu Thr Ser Leu Asn Ser Leu Phe
        500                 505                 510

Gly Ser Asp Gln Leu Gln
        515

<210> SEQ ID NO 46
<211> LENGTH: 1018
<212> TYPE: PRT
<213> ORGANISM: Simian immunodeficiency virus
<220> FEATURE:
<223> OTHER INFORMATION: Deduced amino acid sequence of SIVrcm Pol
      protein

<400> SEQUENCE: 46

Phe Phe Arg Glu Thr Pro Leu Gly Ser Gly Glu Ala Glu Glu Leu Ser
 1               5                  10                  15

Phe Asp Phe Leu Asp Ser Leu Cys Ser Arg Asp Gly Glu Gln Leu Arg
            20                  25                  30

Pro Cys Arg Arg Asp Ala Lys Glu Leu Ser Glu Glu Gly Arg Gly Thr
        35                  40                  45

Lys Glu Thr Thr Glu Ala Gly Arg Glu Gln Glu Glu Arg Gly Ser Ile
    50                  55                  60
```

-continued

```
Ser Gly Ser Leu Asn Leu Pro Gln Phe Ala Leu Trp Lys Arg Pro Thr
 65                  70                  75                  80

Thr Ile Ala Gln Ile Glu Gly Gln Lys Val Glu Val Leu Leu Asp Thr
                 85                  90                  95

Gly Ala Asp Asp Thr Val Ile Glu Gly Ile Glu Leu Gly Asn Asp Trp
            100                 105                 110

Thr Pro Lys Ile Ile Gly Gly Ile Gly Gly Tyr Ile Asn Val Lys Gln
        115                 120                 125

Tyr Lys Asn Cys Glu Ile Glu Ile Ala Gly Lys Arg Thr His Ala His
130                 135                 140

Val Leu Val Gly Pro Thr Pro Val Asn Ile Ile Gly Arg Asn Val Leu
145                 150                 155                 160

Lys Lys Leu Gly Ala Thr Leu Asn Phe Pro Ile Ser Gln Ile Glu Thr
                165                 170                 175

Ile Lys Val Glu Leu Lys Ser Gly Gln Asp Gly Pro Arg Val Lys Gln
            180                 185                 190

Trp Pro Leu Ser Lys Glu Lys Ile Glu Ala Leu Thr Glu Ile Cys Asn
        195                 200                 205

Ala Met Glu Lys Glu Gly Lys Ile Ser Lys Ile Gly Pro Glu Asn Pro
210                 215                 220

Tyr Asn Thr Pro Ile Phe Cys Ile Lys Lys Lys Asp Ser Thr Lys Trp
225                 230                 235                 240

Arg Lys Leu Val Asp Phe Arg Glu Leu Asn Lys Arg Thr Gln Asp Phe
                245                 250                 255

Phe Glu Val Gln Leu Gly Ile Pro His Pro Gly Gly Leu Lys Gln Cys
            260                 265                 270

Glu Arg Ile Thr Val Leu Asp Ile Gly Asp Ala Tyr Phe Ser Cys Leu
        275                 280                 285

Leu Tyr Glu Pro Phe Arg Lys Tyr Thr Ala Phe Thr Ile Pro Ala Val
290                 295                 300

Asn Asn Gln Gly Pro Gly Val Arg Tyr Gln Tyr Asn Val Leu Pro Gln
305                 310                 315                 320

Gly Trp Lys Gly Ser Pro Ala Ile Phe Gln Ala Ser Ala Asn Lys Ile
                325                 330                 335

Leu Gln Pro Phe Arg Glu Glu Asn Pro Asp Val Ile Ile Tyr Gln Tyr
            340                 345                 350

Met Asp Asp Leu Phe Val Gly Ser Asp Arg Thr Lys Leu Glu His Asp
        355                 360                 365

Lys Met Ile Lys Gln Leu Arg Asp His Leu Leu Phe Trp Gly Phe Glu
370                 375                 380

Thr Pro Asp Lys Phe Gln Asp Lys Pro Pro Tyr Leu Trp Met Gly
385                 390                 395                 400

Tyr Glu Leu His Pro Lys Ser Trp Thr Val Gln Glu Ile Lys Leu Pro
                405                 410                 415

Glu Lys Glu Glu Trp Thr Val Asn Asp Ile Gln Lys Leu Val Gly Lys
            420                 425                 430

Leu Asn Trp Ala Ser Gln Ile Tyr Ser Gly Leu Arg Thr Lys Glu Leu
        435                 440                 445

Cys Lys Leu Ile Arg Gly Ala Lys Ala Leu Asp Glu Lys Val Glu Met
450                 455                 460

Thr Lys Glu Ala Glu Ile Glu Tyr Glu Leu Asn Lys Met Ile Leu Lys
465                 470                 475                 480
```

```
Glu Lys Leu His Gly Val Tyr Tyr Asp Glu Lys Pro Leu Val Ala
            485                 490                 495

Asn Ile Gln Lys Leu Glu Gly Gly Gln Trp Ser Tyr Gln Ile Glu Gln
            500                 505                 510

Glu Ser Gly Lys Pro Leu Lys Thr Gly Lys Tyr Ala Lys Gln Lys Thr
            515                 520                 525

Ala His Thr Asn Glu Ile Arg Met Leu Ala Gly Leu Val Gln Lys Ile
            530                 535                 540

Ala Lys Glu Ala Ile Val Ile Trp Gly Arg Leu Pro Thr Phe Arg Leu
545                 550                 555                 560

Pro Ile Glu Arg Glu Val Trp Asp Trp Arg Ser Gln Tyr Trp Gln Val
            565                 570                 575

Thr Trp Ile Pro Asp Trp Glu Phe Val Ser Thr Pro Pro Leu Ile Arg
            580                 585                 590

Leu Gly Tyr Asn Leu Val Lys Asp Pro Ile Pro Gly Glu Glu Val Tyr
            595                 600                 605

Tyr Val Asp Gly Ala Ala Asn Arg Asn Ser Lys Ile Gly Lys Ala Gly
            610                 615                 620

Tyr Val Thr Asn Arg Gly Lys Glu Lys Val Lys Glu Leu Glu Glu Thr
625                 630                 635                 640

Thr Asn Gln Lys Ala Glu Leu Glu Ala Val Leu Leu Ala Leu Lys Asp
            645                 650                 655

Ser Gly Pro Lys Val Asn Ile Val Thr Asp Ser Gln Tyr Val Tyr Gly
            660                 665                 670

Ile Leu Glu Ala Gln Pro Asp Thr Ser Asp Ser Gly Leu Val Thr Glu
            675                 680                 685

Ile Ile Asn Gln Met Ile Gly Lys Glu Ala Val Tyr Leu Ser Trp Val
            690                 695                 700

Pro Ala His Lys Gly Ile Gly Gly Asn Glu Glu Val Asp Lys Leu Val
705                 710                 715                 720

Ser Lys Gly Ile Arg Gln Val Leu Phe Leu Asp Gly Ile Glu Lys Ala
            725                 730                 735

Gln Glu Glu His Glu Lys Tyr His Asn Asn Trp Arg Ala Leu Ala Glu
            740                 745                 750

Asp Phe Gln Ile Pro Gln Ile Val Ala Lys Glu Ile Val Ala Gln Cys
            755                 760                 765

Pro Lys Cys Gln Val Lys Gly Glu Ala Ile His Gly Gln Val Asp Ala
770                 775                 780

Ser Pro Gly Thr Trp Gln Met Asp Cys Thr His Leu Glu Gly Lys Ile
785                 790                 795                 800

Ile Ile Val Ala Val His Val Ala Ser Gly Tyr Ile Glu Ala Glu Val
            805                 810                 815

Ile Pro Ala Glu Thr Gly Lys Glu Thr Ala His Phe Leu Leu Lys Leu
            820                 825                 830

Ala Ala Arg Trp Pro Val Arg Lys Leu His Thr Asp Asn Gly Ala Asn
            835                 840                 845

Phe Thr Ser Ala Ala Val Gln Ala Val Cys Trp Trp Ala Gln Ile Glu
            850                 855                 860

His Ala Phe Gly Val Pro Tyr Asn Pro Gln Ser Gln Gly Val Val Glu
865                 870                 875                 880

Ser Met Asn Lys Gln Leu Lys Ile Ile Ile Glu Gln Val Arg Glu Gln
            885                 890                 895

Ala Glu Lys Leu Glu Thr Ala Val Gln Met Ala Val Leu Val His Asn
```

```
                    900             905             910
Phe Lys Arg Lys Gly Ile Gly Gly Tyr Ser Ala Gly Glu Arg Ile
                915             920             925

Ile Asp Ile Ile Ala Thr Asp Leu Ala Thr Asn Lys Leu Gln Asn Gln
    930             935             940

Ile Ser Lys Ile Gln Asn Phe Arg Val Tyr Tyr Arg Glu Gly Arg Asp
945             950             955             960

Gln Leu Trp Arg Gly Pro Ala Lys Leu Ile Trp Lys Gly Glu Gly Ala
                965             970             975

Val Val Ile Gln Glu Glu Thr Gly Asp Leu Lys Val Val Pro Arg Arg
                980             985             990

Lys Ala Lys Ile Ile Lys Glu Tyr Gly Arg Lys Asp Val Asp Ser Glu
                995             1000            1005

Ala Asn Leu Ala Gly Arg Gln Glu Glu Asn
    1010            1015
```

<210> SEQ ID NO 47
<211> LENGTH: 216
<212> TYPE: PRT
<213> ORGANISM: Simian immunodeficiency virus
<220> FEATURE:
<223> OTHER INFORMATION: Deduced amino acid sequence of SIVrcm Vif
      protein

<400> SEQUENCE: 47

```
Met Ala Glu Lys Met Trp Ile Val Arg Pro Ile Trp Arg Val Asp Arg
  1               5                  10                  15

Arg Lys Ile Glu Gln Trp His Ser Leu Val Lys Tyr His Gln Tyr Lys
                 20                  25                  30

Gly Lys Lys Ala Ala Lys Glu Trp Glu Tyr Val Pro His Phe Lys Val
             35                  40                  45

Pro Trp Gly Trp Trp Ser His Ser Glu Val His Ile Pro Leu Glu Glu
         50                  55                  60

Gly Ser Lys Leu Lys Ile Thr Thr Tyr Trp Asn Leu Thr Val Glu Lys
 65                  70                  75                  80

Gly Trp Leu Gly Thr Tyr Gly Val Gly Ile Leu Trp Ile Lys Gly Asp
                 85                  90                  95

Tyr Val Thr Asp Val Phe Pro Trp Thr Ala Asp Ser Leu Ile His Lys
                100                 105                 110

Ile Tyr Phe Pro Cys Phe Thr Asp Arg Ala Ile Arg Gln Ser Leu Leu
            115                 120                 125

Gly Glu Lys Val Leu Val Cys Ala Phe Gln Gly His Arg Asp Gln
    130                 135                 140

Val Gly Thr Leu Gln Phe Leu Ala Ile Gln Ala Trp Ala Lys Ser Gln
145                 150                 155                 160

Leu Asp Arg Tyr Gly Arg Lys Ser Pro Arg Gly Pro His Trp Gly Trp
                165                 170                 175

Arg Ser Arg Val Pro Ala Leu Ala Thr Gly His Ala Arg Lys Gly Gln
            180                 185                 190

Leu Gly Ser Gln Val Thr Leu Ser Ser Arg Val His Phe Pro Ser Val
        195                 200                 205

Ala His Leu Cys Gly Thr Leu Ala
    210                 215
```

<210> SEQ ID NO 48
<211> LENGTH: 104

```
<212> TYPE: PRT
<213> ORGANISM: Simian immunodeficiency virus
<220> FEATURE:
<223> OTHER INFORMATION: Deduced amino acid sequence of SIVrcm Vpx
      protein

<400> SEQUENCE: 48

Met Ala Glu Arg Ala Pro Glu Val Pro Thr Gly Ala Gly Ala Glu
 1               5                  10                  15

Phe Gln Pro Trp Leu Arg Asp Met Leu Glu Lys Val Asn Leu Glu Ala
                20                  25                  30

Arg Leu His Phe His Pro Glu Phe Ile Phe Arg Leu Trp Arg Thr Cys
                35                  40                  45

Val Glu His Trp His Asp Val His Gln Arg Ser Leu Glu Tyr Ala Ala
        50                  55                  60

Tyr Arg Tyr Leu Leu Leu Met Gln Lys Ala Leu Phe Ile His Cys Gln
 65                 70                  75                  80

Thr Gly Cys Ser Gln Arg His Gly Pro Asn Pro Arg Ala Val Gly Glu
                85                  90                  95

Arg Ile Thr Ile Leu Pro Gly Met
                100

<210> SEQ ID NO 49
<211> LENGTH: 100
<212> TYPE: PRT
<213> ORGANISM: Simian immunodeficiency virus
<220> FEATURE:
<223> OTHER INFORMATION: Deduced amino acid sequence of SIVrcm Vpr
      protein

<400> SEQUENCE: 49

Met Glu Leu Pro Pro Glu Asp Glu Gly Pro Gln Arg Glu Pro Tyr Asp
 1               5                  10                  15

Glu Trp Leu Met Asp Thr Leu Ile Glu Leu Gln Glu Glu Ala Lys Lys
                20                  25                  30

His Phe Thr Tyr Ala Leu Leu Thr Gln Ile Gly Asp Tyr Val Tyr Glu
                35                  40                  45

Gln His Gly Asp Ser Ile Glu Gly Val Gln Ala Met Ile Arg Leu Leu
        50                  55                  60

Gln Arg Ala Leu Phe Leu His Phe Arg Asn Gly Cys Ala Gly Ser Arg
 65                 70                  75                  80

Ile Gly Thr Ser Arg Gly Ser Asn Pro Leu Arg Ser Ile Pro Gln Thr
                85                  90                  95

Arg Asn Ile Met
            100

<210> SEQ ID NO 50
<211> LENGTH: 106
<212> TYPE: PRT
<213> ORGANISM: Simian immunodeficiency virus
<220> FEATURE:
<223> OTHER INFORMATION: Deduced amino acid sequence of SIVrcm Tat
      protein

<400> SEQUENCE: 50

Met Asp Val Gln Gly Val Gly Leu Glu His Pro Glu Glu Val Ile Leu
 1               5                  10                  15

Tyr Asp Pro Phe Arg Lys Arg Gly Thr Ser Cys Asn Thr Cys Tyr Cys
                20                  25                  30

Lys Lys Cys Cys Tyr His Cys Gln Leu Cys Phe Leu Gln Lys Gly Leu
```

```
                     35                  40                  45
Gly Ile Asn Tyr Ala Ser Arg Ala Arg Arg Arg Ser Lys Glu Glu
         50                  55                  60

Asn Lys Ala Asp Lys Phe Pro Val Pro Asn His Arg Ser Ile Ser Thr
 65                  70                  75                  80

Thr Arg Gly Asn Arg Lys Leu Gln Glu Lys Lys Glu Lys Thr Val Glu
                 85                  90                  95

Lys Lys Val Ala Thr Ser Thr Thr Ile Gly
            100                 105

<210> SEQ ID NO 51
<211> LENGTH: 94
<212> TYPE: PRT
<213> ORGANISM: Simian immunodeficiency virus
<220> FEATURE:
<223> OTHER INFORMATION: Deduced amino acid sequence of SIVrcm Rev
      protein

<400> SEQUENCE: 51

Met Leu Pro Gly Gln Asp Glu Glu Asp Leu Arg Lys Lys Ile Arg Leu
  1               5                  10                  15

Ile Asn Phe Leu Tyr Leu Ile Thr Asp Pro Tyr Pro Gln His Gly Gly
                 20                  25                  30

Thr Ala Asn Ser Arg Arg Lys Lys Arg Arg Arg Trp Arg Arg Arg Trp
             35                  40                  45

Gln Gln Val Gln Gln Leu Ala Glu Arg Ile Leu Leu Asp Ser Thr Asp
         50                  55                  60

Pro Pro Val Glu Gln Asp Leu Asp Ala Ala Ile Ala Asp Leu Gln Lys
 65                  70                  75                  80

Leu Gln Leu Asn Asn Leu Pro Glu Pro Pro Val Asp Phe Ser
                 85                  90

<210> SEQ ID NO 52
<211> LENGTH: 850
<212> TYPE: PRT
<213> ORGANISM: Simian immunodeficiency virus
<220> FEATURE:
<223> OTHER INFORMATION: Deduced amino acid sequence of SIVrcm Env
      protein

<400> SEQUENCE: 52

Met Asp Lys Lys Leu Val Ile Val Leu Ile Val Ile Gly Ile Ile
  1               5                  10                  15

Leu Val Gln Gly Ser Gln Lys Pro Gln Tyr Ile Thr Val Phe Tyr Gly
                 20                  25                  30

Val Pro Val Trp Arg Asn Ser Thr Val Pro Met Phe Cys Val Thr Asp
             35                  40                  45

Asn Thr Gln Ser Trp Gly Thr Leu Asn Cys Ile Pro Glu Gly Gly Ile
         50                  55                  60

Ser Pro Glu Val Ser Ile Asn Val Ser Glu Arg Phe Asp Ala Trp Asn
 65                  70                  75                  80

Asn Ser Leu Tyr Glu Gln Ala Lys Asp Asn Val Trp Asn Leu Tyr Asp
                 85                  90                  95

Ser Thr Leu Lys Pro Cys Val Arg Leu Ser Pro Leu Cys Ile Thr Met
                100                 105                 110

Asn Cys Ser Ala Ile Asn Gly Ser Trp Asp Gly Ile Pro Thr Ser Ala
            115                 120                 125

Pro Pro Thr Thr Thr Lys Thr Thr Thr Gln Arg Thr Ile Gly Val Glu
```

```
                130                 135                 140
Lys Glu Cys Thr Ala Gly Asn Glu Thr Cys Glu Glu Val Gln Asp Ala
145                 150                 155                 160

Asp Val Met Ser Cys Glu Phe Ala Val Ala Gly Leu Lys Arg Asp Glu
                165                 170                 175

Lys His Lys Tyr Asn Asp Thr Trp Tyr Ser Arg Asp Leu Trp Cys Glu
                180                 185                 190

Lys Glu Thr Asn Ser Thr Asn Ser Thr Lys Lys Cys Phe Val Arg
                195                 200                 205

His Cys Asn Thr Thr Ser Ile Gln Gln Phe Cys Glu Pro Lys Tyr Trp
                210                 215                 220

Glu Pro Phe Arg Leu Arg Tyr Cys Ala Pro Pro Gly Phe Ala Leu Leu
225                 230                 235                 240

Val Cys Lys Asp Lys Asn Tyr Thr Gly Phe Asp Thr Cys Val Asn Val
                245                 250                 255

Thr Ala Thr Ser Cys Thr His Met Ile Asn Thr Thr Val Ala Ser Gly
                260                 265                 270

Phe Gly Leu Asn Gly Ser Ile Asn Val Asn Glu Thr Trp Ile Tyr Gln
                275                 280                 285

Arg Arg Gln Ser Asn Arg Thr Val Ile Gly Leu Asn Ser Phe Tyr Asn
                290                 295                 300

Leu Ser Val Thr Cys Arg Arg Pro Ser Asn Arg Thr Val Lys Gly Ile
305                 310                 315                 320

Ser Leu Ala Thr Gly Val Phe Ile Ser Leu Arg Val Glu Lys Arg Pro
                325                 330                 335

Lys Gly Ala Trp Cys Arg Phe Glu Gly Asn Trp Thr Asp Ala Trp Lys
                340                 345                 350

Glu Val Lys Glu Arg Val Lys Thr Thr Lys Gly Tyr Arg Gly Thr Ser
                355                 360                 365

Asn Thr Asp Lys Ile Lys Ile Arg Thr Val Tyr Gly Gly Asp Asp Glu
                370                 375                 380

Ala Arg Tyr Phe Trp Leu Asn Cys Asn Gly Glu Phe Leu Tyr Cys Lys
385                 390                 395                 400

Leu Asn Trp Phe Leu Asn Leu Asn Asn Glu Thr Val Gly Thr Thr
                405                 410                 415

Asn Glu Lys Arg Lys Ala Pro Phe Val Pro Cys Ile Thr Lys Met Ile
                420                 425                 430

Val Asn Asp Trp Tyr Thr Val Ser Arg Lys Val Tyr Thr Pro Pro Arg
                435                 440                 445

Pro Asp Ala Leu Lys Cys Ser Ala Gln Val Ser Tyr Leu Leu Ala Asp
                450                 455                 460

Ile Asp Tyr Ile Asn Asp Ser Glu Thr Asn Ile Thr Leu Ser Ala Glu
465                 470                 475                 480

Val Gly Asp Tyr Trp Ala Ala Glu Leu Gly Arg Tyr Lys Ala Ile Glu
                485                 490                 495

Ile Arg Pro Ile Gly Phe Ala Pro Thr Glu Ile Lys Arg Tyr Gln Thr
                500                 505                 510

Lys Gln Lys Arg Val Pro Leu Val Leu Gly Phe Leu Gly Phe Leu Ser
                515                 520                 525

Ala Ala Gly Thr Ala Met Gly Ala Ala Thr Ala Leu Thr Val Gln
                530                 535                 540

Ser Arg His Leu Leu Ala Gly Ile Leu Gln Gln Lys Asn Leu Leu
545                 550                 555                 560
```

```
Asp Ile Val Lys Arg Gln Gln Asn Leu Leu Lys Leu Thr Val Trp Gly
            565                 570                 575

Thr Lys Asn Leu Gln Ala Arg Val Thr Ala Ile Glu Lys Tyr Leu Ala
        580                 585                 590

Asp Gln Ser Leu Leu Asn Thr Phe Gly Cys Ala Trp Arg Gln Val Cys
        595                 600                 605

His Thr Val Pro Trp Thr Phe Asn Lys Thr Pro Glu Trp Gln Lys
        610                 615                 620

Glu Ser Trp Leu Gln Trp Glu Arg Asn Ile Ser Tyr Leu Glu Ala Asn
625                 630                 635                 640

Ile Thr Ile Ala Leu Gln Glu Ala Gln Asp Gln His Glu Lys Asn Val
                645                 650                 655

His Glu Leu Glu Lys Leu Ser Asn Trp Gly Asp Ala Phe Ser Trp Leu
                660                 665                 670

Asn Leu Asp Trp Trp Met Gln Tyr Ile Lys Ile Gly Phe Phe Ile Val
                675                 680                 685

Ile Gly Ile Ile Gly Leu Arg Val Ala Trp Leu Leu Trp Asn Cys Leu
            690                 695                 700

Ser Asn Leu Arg Gln Gly Tyr Arg Pro Leu Ser Pro Ser Tyr Val
705                 710                 715                 720

Gln Gln Ile His Ile His Asn Thr Gly Glu Pro Gln Thr Pro Gly Glu
                725                 730                 735

Lys Arg Glu Asp Gly Gly Glu Gly Gly Asn Lys Tyr Asn Asn Trp
                740                 745                 750

Leu Arg Glu Tyr Cys Trp Ile Gln Leu Ile His Pro Leu Ser Arg Ile
                755                 760                 765

Trp Thr Gln Leu Ser Gln Ile Cys Arg Ser Cys Ser Ser Ile Ile Phe
            770                 775                 780

Gln Ser Leu Arg Trp Ile Leu Ala Lys Ile Gln Tyr Gly Trp Gln Glu
785                 790                 795                 800

Phe Lys Glu Phe Ser Ser Trp Phe Ala Glu Met Ala Leu Gln Asn Ala
                805                 810                 815

Tyr Tyr Thr Trp Arg Gly Leu Cys Ala Val Ala Arg Asp Phe Ala Gly
                820                 825                 830

Trp Pro Ala Met Val Cys Arg Arg Ile Arg Gln Gly Leu Glu Arg Leu
                835                 840                 845

Cys Asn
    850

<210> SEQ ID NO 53
<211> LENGTH: 224
<212> TYPE: PRT
<213> ORGANISM: Simian immunodeficiency virus
<220> FEATURE:
<223> OTHER INFORMATION: Deduced amino acid sequence of SIVrcm Nef
      protein

<400> SEQUENCE: 53

Met Gly Gly Lys Ser Ser Lys Asn Ser Ala Ala Gly Leu Leu Arg Trp
1               5                   10                  15

Arg Phe Lys Met Leu Thr Thr Pro Gly Glu Gly Tyr Val Arg Trp His
                20                  25                  30

Glu Thr Leu Leu Asp Gly Gln Pro Trp Cys Ala Glu Gly Ser Gly Arg
            35                  40                  45

Ala Ser Arg Asp Phe Val Ile Arg Gly Gly Ile Thr Ala Glu Thr Gln
```

-continued

```
                    50                      55                      60
Ala Ser Ile Asp Asp Ile Asp Trp Tyr Glu Asp Thr Asp Asp Thr Leu
 65                      70                      75                      80

Val Gly Phe Pro Val Lys Pro Gln Val Pro Leu Arg Pro Met Ser Tyr
                        85                      90                      95

Lys Leu Ala Ile Asp Met Ser His Phe Leu Lys Glu Lys Gly Gly Leu
                       100                     105                     110

Glu Gly Ile Tyr Trp Ser Ile Arg Arg Gln Arg Ile Leu Asp Met Tyr
                       115                     120                     125

Leu Glu Asn Glu His Gly Ile Ile Pro Asp Trp Gln Asn Tyr Thr Pro
                130                     135                     140

Gly Pro Gly Ile Arg Tyr Pro Thr Leu Phe Gly Trp Leu Trp Gln Leu
145                     150                     155                     160

Val Pro Val Asp Val Ser Asp Glu Ala Arg Glu Asp Glu His Ser
                       165                     170                     175

Leu Leu His Pro Ala Glu Thr Ser Gly Met Glu Asp Pro Trp Gly Glu
                       180                     185                     190

Val Leu Ala Trp Lys Phe Asn Pro Met Leu Ala Val Asp Tyr Ile Gly
                       195                     200                     205

Tyr Arg Leu His Pro Glu Phe Phe Gly Glu Arg Lys Asn Lys Thr Gln
                210                     215                     220
```

<210> SEQ ID NO 54
<211> LENGTH: 318
<212> TYPE: PRT
<213> ORGANISM: Simian immunodeficiency virus
<220> FEATURE:
<223> OTHER INFORMATION: Deduced amino acid sequence of SIVrcm gag
      gene

<400> SEQUENCE: 54

```
Lys Tyr Met Leu Lys His Leu Val Trp Ala Cys Lys Lys Leu Asn Lys
  1               5                      10                      15

Phe Gly Leu Ser Asp His Leu Leu Glu Thr Ala Thr Gly Cys Glu Lys
                 20                      25                      30

Ile Leu Gly Val Leu Leu Pro Leu Val Pro Thr Gly Ser Glu Gly Leu
                 35                      40                      45

Lys Ser Leu Phe Asn Leu Cys Cys Val Leu Trp Cys Val His Lys Glu
         50                      55                      60

Val Lys Val Lys Asp Thr Glu Glu Ala Val Ala Lys Val Lys Glu Cys
 65                      70                      75                      80

Cys His Leu Val Glu Lys Ala Glu Asn Thr Thr Glu Lys Glu Lys Gly
                 85                      90                      95

Ala Thr Ala Pro Pro Ser Gly Gln Arg Gly Asn Tyr Pro Ile Ile Thr
                100                     105                     110

Ile Asn Gln Gln Pro Glu His Asn Pro Ile Ser Pro Arg Thr Leu Asn
                115                     120                     125

Ala Trp Val Lys Val Val Glu Lys Lys Phe Ser Ala Glu Val Ala
                130                     135                     140

Pro Met Phe Ser Ala Leu Ser Glu Gly Cys Ile Pro Tyr Asp Ile Asn
145                     150                     155                     160

Gln Met Leu Asn Ala Ile Gly Glu His Gln Gly Ala Leu Gln Ile Val
                165                     170                     175

Lys Glu Val Ile Asn Glu Glu Ala Ala Asp Trp Asp Ala Arg His Pro
                180                     185                     190
```

```
Val Pro Gly Pro Ile Pro Ala Gly Gln Leu Arg Glu Pro Thr Gly Ser
        195                 200                 205

Asp Ile Ala Gly Thr Thr Ser Ser Ile Ala Glu Gln Ile Ala Trp Thr
        210                 215                 220

Thr Arg Ala Asn Asn Pro Ile Asn Val Gly Asn Leu Tyr Arg Asn Trp
225                 230                 235                 240

Ile Ile Val Gly Leu Gln Lys Trp Val Lys Met Tyr Asn Pro Val Asn
                245                 250                 255

Ile Leu Asp Ile Lys Gln Gly Pro Lys Glu Ser Phe Lys Asp Tyr Val
                260                 265                 270

Asp Arg Phe Tyr Lys Ala Leu Arg Ala Glu Gln Ala Asp Pro Ala Val
        275                 280                 285

Lys Asn Trp Met Thr Gln Ser Leu Leu Ile Gln Asn Ala Asn Pro Asp
        290                 295                 300

Cys Lys Met Val Leu Lys Gly Leu Gly Met Asn Pro Ser Leu
305                 310                 315
```

<210> SEQ ID NO 55
<211> LENGTH: 954
<212> TYPE: DNA
<213> ORGANISM: Simian immunodeficiency virus
<220> FEATURE:
<223> OTHER INFORMATION: Partial nucleotide sequence of SIVrcm gag gene;
      GenBank Accession No. AF028608

<400> SEQUENCE: 55

```
aaatacatgc tgaagcattt ggtatgggca tgcaaaaaac taaataaatt tggcttgagt      60
gatcatttgt tagaaacagc aacaggatgt gaaaaaatat taggagtcct gctgcctcta     120
gttccgacag ggtcagaggg gctaaaaagc ctctttaatt tgtgctgcgt actctggtgc     180
gtacacaagg aagtgaaagt gaaagacaca gaggaagctg tagcaaaagt gaaagaatgc     240
tgccatctag tggaaaaagc agaaaataca acagaaaaag aaagggagc aacagcgcca      300
cctagtggac aaagaggaaa ttatcctata attactataa atcagcagcc tgagcataat     360
cctatatcac caaggactct aaatgcctgg gtcaaggtgg tagaggagaa aaaattctca     420
gcagaagtag cgcccatgtt ctcggcacta tcagaaggct gcataccctcta tgatataaat     480
caaatgctaa atgccatagg ggaacaccag ggtgcgctgc agatagtaaa ggaagtgatc     540
aatgaggaag cagcagactg ggatgctaga catccagtac caggcccgat accagcaggg     600
caacttagag aaccaacagg aagtgacata gcagggacaa ctagctcaat agcagaacag     660
atagcttgga ccaccagagc aaacaaccc attaatgtgg gcaatctgta cagaaattgg     720
ataatagtag ggttacaaaa atgggtaaaa atgtacaatc cagtgaacat cctagatata     780
aagcaaggac caaagagtc attcaaggat tatgtggata gatttataaa agccttgaga     840
gcagaacagg cagacccggc agtaaaaaat tggatgacac aatcactgct gatacaaaat     900
gctaacccag actgtaaaat ggtactcaag ggtctgggaa tgaacccttc ttta            954
```

<210> SEQ ID NO 56
<211> LENGTH: 158
<212> TYPE: PRT
<213> ORGANISM: Simian immunodeficiency virus
<220> FEATURE:
<222> LOCATION: 148
<223> OTHER INFORMATION: Deduced amino acid sequence of SIVrcm pol gene;
      Xaa = unknown

<400> SEQUENCE: 56

```
Ile Pro Ala Glu Thr Gly Lys Glu Thr Ala Tyr Phe Leu Leu Lys Leu
 1               5                  10                 15

Ala Ala Arg Trp Pro Val Arg Lys Leu His Thr Asp Asn Gly Ala Asn
             20                  25                 30

Phe Thr Ser Ala Ala Val Gln Ala Val Cys Trp Trp Ala Gln Ile Glu
         35                  40                  45

His Thr Phe Gly Val Pro Tyr Asn Pro Gln Ser Gln Gly Val Val Glu
     50                  55                  60

Ser Met Asn Lys Gln Leu Lys Ile Ile Ile Glu Gln Val Arg Glu Gln
 65                  70                  75                  80

Ala Glu Lys Leu Glu Thr Ala Val Gln Met Ala Val Leu Val His Asn
                 85                  90                  95

Phe Lys Arg Lys Gly Gly Ile Gly Gly Tyr Ser Ala Gly Glu Arg Ile
             100                 105                 110

Ile Asp Ile Ile Ala Thr Asp Leu Ala Thr Asn Lys Leu Gln Asn Gln
         115                 120                 125

Ile Ser Lys Ile Gln Asn Phe Arg Val Tyr Tyr Arg Glu Gly Arg Asp
     130                 135                 140

Gln Leu Trp Xaa Gly Pro Ala Lys Leu Ile Trp Lys Gly Glu
145                 150                 155
```

<210> SEQ ID NO 57
<211> LENGTH: 475
<212> TYPE: DNA
<213> ORGANISM: Simian immunodeficiency virus
<220> FEATURE:
<222> LOCATION: 444
<223> OTHER INFORMATION: Partial nucleotide sequence of SIVrcm pol gene;
      n = unknown; GenBank Accession No. AF028607

<400> SEQUENCE: 57

```
aataccagca gaaacaggaa aagagacagc atatttcctg ttgaaactag cagcaagatg      60
gccagtaagg aagctacaca cagataatgg agcaaatttc acaagtgcag cagtacaggc     120
ggtctgctgg tgggctcaga tagagcacac ctttggagta ccttacaatc ctcaaagtca     180
aggagtagtg gaaagcatga ataaacaatt aaaaataatc atagaacaag taagagaaca     240
agcagaaaaa ttagaaacag cagtccaaat ggcagttttg gttcacaatt ttaaaagaaa     300 agggggatt gggggtaca gtgcaggaga aagaataata gatataatag caacagactt     360
agcaaccaat aaaattacaa atcaaatttc aaaaattcaa aattttcggg tttattacag     420
agaaggaagg gatcaactgt gganaggtcc agctaagctg atctggaaag gtgaa          475
```

<210> SEQ ID NO 58
<211> LENGTH: 52
<212> TYPE: RNA
<213> ORGANISM: Simian immunodeficiency virus
<220> FEATURE:
<221> NAME/KEY: stem_loop
<223> OTHER INFORMATION: Nucleotide sequence of SIVrcm LTR sequence
      having a duplicated TAR stemloop structure

<400> SEQUENCE: 58

```
ccggauugag ccuggguguu cucuggccag cuugagccug gguguucgcu gg              52
```